US009617229B2

(12) United States Patent
Blough et al.

(10) Patent No.: US 9,617,229 B2
(45) Date of Patent: Apr. 11, 2017

(54) PHENYLMORPHOLINES AND ANALOGUES THEREOF

(75) Inventors: Bruce E. Blough, Raleigh, NC (US); Richard Rothman, Ellicott City, MD (US); Antonio Landavazo, Raleigh, NC (US); Kevin M. Page, Willow Spring, NC (US); Ann Marie Decker, Durham, NC (US)

(73) Assignees: Research Triangle Institute, Research Triangle Park, NC (US); The United States of America, As Represented by the Secretary Department of Health and Human Services, Washington, DC (US)

( * ) Notice: Subject to any disclaimer, the term of this patent is extended or adjusted under 35 U.S.C. 154(b) by 194 days.

(21) Appl. No.: 13/698,892

(22) PCT Filed: May 20, 2011

(86) PCT No.: PCT/US2011/037361
§ 371 (c)(1),
(2), (4) Date: Mar. 4, 2013

(87) PCT Pub. No.: WO2011/146850
PCT Pub. Date: Nov. 24, 2011

(65) Prior Publication Data
US 2013/0203752 A1  Aug. 8, 2013

Related U.S. Application Data

(60) Provisional application No. 61/347,259, filed on May 21, 2010.

(51) Int. Cl.
C07D 265/30 (2006.01)

(52) U.S. Cl.
CPC ................. C07D 265/30 (2013.01)

(58) Field of Classification Search
CPC .................................................. C07D 265/30
USPC ........................ 544/106; 514/231.2
See application file for complete search history.

(56) References Cited

U.S. PATENT DOCUMENTS

| | | | |
|---|---|---|---|
| 1,867,982 A | 7/1932 | Naunton et al. |
| 2,364,347 A | 12/1944 | Dickey et al. |
| 2,832,777 A | 4/1958 | Kalm |
| 2,996,504 A | 8/1961 | Zimmermann et al. |
| 2,997,469 A | 8/1961 | Heel et al. |
| 3,018,222 A | 1/1962 | Siemer et al. |
| 3,112,311 A | 11/1963 | Zimmermann et al. |
| 3,117,967 A | 1/1964 | Anderson et al. |
| 3,125,572 A | 3/1964 | Siemer et al. |
| 3,225,042 A | 12/1965 | Dillard et al. |
| 3,555,019 A | 1/1971 | Fouche et at |
| 3,642,789 A | 2/1972 | Faith et al. |
| 3,714,161 A | 1/1973 | Mallion et al. |
| 3,959,273 A | 5/1976 | Mallion et al. |
| 4,044,131 A | 8/1977 | Asselin et al. |
| 4,360,519 A | 11/1982 | White et al. |
| 4,576,944 A | 3/1986 | Lafon |
| 4,766,212 A | 8/1988 | Freedman et al. |
| 5,104,870 A | 4/1992 | Kelley et al. |
| 5,648,347 A | 7/1997 | Mehta et al. |
| 6,693,192 B1 | 2/2004 | Chrysselis et al. |
| 8,906,908 B2 | 12/2014 | Carroll et al. |
| 2005/0267096 A1 | 12/2005 | Allerton et al. |
| 2007/0155729 A1 | 7/2007 | Morgan et al. |
| 2010/0016312 A1 | 1/2010 | Lee et al. |
| 2012/0071560 A1 | 3/2012 | Carroll et al. |

FOREIGN PATENT DOCUMENTS

| | | |
|---|---|---|
| DE | DD20678 | 4/1958 |
| DE | 11 35 464 | 8/1962 |
| DE | 11 43 201 | 2/1963 |
| DE | 2152686 | 5/1972 |
| DE | 2441350 | 3/1976 |
| EP | 0 116 373 | 8/1984 |
| EP | 0 170 430 | 2/1986 |
| EP | 0 174 242 | 3/1986 |
| FI | 852 657 | 1/1986 |
| FR | 1 397 563 | 4/1965 |
| FR | 2168139 | 8/1973 |
| FR | 2285886 | 9/1974 |
| FR | 2471378 | * 6/1981 |

(Continued)

OTHER PUBLICATIONS

RN 1097796-78-5, STN, file Registry, Jan. 30, 2009.*
Carroll et al., "Synthesis and Biological Evaluation of Bupropion analogues as Potential Pharmacotherapies for Cocaine Addiction," J. Med. Chem., 2009, pp. 6768-6781, vol. 52.
Carroll et al., "Synthesis of 2-(Substituted Phenyl)-3,5,5-trimethylmorpholine Analogues and Their Effects on Monoamine Uptake, Nicotinic Acetylcholine Receptor Function, and Behavioral Effects of Nicotine," Journal of Medicinal Chemistry, 2011, pp. 1441-1448, vol. 54, No. 5.
Hu et al., "Synthesis of 2-aryl-3,5,5-trimethyl-2-morpholinol Hydrochloride," Yingyong Huaxue, 2005, pp. 343-345, vol. 22, No. 3.
Lukas et al., "Synthesis and Characterization of In Vitro and In Vivo Profiles of Hydroxybupropion analogues: Aids to Smoking Cessation," Journal of Medicinal Chemistry, 2010, pp. 4731-4748, vol. 53.
Avramova et al., "Derivatives of 2-and 2,3-Disubstituted Tetrahydrooxazines," Bulgarian Chemical Communications, 1992, pp. 387-390, vol. 25, No. 3.
Balsamo et al., "Synthesis and Pharmacological Properties of cis-2-(2,5-dimethoxyphenyl)-3-Methylmorpholine and Its N-isopropyl Derivative," Eur. J. Med. Chem.—Chimica Therapeutica, 1978, pp. 321-326, vol. 13, No. 4.
Bettoni et al., "Synthesis of Rigid Dopamine Congeners: CIS and TRANS 2-(p-Methoxyphenyl)-3- Methylmorpholine," Tetrahedron, 1986, pp. 2117-2120, vol. 42, No. 7.

(Continued)

Primary Examiner — Rebecca Anderson
(74) Attorney, Agent, or Firm — Womble Carlyle Sandridge & Rice, LLP

(57) ABSTRACT

Provided herein are compounds and prodrugs and methods of preparation of compounds and prodrugs that are capable of functioning as releasers and/or uptake inhibitors of one or more monoamine neurotransmitters, including dopamine, serotonin, and norepinephrine. Also provided are pharmaceutical compositions comprising one or more of these compounds or prodrugs, which may further comprise one or more additional therapeutic agents. Also provided are methods of treatment of various conditions that may be responsive to modification of monoamine neurotransmitter levels, such as pre-obesity, obesity, addiction, and depression.

21 Claims, No Drawings

(56) References Cited

FOREIGN PATENT DOCUMENTS

| FR | 2553411 | 10/1983 |
|---|---|---|
| GB | 773780 | 5/1957 |
| GB | 817932 | 8/1959 |
| GB | 851311 | 10/1960 |
| GB | 862198 | 3/1961 |
| GB | 868987 | 5/1961 |
| GB | 883220 | 11/1961 |
| GB | 899386 | 6/1962 |
| GB | 1 298 771 | 12/1972 |
| GB | 1 411 666 | 10/1975 |
| GB | 1 336 732 | 11/1993 |
| JP | H0314562 | 1/1991 |
| JP | H03206084 | 9/1991 |
| JP | 2005-507367 | 3/2005 |
| WO | WO 92/18489 | 10/1992 |
| WO | WO 93/15052 | 8/1993 |
| WO | WO 99/37305 | 7/1999 |
| WO | WO 00/42030 | 7/2000 |
| WO | WO 01/62257 | 8/2001 |
| WO | WO 2004/052372 | 6/2004 |
| WO | WO 2008/026046 | 3/2008 |
| WO | WO 2008/087512 | 7/2008 |

OTHER PUBLICATIONS

Blagg et al., "Design and Synthesis of a Functionally Selective D3 Agonist and its in Vivo Delivery Via the Intranasal Route," Bioorganic & Medicinal Chemistry Letters, 2007, pp. 6691-6696, vol. 17.
Boswell et al., "Synthesis and Anti-Tetrabenazine Activity of C-3 Analogues of Dimethyl-2-phenylmorpholines," J. Heterocyclic Chem., 1996, pp. 33-39, vol. 33, No. 33.
Dijkstra et al., "Synthesis and Phamracology of trans-4-n-Propyl-3,4,4a,10b-tetrahydro-2H,5H-1-Benzopyrano[4,3,-b-]-1,4-Oxazin-7- and -9ols: The Significance of Nitrogen $pK_a$ Values for Central Dopamine Receptor Activation," J. Med. Chem., 1988, pp. 2178-2182, vol. 31.
Franklin et al., "The Metabolism of Phenmetrazine in Man and Laboratory Animals," Drug Metabolism and Disposition, 1977, pp. 223-233, vol. 5, No. 3.
Glennon et al., β-Oxygenated Analogues of the 5-HT$_{2A}$ Serotonin Receptor Agonist 1-(4-Bromo-2,5-dimethoxyphenyl)-2-aminopropane, J. Med. Chem., 2004, pp. 6034-6041, vol. 47.
Kalm et al., "4-Aminomorpholines," J. Med. Chem., 1964, pp. 427-433.
Ludwig et al., "Electrophilic Asymmetric Syntheses of α-Hydroxy Carboxylic Acids," Tetrahedron Letters, 1986, pp. 2731-2734, vol. 27. No. 24.
Manera et al., "X-Ray analysis, Theoretical Studies and α-Adrenergic Biopharmacological Properties of 1-(2,4-Dimethoxyphenyl)-2-Aminoethanol and its Morpholine Analogue," Eur J. Med Chem., 1994, pp. 519-525, vol. 29.
Negus et al., "Selective Suppression of Cocaine- Versus Food-Maintained responding by Monoamine Releasers in Rhesus Monkeys: Benzylpiperazine, (+) Phenmetrazine, and 4-Benzylpiperidine," The Journal of Pharmacology and Experimental Therapeutics, 2009, pp. 272-281, vol. 329, vol. 1.
Rothman et al., "Amphetamine-Type Central Nervous System Stimulants Release Norepinephrine More Potently Than They Release Dopamine and Serotonin," Synapse, 2000, 39:32-41 (2001).
Rothman et al., "Interaction of the Anorectic Medication, Phendimetrazine, and its Metabolites with Monoamine Transporters in Rat Brain," Eur J Pharmacol, 2002, 447(1):51-7.
Sheradsky et al., "The Reaction of Phenylglyoxal with 2-Aminoalcohols. Rearrangement of 2-Acyloxazolidines to 2-Hydroxy-5,6-Dihydro-1,4-Oxazines," J. Heterocyclic Chem, 1996, pp. 1271-1274, vol. 33.
Stevens et al., "Epoxy Ethers. XX. Synthesis of Diamines, Morpholines, and Piperazines," Department of Chemistry, Wayne Slate University, Detroit 1, Michigan, Journal of Organic Chemistry, 1964, pp. 3146-3151, vol. 29.
Swist et al., "Determination of Synthesis Route of 1-(3,4-Methylenedioxyphenyl)-2-Propanone (MDP-2-P) Based on Impurity Profiles of MDMA," Forensic Science International, 2005, pp. 181-192, vol. 149.
Tiecco et al., "Selenium-Promoted Synthesis of Enantiornerically Pure Substituted Morpholines Starting From Alkenes and chiral Aminoalcohols," Tetrahedron: Asymmetry, 2003, pp. 2651-2657, vol. 14.
Van Vliet et al., "Synthesis and Pharmacological Evaluation of Thiopyran Analogues of the Dopamine D$_3$ Receptor-Selective Agonist (4aR,10bR)-(+)-trans-3,4,4a,10b-Tetrahydro-4-n-propyl-2H,5H-[1]Benzopyrano[4,3-b]-1,4-Oxazin-9-ol (PD 128907)," J. Med. Chem., 2000, pp. 2871-2882, vol. 43.
Wee et al., "Relationship Between the Serotonergic Actifity and Reinforcing Effects of a Series of Amphetamine Analogs," The Journal of Pharmacology and Experimental Therapeutics, 2005, pp. 848-854, vol. 313, No. 2.
Kafka et al., Syntheses of 3-aminoquinoline-2,4(1H,3H)-diones, Heterocycles, 2002, vol. 57, No. 9, pp. 1659-1682.
Talaty et al., The reaction of α—lactams with Grignard reagents: A correction of the literature, Tetrahedron Letters, 1976, vol. 52, pp. 4797-4800.
Boswell et al, "Synthesis and Anti-tetravenazine Activity of C-3 Analogues of Dimethyl-2-phenylmorpholines," J. Heterocyclic Chemistry, 1996, vol. 33 (1), p. 33-9.
Carroll et al., "Synthesis and Biological Evaluation of Bupropion Analogues as Potential Pharmacotherapies for Smoking Cessation," J. Medicinal Chem., 2010, vol. 53 (5) pp. 2204-2214.
Hu et al., "Synthesis of 2-Aryl-3,5,5-trimethyl-2-morpholinols Hydrochloride," Chinese Journal of Applied Chemistry, 2005, vol. 22, No. 3, pp. 343-345.
Cao et al., "Asymmetric Synthesis, Crystal Structure, and Antidepressant Activity of 2-aryl-3-alkyl-5-methyl-2-morpholinol Hydrochlorides," Can. J. Chem. 2007, vol. 85, pp. 29-36.
Ritzen et al., "Enantioselecive Chemoenzymatic Synthesis of cis- and trans-2,5-Disubstituted Morpholines," J. Org. Chem., 2010, vol. 75, pp. 3461-3464.
Arellano et al., "Validation of a Liquid Chromatography-Mass Spectrometry Method to Assess the Metabolism of Bupropion in Rat Everted Gut Sacs," Journal of Cromatography B, 2005, 829(1-2), pp. 50-55.
Boswell et al., "Synthesis, Stereochemistry and Anti-tetrabenazine Activity of Bicyclo Analogues of 2-Phenylmorpholines [1]," Journal of Heterocyclic Chemistry, 1997, 34(6), pp. 1813-1820.
Bouron et al., "Stereoselective Synthesis of 2,6-Disubstituted Morpholines from Chiral Non-Racemic Lactams," Tetrahedron Letters, 1999, 40(40), pp. 7227-7230.
Benott-Guyod et al., "Dérivés de l'acide dipropylacétique, III. Noueaux amides et esters," Chimica Therapeutica, 1968, No. 5, pp. 336-342.
Hu et al., "Synthesis and Characterization of 2-Arylmorpholine Hydrochloride," Journal of Hunan University (Natural Sciences), 2005, vol. 32, No. 4, pp. 72-76.
Kelley et al., "(2S,3S,5R)-2-(3,5-Difluorophenyl)-3,5-dimethyl-2-morpholinol: A Novel Antidepressant Agent and Selective Inhibitor of norepinephrine Uptake," Journal of Medication Chemistry, 1996, 39(2), pp. 347-349.
Larsen et al., "Design and Application of Prodrugs," Textbook of Drug Design and Discovery, 2002, Chapter 14, pp. 460-514.
Musso et al., "Design and Synthesis of a Chiral Hapten for a Radioimmunoassay of the Antidepressant (2S, 3S, 5R)-2-(3,5-Difluorophenyl)-3,5-dimethyl-2-morpholinol Hydrochloride," Tetrahedron: Asymmetry, 1995, 6(8), pp. 1841-1844.
Wermuth et al., "Designing Prodrugs and Bioprecursors," The Practice of Medication Chemistry (Third Edition), 2008, Chapter 36, pp. 721-746.
Xiao et al., "Synthesis and biological activity of 2-aryl-5-benyl-3-methyl-2-orpholinol hydrochloride," Chinese Journal of New Drugs, 2006, vol. 15, No. 13, pp. 1089-1092.
Registry (STN) [online], Jan. 20, 2009, (Searched Date: Mar. 4, 2015) CAS:1094485-98-9.

(56) References Cited

OTHER PUBLICATIONS

Registry (STN) [online], Sep. 9, 2009, (Searched Date: Mar. 4, 2015) CAS: 1181632-24-5.
Registry (STN) [online], Feb. 2, 2009, (Searched Date: Mar. 4, 2015) CAS: 1099679-87-4.
Registry (STN) [online], Feb. 2, 2009, (Searched Date: Mar. 4, 2015) CAS: 1099679-83-0.
Registry (STN) [online], Feb. 2, 2009, (Searched Date: Mar. 4, 2015) CAS: 1099679-71-6.
Registry (STN) [online], Feb. 2, 2009, (Searched Date: Mar. 4, 2015) CAS: 1099679-67-0.
Registry (STN) [online], Feb. 2, 2009, (Searched Date: Mar. 4, 2015) CAS: 1099655-59-0.
Registry (STN) [online], Feb. 2, 2009, (Searched Date: Mar. 4, 2015) CAS: 1099623-67-2.
Registry (STN) [online], Jan. 21, 2009, (Searched Date: Mar. 4, 2015) CAS: 1094762-30-7.
Registry (STN) [online], Jan. 20, 2009, (Searched Date: Mar. 4, 2015) CAS: 1094486-00-6.
Registry (STN) [online], Dec. 20, 2009, (Searched Date: Mar. 4, 2015) CAS: 800365-04-2.
Registry (STN) [online], Jan. 30, 2009, (Searched Date: Mar. 4, 2015) CAS: 1097796-78-5.
Registry (STN) [online], Jan. 30, 2009, (Searched Date: Mar. 4, 2015) CAS: 1097796-73-0.
Registry (STN) [online], Jan. 21, 2009(Searched Date: Mar. 4, 2015) CAS: 1094649-71-4.
Bundgaard, "Novel Chemical Approaches in Prodrug Design," *Drugs of the Future*, 1991, vol. 16, No. 5, pp. 443-458.
Rothmann et al., "Therapeutic Potential of Monoamine Transporter Substates," *Current Topics in Medicinal Chemistry*, 2006, vol. 6, pp. 1845-1859. http://www.ncbi.nlm.nih.gov/pubmed/17017961.

\* cited by examiner

PHENYLMORPHOLINES AND ANALOGUES THEREOF

CROSS-REFERENCE TO RELATED APPLICATIONS

The present application is a national stage entry of PCT International Application No. PCT/US2011/037361, filed May 20, 2011, which claims the benefit of U.S. Provisional Application No. 61/347,259, filed May 21, 2010.

FEDERALLY SPONSORED RESEARCH OR DEVELOPMENT

This invention was made with United States Government support under DA 12970/0207690.000 awarded by the National Institutes of Health. The United States Government has certain rights in the invention.

FIELD OF THE INVENTION

The present application is directed to various compounds and methods of preparation of compounds that are capable of functioning as releasers and/or reuptake inhibitors of one or more monoamine neurotransmitters, including dopamine, serotonin, and norepinephrine. The application is also directed to pharmaceutical compositions comprising one or more of these compounds, which may also comprise one or more additional therapeutic agents. It is also directed to methods of treatment of various conditions that may be responsive to modification of monoamine neurotransmitter levels, such as pre-obesity, obesity, addiction, and depression.

BACKGROUND OF THE INVENTION

Obesity is a serious public health concern, associated with a number of health conditions. The National Center for Health Statistics reports that 65% of adults are considered to be overweight (pre-obese), with greater than 34% of those adults considered to be obese. The incidences of obesity have dramatically increased over the last twenty years, with the percentage of obese adults having doubled from 1980 to 2004. Children are at risk as well, with an estimated 17% of children from age 2-19 classified as obese. Medical conditions commonly associated with obesity include diabetes and high blood pressure, which may lead to cardiovascular disease, stroke, and premature mortality.

As a result, there has been an increase in demand for medications to treat pre-obesity and obesity. One type of medication that is available to treat obesity is anorectics, also known as appetite suppressants. One well-known anorectic is Fen-Phen, which was widely prescribed for weight loss in the early 1990s. Fen-Phen is a combination drug that comprises two compounds; namely, fenfluramine and phentermine. Fenfluramine acts via a serotonergic mechanism to increase a user's satiety. Phentermine has a stimulant effect, acting mainly through dopaminergic and noradrenergic mechanisms to decrease a user's appetite. Fen-Phen, although effective in the treatment of obesity, was linked to possible valvular heart disease and pulmonary hypertension in 1997. As a result, fenfluramine and the Fen-Phen combination drug were pulled from the market in 1997.

It is thought that the valvular heart disease and pulmonary hypertension associated with the use of fenfluramine and its active metabolite norfenfluramine may result from the stimulation of 5-hydroxytryptamine (5-HT) serotonin receptors. Studies have shown that, in particular, fenfluramine is a potent agonist of a particular type of 5-HT receptor, the $5\text{-}HT_{2B}$ receptor, which is present in human cardiac valves. Phentermine is still available in many countries, including the United States; however, it is classified as a controlled substance due to its chemical and pharmacological similarity to amphetamines. One concern with such compounds is the high potential for abuse.

Another anorectic, which was prescribed for the short-term treatment of obesity, is phenmetrazine Phenmetrazine is reportedly a potent substrate for norepinephrine and dopamine transporters and displays stimulant properties similar to those of amphetamines. Some reports indicate that phenmetrazine has been widely abused as a recreational drug and has greater addiction potential than amphetamines. Because of phenmetrazine's high potential for abuse, it was pulled from the market.

Subsequently, phendimetrazine, a close analogue of phenmetrazine with a methyl substituent on the amine, was released onto the market as an anorectic. Recent research has suggested that phendimetrazine actually exerts its effect via conversion to phenmetrazine. See Rothman et al., *Eur. J. Pharmacology* 447: 51-57 (2002), incorporated herein by reference. Thus, as with phenmetrazine, phendimetrazine also has a high potential for abuse. Although it is still available for the treatment of obesity, phendimetrazine is a Class III controlled substance and there is a high likelihood of abuse of this drug.

Accordingly, there is a need for an anorectic drug that acts similarly to the aforementioned drugs on the central nervous system, but does not provide such high potential for abuse and/or does not act as an agonist of the $5\text{-}HT_{2B}$ receptor. Because of their effects on the central nervous system, such compounds may be useful not only for treating obesity and pre-obesity, but also for other diseases related to the central nervous system including addiction, depression, and anxiety.

BRIEF SUMMARY OF THE INVENTION

The present invention relates generally to compounds and prodrugs that may be useful as releasers and/or reuptake inhibitors of one or more monoamine neurotransmitters, including dopamine, serotonin, and norepinephrine. It also relates to pharmaceutical formulations of such compounds and/or prodrugs and to methods of using such compounds, prodrugs, or formulations thereof to treat various conditions that may be responsive to the modulation of neurotransmitter levels.

In one aspect, the present invention provides a compound that may modulate the levels of one or more monoamine neurotransmitters. In some embodiments, the invention provides a compound according to the following structure:

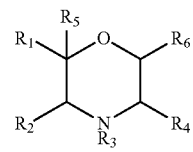

wherein:
$R_1$ is optionally substituted aryl;
$R_2$ is H or optionally substituted C1-3 alkyl;
$R_3$ is H, optionally substituted C1-3 alkyl, or benzyl;

$R_4$ is H or optionally substituted C1-3 alkyl; and
$R_5$ is H or OH;
$R_6$ is H or optionally substituted C1-3 alkyl;
with the proviso that when $R_2$ is $CH_3$ and $R_1$ is phenyl, then (a) the phenyl ring of $R_1$ is substituted with one or more substituents; or (b) $R_3$ is substituted C1 alkyl or optionally substituted C2-C3 alkyl, or (c) one or more of $R_4$, $R_5$, and $R_6$ is not H, or a combination of two or more of (a) through (c); or a pharmaceutically acceptable ester, amide, salt, solvate, prodrug, or isomer thereof.

In certain embodiments, a compound of the structure above is provided, wherein $R_1$ is phenyl, substituted phenyl, naphthyl, or substituted naphthyl. In some embodiments, $R_1$ is a substituted aryl group (e.g., a substituted phenyl) and $R_3$ is H.

In some embodiments, a compound is provided having the structure:

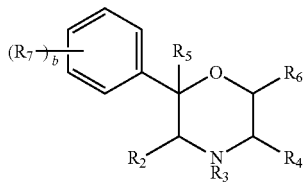

wherein the substituents are as noted above, except that:
each $R_7$ represents a substituent independently selected from the group consisting of OH, optionally substituted C1-4 alkyl, optionally substituted C1-4 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OH$, $CH_2OR_{12}$, $NR_{12}R_{13}$, $NHCOR_{12}$, $NHCO_2R_{12}$, $CONR_{12}R_{13}$, C1-3 alkylthio, $R_{12}SO$, $R_{12}SO_2$, $CF_3S$, and $CF_3SO_2$, wherein $R_{12}$ and $R_{13}$ are each independently selected from H or optionally substituted C1-10 alkyl; and
b is an integer from 0-5;
with the proviso that when $R_2$ is $CH_3$, then (a) b is an integer from 1-5, or (b) $R_3$ is substituted C1 alkyl or optionally substituted C2-C3 alkyl, or (c) one or more of $R_4$, $R_5$, and $R_6$ is not H, or a combination of two or more of (a) through (c),
or a pharmaceutically acceptable ester, amide, salt, solvate, prodrug, or isomer thereof In certain embodiments, a compound of the above formula is provided, wherein b is an integer from 1-5, and each $R_7$ is independently selected from the group consisting of optionally substituted C1-4 alkyl, optionally substituted C1-4 alkoxy, halo, OH, CN, and $CF_3$. In some embodiments, b is 1 and the $R_7$ substituent is located meta or para to the morpholine substituent on the phenyl ring.

In some embodiments, a compound is provided having the structure:

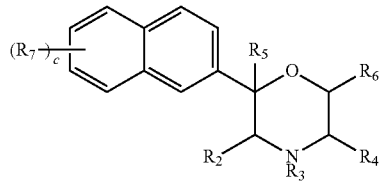

wherein:
each $R_7$ represents a substituent independently selected from the group consisting of OH, optionally substituted C1-4 alkyl, optionally substituted C1-3 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OH$, $CH_2OR_{12}$, $NR_{12}R_{13}$, $NHCOR_{12}$, $NHCO_2R_{12}$, $CONR_{12}R_{13}$, C1-3 alkylthio, $R_{12}SO$, $R_{12}SO_2$, $CF_3S$, and $CF_3SO_2$; and
c is an integer from 0-7,
or a pharmaceutically acceptable ester, amide, salt, solvate, prodrug, or isomer thereof.

In some embodiments of the present invention, a compound is provided, wherein $R_2$ is H or $CH_3$. In some embodiments of the invention, a compound is provided wherein $R_4$ is H or $CH_3$. In certain embodiments, $R_4$ is optionally substituted C1-3 alkyl. In certain embodiments, one of $R_2$ and $R_4$ is H and the other of $R_2$ and $R_4$ is optionally substituted C1-3 alkyl. In some embodiments, such compounds may comprise an enantiomeric excess of at least 95% of one isomer (e.g., the (2S-5S) enantiomer).

In one embodiment of the invention, certain compounds are provided, selected from the group consisting of: 2-(2'-naphthyl)morpholine; 2-methyl-6-phenyl-morpholine; 2-(3-chloro-phenyl)-3-methyl-morpholine; 2-(3-chloro-phenyl)-3-methyl-morpholin-2-ol; 2-(3-chloro-phenyl)-5-methyl-morpholine; 2-(3-chloro-phenyl)-6-methyl-morpholine; 2-(3-fluoro-phenyl)-3-methyl-morpholine; 2-(3-fluoro-phenyl)-3-methyl-morpholin-2-ol; 2-(3-fluoro-phenyl)-5-methyl-morpholine; 2-(3-methoxy-phenyl)-5-methyl-morpholine; 2-(4-fluorophenyl)morpholine; 2-(4-chloro-phenyl)-5-methyl-morpholine; 2-(4-fluoro-phenyl)-5-methyl-morpholine; 3-methyl-2-phenylmorpholin-2-ol; 3-methyl-2-(2'-naphthyl)morpholine; 3-methyl-2-(3'-tolyl)morpholine; 3-methyl-2-(3'-tolyl)morpholin-2-ol; 3-methyl-2-(4'-tolyl)morpholine; 3-methyl-[(4'-fluoro)-2-phenyl]morpholine; 3-methyl-[(4'-chloro)-2-phenyl]morpholine; 3-methyl-[(4'-methoxy)-2-phenyl]morpholine; 3-methyl-[(4'-cyano)-2-phenyl]morpholine; 3-methyl-[(3'-hydroxy)-2-phenyl]morpholine; 3-methyl-[(3'-methoxy)-2-phenyl]morpholine; 3-methyl-[(3'-cyano)-2-Phenyl]morpholine; 3-methyl-[(3',4'-dichloro)-2-phenyl]morpholine; 3-methyl-[(3'-chloro-4'-fluoro)-2-Phenyl]morpholine; 3-methyl-[(3'-chloro-4'-methyl)-2-Phenyl]morpholine; 5-methyl-2-(3-trifluoromethyl-phenyl)-morpholine; 5-methyl-2-p-tolyl-morpholine; 5-methyl-2-m-tolyl-morpholine; 5-methyl-2-phenyl-morpholine; 5-methyl-2-(4-trifluoromethyl-phenyl)-morpholine, or a pharmaceutically acceptable ester, amide, salt, solvate, prodrug, or isomer thereof.

According to the invention, in some embodiments, the compound is one or more of a dopamine releaser, norepinephrine releaser, serotonin releaser, dopamine uptake inhibitor, norepinephrine uptake inhibitor, and serotonin uptake inhibitor. In certain embodiments, the compound is a dopamine releaser or a dual serotonin and dopamine releaser. In some embodiments, the compound is inactive at the $5HT_{2B}$ receptor.

In another aspect of the invention is provided a prodrug of the compounds disclosed herein, comprising a compound having $R_3$ replaced with a labile protecting group. For example, certain prodrugs of the present invention have the following formula:

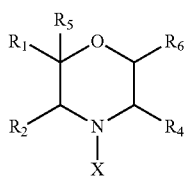

wherein:
X is a chemical moiety which, when the prodrug is administered in vivo, is cleaved in whole or in part to provide a free amine on the morpholine ring;

In some specific embodiments, a prodrug according to this structure is provided, wherein X is an amino acid or peptide.

In some embodiments, a prodrug is provided having the formula:

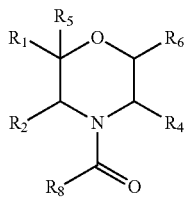

wherein $R_8$ is optionally substituted C1-10 alkyl, optionally substituted C1-10 alkoxy, optionally substituted phenyl, optionally substituted benzyl, or optionally substituted pyridyl.

In a further aspect of the invention, a pharmaceutical composition is provided, wherein the composition comprises a compound or prodrug as disclosed herein and one or more pharmaceutically acceptable carriers.

In a still further aspect of the invention, a method for treating or delaying the progression of disorders that are alleviated by modulating monoamine release in a patient comprising administering a therapeutically effective amount of at least one compound or prodrug as disclosed herein is provided. For example, in certain embodiments, the disorder is selected from the group consisting of addiction, depression, obesity, bipolar disorder, attention deficit disorder (ADD), attention deficit/hyperactivity disorder (ADHD), hypoactive sexual desire disorder, antidepressant-induced sexual dysfunction, orgasmic dysfunction, seasonal affective disorder/winter depression, mania, bulimia and other eating disorders, panic disorders, obsessive compulsive disorder, schizophrenia, schizo-affective disorder, Parkinson's disease, narcolepsy, anxiety disorders, insomnia, chronic pain, migraine headaches, and restless legs syndrome.

DETAILED DESCRIPTION OF THE INVENTION

The present invention now will be described more fully hereinafter with reference to the accompanying figures, in which some, but not all embodiments of the inventions are shown. Indeed, these inventions may be embodied in many different focus and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

Many modifications and other embodiments of the inventions set forth herein will come to mind to one skilled in the art to which these inventions pertain having the benefit of the teachings presented in the foregoing description. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention provides compounds that may function to modify the release and/or reuptake of one or more monoamine neurotransmitters selected from dopamine, norepinephrine, and serotonin. The invention also provides methods of preparation and pharmaceutical compositions thereof. It also provides methods for using such compounds to treat a variety of disorders that may be responsive to the modulation of one or more of these neurotransmitters. In particular, the compositions and methods can be used in the treatment of obesity, various drug addictions, and depression. In some embodiments, treatment can comprise the use of a compound of the present invention as a single active agent. In other embodiments, treatment can comprise the use of a compound of the present invention in combination with one or more further active agents. The specific pharmaceutical composition (or compositions) used in the invention and the methods of treatment provided by the invention are further described below.

DEFINITIONS

The term "alkyl" as used herein means saturated straight, branched, or cyclic hydrocarbon groups. In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), 1 to 4 carbon atoms ("C1-4 alkyl"), or 1 to 3 carbon atoms ("C1-3 alkyl"). In other embodiments, alkyl refers to groups comprising 3-10 carbon atoms ("C3-10 alkyl"), 3-8 carbon atoms ("C3-8 alkyl"), or 3-6 carbon atoms ("C3-6 alkyl"). In specific embodiments, alkyl refers to methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. Substituted alkyl refers to alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 2 to 10 carbon atoms ("C2-10 alkenyl"). In further embodiments, alkenyl refers to groups comprising 2 to 8 carbon atoms ("C2-8 alkenyl"), 2 to 6 carbon atoms ("C2-6 alkenyl"), or 2 to 4 carbon atoms ("C2-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 2 to 10 carbon atoms ("C2-10 alkynyl"). In further embodiments, alkynyl refers to groups comprising 2 to 8 carbon atoms ("C2-8 alkynyl"), 2 to 6 carbon atoms ("C2-6 alkynyl"), or 2 to 4 carbon atoms ("C2-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The term "aryl" as used herein means a stable monocyclic, bicyclic, or tricyclic carbon ring of up to 8 members in each ring, wherein at least one ring is aromatic as defined by the Hückel 4n+2 rule. Exemplary aryl groups according to the invention include phenyl and naphthyl.

The term "halo" or "halogen" as used herein means fluorine, chlorine, bromine, or iodine.

The term "alkylthio" as used herein means a thio group with one or more alkyl substituents, where alkyl is defined as above.

The term "acylamido" refers to an amide group with one or more acyl substituents, where acyl is as defined below.

The term "acyl" as used herein means a group formed by removing the hydroxyl group from a carboxylic acid, in which the non-carbonyl moiety of the group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with halogen, C1-6 alkyl or C1-6 alkoxy; sulfonate esters such as alkyl or aralkyl sulfonyl including methanesulfonyl; mono-, di-, or triphosphate ester; trityl or monomethoxytrityl; substituted benzyl; trialkylsilyl such as dimethyl-t-butylsilyl or diphenylmethylsilyl.

The terms "aralkyl" and "arylalkyl" as used herein mean an aryl group as defined above linked to the molecule through an alkyl group as defined above.

The term "amino" as used herein means a moiety represented by the structure $NR_2$, and includes primary amines, and secondary and tertiary amines substituted by alkyl (i.e., alkylamino). Thus, $R_2$ may represent two hydrogen atoms, two alkyl moieties, or one hydrogen atom and one alkyl moiety.

The term "cycloalkyl" means a non-aromatic, monocyclic or polycyclic ring comprising carbon and hydrogen atoms. Substituted cycloalkyl refers to alkyl substituted with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "analogue" as used herein means a compound in which one or more individual atoms or functional groups have been replaced, either with a different atom or a different functional, generally giving rise to a compound with similar properties.

The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "prodrug" as used herein means any compound which, when administered to a mammal, is converted in whole or in part to a compound of the invention.

The term "active metabolite" as used herein means a physiologically active compound which results from the metabolism of a compound of the invention, or a prodrug thereof, when such compound or prodrug is administered to a mammal The terms "therapeutically effective amount" or "therapeutically effective dose" as used herein are interchangeable and mean a concentration of a compound according to the invention, or a biologically active variant thereof, sufficient to elicit the desired therapeutic effect according to the methods of treatment described herein.

The term "pharmaceutically acceptable carrier" as used herein means a carrier that is conventionally used in the art to facilitate the storage, administration, and/or the healing effect of a biologically active agent.

The term "intermittent administration" as used herein means administration of a therapeutically effective dose of a composition according to the invention, followed by a time period of discontinuance, which is then followed by another administration of a therapeutically effective dose, and so forth.

The term "neurotransmitter" as used herein encompasses monoamine neurotransmitters and neuromodulators. In particular, the term neurotransmitter as used herein includes, but is not limited to, dopamine, norepinephrine, and serotonin.

Active Agents

The present invention provides compounds, methods of preparation of the compounds, pharmaceutical compositions, and methods of treatment of various conditions using such compounds and pharmaceutical compositions.

In some embodiments, morpholine compounds according to Formula I are provided,

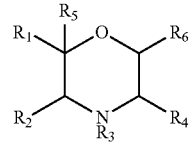

Formula I wherein:
$R_1$ is optionally substituted aryl (e.g., naphthyl or phenyl);
$R_2$ is H or optionally substituted C1-3 alkyl;
$R_3$ is H, optionally substituted C1-3 alkyl, or benzyl;
$R_4$ is H or optionally substituted C1-3 alkyl;
$R_5$ is H or OH; and
$R_6$ is H or optionally substituted C1-3 alkyl;
with the proviso that when $R_2$ is $CH_3$ and $R_1$ is phenyl, then (a) the phenyl ring of $R_1$ is substituted with one or more substituents; or (b) $R_3$ is substituted Cl alkyl or optionally substituted C2-C3 alkyl, or (c) one or more of $R_4$, $R_5$, and $R_6$ is not H, or a combination of two or more of (a) through (c);

or a pharmaceutically acceptable ester, amide, salt, solvate, prodrug, or isomer thereof.

In some preferred embodiments, a compound of Formula I is provided wherein $R_1$ is aryl substituted at one or more available sites. Where multiple substitutions are present on $R_1$, multiple different types of substituents may be utilized. The one or more substituents present on $R_1$ may include, but are not limited to, OH, optionally substituted C1-4 alkyl, optionally substituted C1-4 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OH$, $CH_2OR_{12}$, $NR_{12}R_{13}$, $NHCOR_{12}$, $NHCO_2R_{12}$, $CONR_{12}R_{13}$, C1-3 alkylthio, $R_{12}SO$, $R_{12}SO_2$, $CF_3S$, and $CF_3SO_2$, wherein $R_{12}$ and $R_{13}$ are each independently selected from H or optionally substituted C1-10 alkyl.

In some preferred embodiments, a compound of Formula I is provided wherein $R_2$ is H. In some preferred embodiments, a compound of Formula I is provided wherein $R_2$ is C1-3 alkyl (e.g., $CH_3$). In some preferred embodiments, a compound of Formula I is provided wherein $R_3$ is H. In some preferred embodiments, a compound of Formula I is provided wherein $R_4$ is H. In some preferred embodiments, a compound of Formula I is provided wherein $R_4$ is C1-3 alkyl (e.g., $CH_3$). In some preferred embodiments, a compound of Formula I is provided wherein $R_5$ is H. In some preferred embodiments, a compound of Formula I is provided wherein $R_5$ is OH. In one particular embodiment, the compound of Formula I may be represented by Formula II.

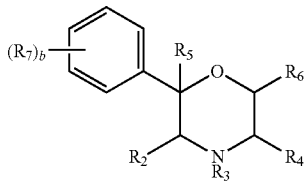

Formula II wherein:
$R_2$ is H or optionally substituted C1-3 alkyl;
$R_3$ is H, optionally substituted C1-3 alkyl, or benzyl;
$R_4$ is H or optionally substituted C1-3 alkyl;
$R_5$ is H or OH;
$R_6$ is H or optionally substituted C1-3 alkyl;
each $R_7$ represents a substituent independently selected from the group consisting of OH, optionally substituted C1-4 alkyl, optionally substituted C1-4 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OH$, $CH_2OR_{12}$, $NR_{12}R_{13}$, $NHCOR_{12}$, $NHCO_2R_{12}$, $CONR_{12}R_{13}$, C1-3 alkylthio, $R_{12}SO$, $R_{12}SO_2$, $CF_3S$, and $CF_3SO_2$, wherein $R_{12}$ and $R_{13}$ are each independently selected from H or optionally substituted C1-10 alkyl;
b is an integer from 0-5; and
with the proviso that when $R_2$ is $CH_3$, then (a) b is an integer from 1-5, or (b) $R_3$ is substituted C1 alkyl or optionally substituted C2-C3 alkyl, or (c) one or more of $R_4$, $R_5$, and $R_6$ is not H, or a combination of two or more of (a) through (c), or a pharmaceutically acceptable ester, amide, salt, solvate, prodrug, or isomer thereof.

In some preferred embodiments, b=0 or 1. In certain embodiments, b=1 and $R_7$ is selected from the group consisting of $CH_3$, F, and Cl. In certain embodiments, the $R_7$ substituent is located meta or para to the morpholine substituent on the phenyl ring.

In another particular embodiment, the compound of Formula I may be represented by Formula III:

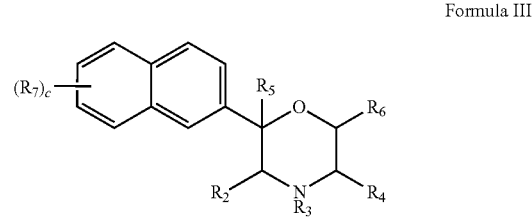

Formula III wherein:
$R_2$ is H or optionally substituted C1-3 alkyl;
$R_3$ is H, optionally substituted C1-3 alkyl, or benzyl;
$R_4$ is H or optionally substituted C1-3 alkyl;
$R_5$ is H or OH;
$R_6$ is H or optionally substituted C1-3 alkyl;
each $R_7$ represents a substituent independently selected from the group consisting of OH, optionally substituted C1-4 alkyl, optionally substituted C1-3 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OH$, $CH_2OR_{12}$, $NR_{12}R_{13}$, $NHCOR_{12}$, $NHCO_2R_{12}$, $CONR_{12}R_{13}$, C1-3 alkylthio, $R_{12}SO$, $R_{12}SO_2$, $CF_3S$, and $CF_3SO_2$; and
c is an integer from 0-7,
or a pharmaceutically acceptable ester, amide, salt, solvate, prodrug, or isomer thereof.

In some embodiments of the present invention, therapeutically inactive prodrugs are provided. Prodrugs are compounds which, when administered to a mammal, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. In preferred embodiments, the nitrogen atom of the morpholine in Formulas I-III above is functionalized with such a chemical moiety. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, may reduce polarity and allow for the compound's passage into cells. The means by which the modification of one or more heteroatoms of the compound is performed may vary, and typical methods for such modifications are familiar to one of skill in the art of organic synthesis. For example, general reaction conditions for the alkylation and acylation of heteroatoms are well known and can be modified for application to the compounds provided herein.

In some prodrug embodiments, the amine of the morpholine ring of any one of Formulas I-III is modified to provide a prodrug. Examples of substituent groups that can replace one or more hydrogen atoms on the free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine. Any of these moieties can be used in combination with the disclosed active agents to achieve a desired effect.

Prodrugs may be particularly useful according to the present invention, as they may provide a safer alternative for treatment due to the noted high potential for abuse of amphetamines and related compounds. Although the therapeutic effect of the prodrugs may be similar to that provided by the free compounds, the prodrugs of the present invention may be stable under conditions commonly used to provide drugs in concentrated form for illicit use. Specifically, using a prodrug should reduce the risk that pills comprising the prodrug might be used to extract the drug and concentrate it or use it via other methods (e.g., via intravenous administration, snorting, or smoking), because additional steps (i.e., for example, acid cleavage and extraction) are required to provide the prodrug compound in the pure drug form. Additionally, a prodrug form may be advantageous in that it may deliver a constant low dose of the drug which reduces abuse liability by "slow onset," i.e., a pharmacokinetics approach.

Prodrugs of the present invention may be represented by Formula IV:

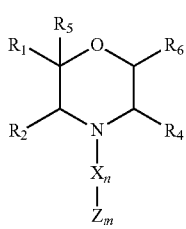

Formula IV wherein:
$R_1$, $R_2$, $R_4$, $R_5$, and $R_6$ are the same as indicated above for Formula I;
X is a chemical moiety, wherein each X may be the same or different;
n is an integer from 0 to 50, preferably 1 to 10;
Z is a chemical moiety that acts as an adjuvant, wherein each Z may be the same or different, and wherein each Z is different from at least one X; and
m is an integer from 0 to 50.

In some embodiments, X may be alkyl. In some embodiments, when $R_2$ is $CH_3$, $R_1$ is phenyl, $R_4$-$R_6$ are H, n=1, and m=0, X is not $CH_3$. In some, but not all, embodiments of Formula IV, when $R_1$ is phenyl, the phenyl ring is substituted with one or more substituents and/or one or more of $R_4$, $R_5$, and $R_6$ is not H.

The chemical moiety constituting X may be any chemical moiety that, while bound to the compound, decreases the pharmacological activity of the compound in comparison to the free compound. In some embodiments, X is any pharmaceutically acceptable chemical moiety which, when the prodrug is administered in vivo, is cleaved in whole or in part to provide a free amine on the morpholine ring. Exemplary chemical moieties include, but are not limited to, peptides, carbohydrates (including sugars), lipids, nucleosides, nucleic acids, and vitamins, aryl groups; steroids; 1,2-diacylglycerol; alcohols; optionally substituted acyl groups (including lower acyl); optionally substituted alkyl groups (including lower alkyl); sulfonate esters (including alkyl or arylalkyl sulfonyl, such as methanesulfonyl and benzyl, wherein the phenyl group is optionally substituted with one or more substituents as provided in the definition of an aryl given herein); optionally substituted arylsulfonyl groups; lipids (including phospholipids); phosphotidylcholine; phosphocholine; amino acid residues or derivatives; amino acid acyl residues or derivatives; cholesterols; or other pharmaceutically acceptable leaving groups which, when administered in vivo, provide the free amine and/or carboxylic acid moiety. Peptides include dipeptides, tripeptides, oligopeptides, and polypeptides.

In some preferred embodiments, X is an amino acid. Where X is an amino acid or peptide, the amino acid(s) may be naturally occurring or unnatural, non-standard, or synthetic, and may be either the L- or D enantiomer. Particularly preferable amino acids for use in the present invention include alanine, lysine, serine, phenylalanine, arginine, glycine, glutamic acid, or leucine. In some preferred embodiments of the invention, a prodrug of Formula IV is provided, wherein m=0. In some preferred embodiments of the invention, a prodrug of Formula IV is provided, wherein X is a single amino acid. In other preferred embodiments, a prodrug of Formula IV is provided, wherein X is a peptide.

With regard to peptide conjugates, an iterative approach can be used to identify favorable conjugates by synthesizing and testing single amino acid conjugates and subsequently extending the peptide by one amino acid at a time. The parent single amino acid prodrug candidate may exhibit more or less desirable characteristics than the subsequent di- or tri-, etc. peptide candidates. The iterative approach can be beneficial in determining whether peptide length influences bioavailability.

In some other embodiments, X may be represented by the following:

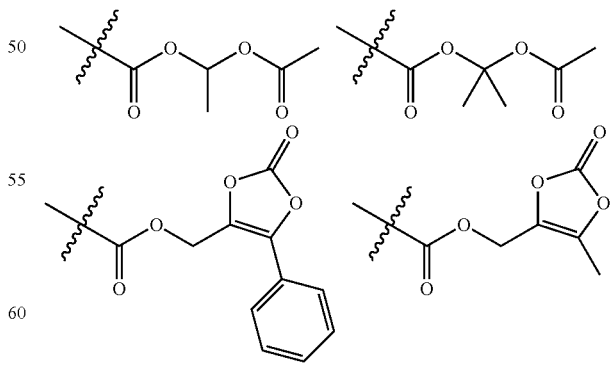

As noted, Z may be a chemical moiety that acts as an adjuvant. Exemplary chemical moieties that may comprise Z include those indicated for X, above (e.g., peptides, amino acids, carbohydrates, vitamins) Further examples of Z may be found, for example, in U.S. Patent Application Publication 2009/0192093 to Mickle et al., incorporated by reference herein in its entirety.

In preferred embodiments, m=0, which is represented by Formula V:

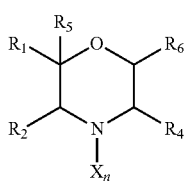

Formula V wherein the substituents are the same as those indicated for Formula IV.

In preferred embodiments, when $R_2$ is $CH_3$, $R_1$ is phenyl, $R_4$-$R_6$ are H, and n=1, X is not $CH_3$.

In some preferred embodiments, prodrugs of the present invention may be represented by the following formula:

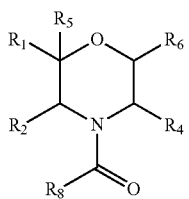

Formula VI wherein the substituents are the same as those indicated for Formula IV, except that:

$R_8$ is optionally substituted C1-10 alkyl, optionally substituted C1-10 alkoxy, optionally substituted phenyl, optionally substituted benzyl, or optionally substituted pyridyl. For example, in certain embodiments, $R_8$ may be, but is not limited to, $CH_3$, $CH_2CH_3$, phenyl, benzyl, 4-$CH_2$NPh, 3-pyridyl, $OCH_3$, $OCH_2CH_3$, $(CH_2)_3N(CH_3)_2$, $(CH_2)_3N^+(CH_3)_3$, $O(CH_2)NH_2$, $O(CH_2)_3N(CH_3)_2$, and $O(CH_2)_3N+(CH_3)_2$, or any of the following:

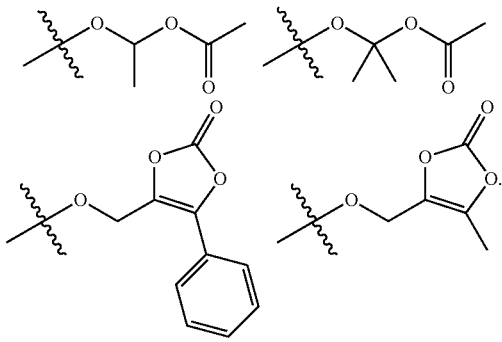

In some embodiments, compounds or prodrugs with one or more chiral centers are provided. While racemic mixtures of compounds or prodrugs of the invention may be active, selective, and bioavailable, isolated isomers may be of interest as well.

The compounds and prodrugs disclosed herein as active agents may contain chiral centers, which may be either of the (R) or (S) configuration, or which may comprise a mixture thereof. Accordingly, the present invention also includes stereoisomers of the compounds and prodrugs described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds and prodrugs of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

The compounds of the present invention may be compounds according to Formulas I-III with one or more chiral centers, which may be either of the (R) or (S) configuration, or which may comprise a mixture thereof. The carbon to which $R_1$ and $R_5$ are connected may be either of the R or S configuration. When $R_2$ is a substituent other than H, the carbon to which $R_2$ is connected is a chiral center and may be either of the R or S configuration. When $R_4$ is a substituent other than H, the carbon to which $R_2$ is connected to is a chiral center and may be either of the R or S configuration. When $R_6$ is a substituent other than H, the carbon to which $R_6$ is connected is a chiral center and may be either of the R or S configuration. The present invention includes both racemic mixtures of a compound of Formula I and isolated isomers of Formulas I-III. Where more than one chiral center is present in a compound of the invention, some, none, or all of the chiral centers may be enantiomerically enriched. Thus, mixtures of a compound of Formulas I-III may be racemic with respect to one or more chiral centers and/or enantiomerically enriched with respect to one or more chiral centers.

In some preferred embodiments, an enantiomerically enriched sample of a compound of Formulas I-III is provided wherein the carbon to which $R_1$ and $R_5$ are attached is (R) or (S). In some preferred embodiments, an enantiomerically enriched sample of a compound of Formulas I-III is provided wherein the carbon to which $R_2$ is attached is (R) or (S). In some preferred embodiments, an enantiomerically enriched sample of a compound of Formulas I-III is provided wherein the carbon to which $R_4$ is attached is (R) or (S). In some preferred embodiments, an enantiomerically enriched sample of a compound of Formulas I-III is provided wherein the compound to which $R_6$ is attached is (R) or (S). In some preferred embodiments, an enantiomerically enriched sample of a compound of Formulas I-III is provided wherein both the carbon to which $R_1$ and $R_5$ is attached and the carbon to which $R_2$ is attached are independently (R) or (S) (e.g., (R, S), (S, R), (R, R), or (S, S)). In some preferred embodiments, an enantiomerically enriched sample of a compound of Formulas I-III is provided wherein both the carbon to which $R_1$ and $R_5$ is attached and the carbon to which $R_4$ is attached are independently (R) or (S) (e.g., (R, S), (S, R), (R, R), or (S, S)). In some preferred embodiments, an enantiomerically enriched sample of a compound of Formulas I-III is provided wherein both the carbon to which $R_1$ and $R_5$ is attached and the carbon to which $R_6$ is attached are independently (R) or (S) (e.g., (R, S), (S, R), (R, R), or (S, S)). In some preferred embodiments, an enantiomerically enriched sample of a compound of Formulas I-III is provided wherein both the carbon to which $R_2$ is attached and the carbon to which $R_4$ is attached are independently (R) or (S) (e.g., (R, S), (S, R), (R, R), or (S, S)). Obviously, compounds are within the scope of the present invention wherein one, two, three, or four chiral centers are provided on the morpholine ring. Accordingly, various enantiomerically enriched compounds may be provided, wherein the compounds may be racemic with respect to one or more chiral centers and/or enantiomerically enriched with respect to one or more chiral centers.

The prodrugs of the present invention may be prodrugs according to Formula IV with one or more chiral centers, which may be either of the (R) or (S) configuration, or which may comprise a mixture thereof. The carbon to which $R_1$ and $R_5$ are connected may be either of the R or S configuration. When $R_2$ is a substituent other than H, the carbon to which $R_2$ is connected is chiral and may be either of the R or S configuration. When $R_4$ is a substituent other than H, the carbon to which $R_4$ is connected to is chiral and may be either of the R or S configuration. When $R_6$ is a substituent other than H, the carbon to which $R_6$ is connected to is chiral and may be either of the R or S configuration. Accordingly, the present invention includes both racemic mixtures of prodrugs of Formula IV and isolated isomers of Formula IV. Where more than one chiral center is present in a compound of the invention, some, none, or all of the chiral centers may be enantiomerically enriched. Thus, mixtures of a compound of Formula IV may be racemic with respect to one or more chiral centers and/or enantiomerically enriched with respect to one or more chiral centers.

In some preferred embodiments, an enantiomerically enriched sample of a prodrug of Formula IV is provided wherein the carbon to which $R_1$ and $R_5$ are attached is (R) or (S). In some preferred embodiments, an enantiomerically enriched sample of a prodrug of Formula IV is provided wherein the carbon to which $R_2$ is attached is (R) or (S). In some preferred embodiments, an enantiomerically enriched sample of a prodrug of Formula IV is provided wherein the carbon to which $R_4$ is attached is (R) or (S). In some preferred embodiments, an enantiomerically enriched sample of a prodrug of Formula IV is provided wherein both the carbon to which $R_1$ and $R_5$ are attached and the carbon to which $R_2$ is attached are independently (R) or (S) (e.g., (R, S), (S, R), (R, R), or (S, S)). In some preferred embodiments, an enantiomerically enriched sample of a prodrug of Formula IV is provided wherein both the carbon to which $R_1$ and $R_5$ are attached and the carbon to which $R_4$ is attached are independently (R) or (S) (e.g., (R, S), (S, R), (R, R), or (S, S)). In some preferred embodiments, an enantiomerically enriched sample of a prodrug of Formula IV is provided wherein both the carbon to which $R_2$ is attached and the carbon to which $R_4$ is attached are independently (R) or (S) (e.g., (R, S), (S, R), (R, R), or (S, S)).

Various methods are known in the art for preparing optically active forms and determining activity. Such methods include standard tests described herein and other similar tests which are well known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular, to the extent of 95% or more, 96% or more, 97% or more, 98% or more, or 99% or more, including 100%.

In some embodiments, a compound of Formula I or a prodrug of Formula V is provided, wherein the compound contains one or more chiral centers. Specifically, the carbon to which $R_1$ and $R_5$ is attached is a chiral center, and may have either an R or S configuration. Depending on the substituents on the compound, other chiral centers may be present in the compound as well. In some embodiments, the compound is provided in a composition that is enantiomerically enriched. One preferred configuration is represented below in Figure VII. The chiral center(s) present in the compounds may be designated as either R or S, depending on the specific substituents on the chiral center. For example, in Formula VII below, when $R_1$ is phenyl and $R_5$ is H, the carbon center is designated as R, whereas when $R_1$ is phenyl and $R_5$ is OH, the carbon center is designated as S.

Although various stereoisomers may be represented by the previous formulas, one particularly preferred configuration of Foiinula I is represented by Formula VII:

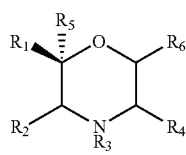

Formula VII or a pharmaceutically acceptable ester, amide, salt, solvate, prodrug, or isomer thereof.

In an alternative embodiment, a preferred configuration of Formula I is represented by Formula VIII, wherein $R_2$ is not H:

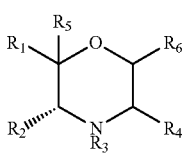

Formula VIII or a pharmaceutically acceptable ester, amide, salt, solvate, prodrug, or isomer thereof.

In one embodiment, $R_2$ is not H and a chiral center exists both at the carbon to which $R_1$ and $R_5$ are attached, and at the carbon alpha to the amine of the morpholine ring (to which $R_2$ is attached), as shown below in Formula IX:

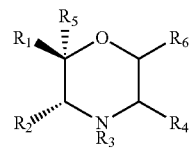

Formula IX or a pharmaceutically acceptable ester, amide, salt, solvate, prodrug, or isomer thereof.

In another embodiment, an alternative enantiomer is provided, represented by Formula X:

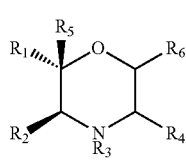

Formula X or a pharmaceutically acceptable ester, amide, salt, solvate, prodrug, or isomer thereof.

These compounds or prodrugs, wherein two chiral centers are present in the molecule, may be (R,R), (S,S), (R,S), or (S,R) isomers. The "trans" compounds, wherein one of $R_1$ and $R_2$ is above the plane of the molecule and one of $R_1$ and $R_2$ is below the plane of the molecule are encompassed by the invention. The "cis" compounds, wherein $R_2$ and $R_1$ are both above the plane of the molecule, or wherein $R_1$ and $R_2$ are both below the plane of the molecule, are also within the purview of this invention. In these compounds, as noted above, the identity of the substituents comprising $R_1$ and $R_5$ will determine whether the carbon center to which these substituents are attached is designated as R or S.

As noted above, the carbon centers to which $R_2$, $R_4$ and $R_6$ are attached may be chiral, when these substituents are not H. Compounds wherein one or more of the four carbons on the morpholine ring are chiral are encompassed within the present invention. Compounds that are enantiomerically enriched with regard to zero, one, two, three, or all four carbon centers on the morpholine ring are encompassed. All isomeric combinations are encompassed within the present invention.

The terms (R), (S), (R,R), (S,S), (R,S) and (S,R) as used herein mean that the composition contains a greater proportion of the named isomer of the compound or prodrug in relation to other isomers. In a preferred embodiment these terms indicate that the composition contains at least 90% by weight of the named isomer and 10% by weight or less of the one or more other isomers; or more preferably about 95% by weight of the named isomer and 5% or less of the one or more other isomers. In some embodiments, the composition may contain at least 99% by weight of the named isomer and 1% or less by weight of the one or more other isomers, or may contain 100% by weight of the named isomer and 0% by weight of the one of more other isomers. These percentages are based on the total amount of the compound of the present invention present in the composition.

Additional chiral centers may be present in the compounds and prodrugs of the present invention. Compound samples wherein the compounds contain any of the aforementioned chiral centers may be racemic or may be enantiomerically enriched. Where more than one chiral center is present in a compound or prodrug of the invention, some, none, or all of the chiral centers may be enantiomerically enriched. Thus, they may be racemic with respect to one or more chiral centers and/or enantiomerically enriched with respect to one or more chiral centers.

The compounds and prodrugs of the present invention may be utilized per se or in the form of a pharmaceutically acceptable ester, amide, salt, solvate, prodrug, or isomer. For example, the compound or prodrug may be provided as a pharmaceutically acceptable salt. If used, a salt of the drug compound or prodrug should be both pharmacologically and pharmaceutically acceptable, but non-pharmaceutically acceptable salts may conveniently be used to prepare the free active compound, prodrug, or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature.

Examples of pharmaceutically acceptable salts of the compounds and prodrugs useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzenesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound or prodrug useful according to the present invention may be prepared in a similar manner using a pharmaceutically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound or prodrug. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds and prodrugs of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds and prodrugs used in the methods of the invention may exist in different forms. For example, the compounds or prodrugs may exist in stable and metastable crystalline forms and isotropic and amorphous forms, all of which are intended to be within the scope of the present invention.

If a compound or prodrug useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound or prodrug described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

Some preferred compounds of the invention include the following, wherein $R_4$ and $R_5$ are H, the $R_1$ substituent on the morpholine ring is phenyl and the substituents on the phenyl are varied.

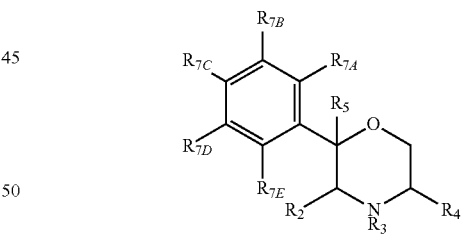

TABLE 1

Representative Compounds of the Invention

| $R_2$ | $R_3$ | $R_4$ | $R_5$ | $R_{7A}$ | $R_{7B}$ | $R_{7C}$ | $R_{7D}$ | $R_{7E}$ |
|---|---|---|---|---|---|---|---|---|
| $CH_3$ | H | H | H | $CH_3$ | H | H | H | H |
| $CH_3$ | H | H | H | H | $CH_3$ | H | H | H |
| $CH_3$ | H | H | H | H | H | $CH_3$ | H | H |
| $CH_3$ | H | H | H | $CH_3$ | $CH_3$ | H | H | H |
| $CH_3$ | H | H | H | $CH_3$ | H | $CH_3$ | H | H |
| $CH_3$ | H | H | H | $CH_3$ | H | H | $CH_3$ | H |
| $CH_3$ | H | H | H | $CH_3$ | H | H | H | $CH_3$ |
| $CH_3$ | H | H | H | H | $CH_3$ | $CH_3$ | H | H |
| $CH_3$ | H | H | H | H | $CH_3$ | H | $CH_3$ | H |

TABLE 1-continued

Representative Compounds of the Invention

| R$_2$ | R$_3$ | R$_4$ | R$_5$ | R$_{7A}$ | R$_{7B}$ | R$_{7C}$ | R$_{7D}$ | R$_{7E}$ |
|---|---|---|---|---|---|---|---|---|
| CH$_3$ | H | H | H | CH$_3$ | CH$_3$ | CH$_3$ | H | H |
| CH$_3$ | H | H | H | H | CH$_3$ | CH$_3$ | CH$_3$ | H |
| CH$_3$ | H | H | H | CH$_3$ | H | CH$_3$ | H | CH$_3$ |
| CH$_3$ | H | H | H | CH$_3$ | H | H | CH$_3$ | CH$_3$ |
| CH$_3$ | H | H | H | CH$_3$ | CH$_3$ | H | CH$_3$ | H |
| CH$_3$ | H | H | H | CH$_3$ | CH$_3$ | CH$_3$ | CH$_3$ | H |
| CH$_3$ | H | H | H | CH$_3$ | H | CH$_3$ | CH$_3$ | CH$_3$ |
| CH$_3$ | H | H | H | CH$_3$ | CH$_3$ | H | CH$_3$ | CH$_3$ |
| CH$_3$ | H | H | H | CH$_3$ | CH$_3$ | CH$_3$ | CH$_3$ | CH$_3$ |
| CH$_3$ | H | H | H | CH$_2$CH$_3$ | H | H | H | H |
| CH$_3$ | H | H | H | H | CH$_2$CH$_3$ | H | H | H |
| CH$_3$ | H | H | H | H | H | CH$_2$CH$_3$ | H | H |
| CH$_3$ | H | H | H | CH$_2$CH$_3$ | CH$_2$CH$_3$ | H | H | H |
| CH$_3$ | H | H | H | CH$_2$CH$_3$ | H | CH$_2$CH$_3$ | H | H |
| CH$_3$ | H | H | H | CH$_2$CH$_3$ | H | H | CH$_2$CH$_3$ | H |
| CH$_3$ | H | H | H | CH$_2$CH$_3$ | H | H | H | CH$_2$CH$_3$ |
| CH$_3$ | H | H | H | H | CH$_2$CH$_3$ | CH$_2$CH$_3$ | H | H |
| CH$_3$ | H | H | H | H | CH$_2$CH$_3$ | H | CH$_2$CH$_3$ | H |
| CH$_3$ | H | H | H | CH$_2$CH$_3$ | CH$_2$CH$_3$ | CH$_2$CH$_3$ | H | H |
| CH$_3$ | H | H | H | H | CH$_2$CH$_3$ | CH$_2$CH$_3$ | CH$_2$CH$_3$ | H |
| CH$_3$ | H | H | H | CH$_2$CH$_3$ | H | CH$_2$CH$_3$ | H | CH$_2$CH$_3$ |
| CH$_3$ | H | H | H | CH$_2$CH$_3$ | H | H | CH$_2$CH$_3$ | CH$_2$CH$_3$ |
| CH$_3$ | H | H | H | CH$_2$CH$_3$ | H | CH$_2$CH$_3$ | CH$_2$CH$_3$ | H |
| CH$_3$ | H | H | H | CH$_2$CH$_3$ | CH$_2$CH$_3$ | CH$_2$CH$_3$ | CH$_2$CH$_3$ | H |
| CH$_3$ | H | H | H | CH$_2$CH$_3$ | H | CH$_2$CH$_3$ | CH$_2$CH$_3$ | CH$_2$CH$_3$ |
| CH$_3$ | H | H | H | CH$_2$CH$_3$ | CH$_2$CH$_3$ | H | CH$_2$CH$_3$ | CH$_2$CH$_3$ |
| CH$_3$ | H | H | H | CH$_2$CH$_3$ | CH$_2$CH$_3$ | CH$_2$CH$_3$ | CH$_2$CH$_3$ | CH$_2$CH$_3$ |
| CH$_3$ | H | H | H | Cl | H | H | H | H |
| CH$_3$ | H | H | H | H | Cl | H | H | H |
| CH$_3$ | H | H | H | H | H | Cl | H | H |
| CH$_3$ | H | H | H | Cl | Cl | H | H | H |
| CH$_3$ | H | H | H | Cl | H | Cl | H | H |
| CH$_3$ | H | H | H | Cl | H | H | Cl | H |
| CH$_3$ | H | H | H | Cl | H | H | H | Cl |
| CH$_3$ | H | H | H | H | Cl | Cl | H | H |
| CH$_3$ | H | H | H | H | Cl | H | Cl | H |
| CH$_3$ | H | H | H | Cl | Cl | Cl | H | H |
| CH$_3$ | H | H | H | H | Cl | Cl | Cl | H |
| CH$_3$ | H | H | H | Cl | H | Cl | H | Cl |
| CH$_3$ | H | H | H | Cl | H | H | Cl | Cl |
| CH$_3$ | H | H | H | Cl | H | Cl | Cl | H |
| CH$_3$ | H | H | H | Cl | Cl | Cl | Cl | H |
| CH$_3$ | H | H | H | Cl | H | Cl | Cl | Cl |
| CH$_3$ | H | H | H | Cl | Cl | H | Cl | Cl |
| CH$_3$ | H | H | H | Cl | Cl | Cl | Cl | Cl |
| CH$_3$ | H | H | H | F | H | H | H | H |
| CH$_3$ | H | H | H | H | F | H | H | H |
| CH$_3$ | H | H | H | H | H | F | H | H |
| CH$_3$ | H | H | H | F | F | H | H | H |
| CH$_3$ | H | H | H | F | H | F | H | H |
| CH$_3$ | H | H | H | F | H | H | F | H |
| CH$_3$ | H | H | H | F | H | H | H | F |
| CH$_3$ | H | H | H | H | F | F | H | H |
| CH$_3$ | H | H | H | H | F | H | F | H |
| CH$_3$ | H | H | H | F | F | F | H | H |
| CH$_3$ | H | H | H | H | F | F | F | H |
| CH$_3$ | H | H | H | F | H | F | H | F |
| CH$_3$ | H | H | H | F | H | H | F | F |
| CH$_3$ | H | H | H | F | F | H | F | H |
| CH$_3$ | H | H | H | F | F | H | F | F |
| CH$_3$ | H | H | H | F | F | F | F | F |
| CH$_3$ | H | H | H | Br | H | H | H | H |
| CH$_3$ | H | H | H | H | Br | H | H | H |
| CH$_3$ | H | H | H | H | H | Br | H | H |
| CH$_3$ | H | H | H | Br | Br | H | H | H |
| CH$_3$ | H | H | H | Br | H | Br | H | H |
| CH$_3$ | H | H | H | Br | H | H | Br | H |
| CH$_3$ | H | H | H | Br | H | H | H | Br |
| CH$_3$ | H | H | H | H | Br | Br | H | H |
| CH$_3$ | H | H | H | H | Br | H | Br | H |
| CH$_3$ | H | H | H | Br | Br | Br | H | H |
| CH$_3$ | H | H | H | H | Br | Br | Br | H |
| CH$_3$ | H | H | H | Br | H | Br | H | Br |
| CH$_3$ | H | H | H | Br | H | H | Br | Br |
| CH$_3$ | H | H | H | Br | H | Br | Br | H |
| CH$_3$ | H | H | H | Br | Br | Br | Br | H |
| CH$_3$ | H | H | H | Br | H | Br | Br | Br |
| CH$_3$ | H | H | H | Br | Br | H | Br | Br |
| CH$_3$ | H | H | H | Br | Br | Br | Br | Br |
| CH$_3$ | H | H | H | OCH$_3$ | H | H | H | H |
| CH$_3$ | H | H | H | H | OCH$_3$ | H | H | H |
| CH$_3$ | H | H | H | H | H | OCH$_3$ | H | H |
| CH$_3$ | H | H | H | OCH$_3$ | OCH$_3$ | H | H | H |
| CH$_3$ | H | H | H | OCH$_3$ | H | OCH$_3$ | H | H |
| CH$_3$ | H | H | H | OCH$_3$ | H | H | OCH$_3$ | H |
| CH$_3$ | H | H | H | OCH$_3$ | H | H | H | OCH$_3$ |
| CH$_3$ | H | H | H | H | OCH$_3$ | OCH$_3$ | H | H |
| CH$_3$ | H | H | H | H | OCH$_3$ | H | OCH$_3$ | H |
| CH$_3$ | H | H | H | OCH$_3$ | OCH$_3$ | OCH$_3$ | H | H |
| CH$_3$ | H | H | H | H | OCH$_3$ | OCH$_3$ | OCH$_3$ | H |
| CH$_3$ | H | H | H | OCH$_3$ | H | OCH$_3$ | H | OCH$_3$ |
| CH$_3$ | H | H | H | OCH$_3$ | H | OCH$_3$ | OCH$_3$ | H |
| CH$_3$ | H | H | H | OCH$_3$ | OCH$_3$ | OCH$_3$ | OCH$_3$ | H |
| CH$_3$ | H | H | H | OCH$_3$ | H | OCH$_3$ | OCH$_3$ | OCH$_3$ |
| CH$_3$ | H | H | H | OCH$_3$ | OCH$_3$ | H | OCH$_3$ | OCH$_3$ |
| CH$_3$ | H | H | H | OCH$_3$ | OCH$_3$ | OCH$_3$ | OCH$_3$ | OCH$_3$ |
| CH$_3$ | H | H | H | CN | H | H | H | H |
| CH$_3$ | H | H | H | H | CN | H | H | H |
| CH$_3$ | H | H | H | H | H | CN | H | H |
| CH$_3$ | H | H | H | CN | CN | H | H | H |
| CH$_3$ | H | H | H | CN | H | CN | H | H |
| CH$_3$ | H | H | H | CN | H | H | CN | H |
| CH$_3$ | H | H | H | CN | H | H | H | CN |
| CH$_3$ | H | H | H | H | CN | CN | H | H |
| CH$_3$ | H | H | H | H | CN | H | CN | H |
| CH$_3$ | H | H | H | CN | CN | CN | H | H |
| CH$_3$ | H | H | H | H | CN | CN | CN | H |
| CH$_3$ | H | H | H | CN | H | CN | H | CN |
| CH$_3$ | H | H | H | CN | H | H | CN | CN |
| CH$_3$ | H | H | H | CN | H | CN | CN | H |
| CH$_3$ | H | H | H | CN | CN | CN | CN | H |
| CH$_3$ | H | H | H | CN | H | CN | CN | CN |
| CH$_3$ | H | H | H | CN | CN | H | CN | CN |
| CH$_3$ | H | H | H | CN | CN | CN | CN | CN |
| CH$_3$ | H | H | H | OH | H | H | H | H |
| CH$_3$ | H | H | H | H | OH | H | H | H |
| CH$_3$ | H | H | H | H | H | OH | H | H |
| CH$_3$ | H | H | H | OH | OH | H | H | H |
| CH$_3$ | H | H | H | OH | H | OH | H | H |
| CH$_3$ | H | H | H | OH | H | H | OH | H |
| CH$_3$ | H | H | H | OH | H | H | H | OH |
| CH$_3$ | H | H | H | H | OH | OH | H | H |
| CH$_3$ | H | H | H | H | OH | H | OH | H |
| CH$_3$ | H | H | H | OH | OH | OH | H | H |
| CH$_3$ | H | H | H | H | OH | OH | OH | H |
| CH$_3$ | H | H | H | OH | H | OH | H | OH |
| CH$_3$ | H | H | H | OH | H | H | OH | OH |
| CH$_3$ | H | H | H | OH | H | OH | OH | H |
| CH$_3$ | H | H | H | OH | OH | OH | OH | H |
| CH$_3$ | H | H | H | OH | H | OH | OH | OH |
| CH$_3$ | H | H | H | OH | OH | H | OH | OH |
| CH$_3$ | H | H | H | OH | OH | OH | OH | OH |
| CH$_3$ | H | H | H | Cl | F | H | H | H |
| CH$_3$ | H | H | H | Cl | H | F | H | H |
| CH$_3$ | H | H | H | Cl | H | H | F | H |
| CH$_3$ | H | H | H | Cl | H | H | H | F |
| CH$_3$ | H | H | H | F | Cl | H | H | H |
| CH$_3$ | H | H | H | H | Cl | F | H | H |
| CH$_3$ | H | H | H | H | Cl | H | F | H |
| CH$_3$ | H | H | H | H | Cl | H | H | F |
| CH$_3$ | H | H | H | F | H | Cl | H | H |
| CH$_3$ | H | H | H | H | F | Cl | H | H |
| CH$_3$ | H | H | H | Cl | F | F | H | H |
| CH$_3$ | H | H | H | Cl | F | H | F | H |
| CH$_3$ | H | H | H | Cl | F | H | H | F |
| CH$_3$ | H | H | H | H | Cl | H | H | H |
| CH$_3$ | H | H | H | H | Cl | H | H | H |
| CH$_3$ | H | H | H | F | H | Cl | H | H |

TABLE 1-continued

Representative Compounds of the Invention

| $R_2$ | $R_3$ | $R_4$ | $R_5$ | $R_{7A}$ | $R_{7B}$ | $R_{7C}$ | $R_{7D}$ | $R_{7E}$ |
|---|---|---|---|---|---|---|---|---|
| CH3 | H | H | H | H | F | Cl | H | H |
| CH3 | H | H | H | Cl | F | F | F | H |
| CH3 | H | H | H | Cl | F | H | F | F |
| CH3 | H | H | H | Cl | H | F | F | F |
| CH3 | H | H | H | F | Cl | F | F | H |
| CH3 | H | H | H | F | Cl | H | F | F |
| CH3 | H | H | H | F | Cl | F | H | F |
| CH3 | H | H | H | F | F | Cl | F | H |
| CH3 | H | H | H | F | F | Cl | H | F |
| CH3 | H | H | H | Cl | F | F | F | F |
| CH3 | H | H | H | F | Cl | F | F | F |
| CH3 | H | 11 | H | F | F | Cl | F | F |
| CH3 | H | H | H | F | Cl | Cl | H | H |
| CH3 | H | H | H | F | Cl | H | Cl | H |
| CH3 | H | H | H | F | Cl | H | H | Cl |
| CH3 | H | H | H | H | F | H | H | H |
| CH3 | H | H | H | H | F | H | H | H |
| CH3 | H | H | H | H | F | H | H | H |
| CH3 | H | H | H | Cl | H | F | H | H |
| CH3 | H | H | H | H | Cl | F | H | H |
| CH3 | H | H | H | F | Cl | Cl | Cl | H |
| CH3 | H | H | H | F | Cl | H | Cl | Cl |
| CH3 | H | H | H | F | H | Cl | Cl | Cl |
| CH3 | H | H | H | Cl | F | Cl | Cl | H |
| CH3 | H | H | H | Cl | F | H | Cl | Cl |
| CH3 | H | H | H | Cl | F | Cl | H | Cl |
| CH3 | H | H | H | Cl | Cl | F | Cl | H |
| CH3 | H | H | H | Cl | Cl | F | H | Cl |
| CH3 | H | H | H | F | Cl | Cl | Cl | Cl |
| CH3 | H | H | H | Cl | F | Cl | Cl | Cl |
| CH3 | H | H | H | Cl | Cl | F | Cl | Cl |
| CH3 | H | H | H | CF3 | H | H | H | H |
| CH3 | H | H | H | H | CF3 | H | H | H |
| CH3 | H | H | H | H | H | CF3 | H | H |
| CH3 | H | H | H | CF3 | CF3 | H | H | H |
| CH3 | H | H | H | CF3 | H | CF3 | H | H |
| CH3 | H | H | H | CF3 | H | H | CF3 | H |
| CH3 | H | H | H | CF3 | H | H | H | CF3 |
| CH3 | H | H | H | H | CF3 | CF3 | H | H |
| CH3 | H | H | H | H | CF3 | H | CF3 | H |
| CH3 | H | H | H | CF3 | CF3 | CF3 | H | H |
| CH3 | H | H | H | H | CF3 | CF3 | CF3 | H |
| CH3 | H | H | H | CF3 | H | CF3 | H | CF3 |
| CH3 | H | H | H | CF3 | H | H | CF3 | CF3 |
| CH3 | H | H | H | CF3 | H | CF3 | CF3 | H |
| CH3 | H | H | H | CF3 | CF3 | CF3 | CF3 | H |
| CH3 | H | H | H | CF3 | H | CF3 | CF3 | CF3 |
| CH3 | H | H | H | CF3 | CF3 | H | CF3 | CF3 |
| CH3 | H | H | H | CF3 | CF3 | CF3 | CF3 | CF3 |

Some additional preferred compounds of the present invention include the following, wherein $R_4$ is $CH_3$, $R_2$ and $R_5$ are H, the $R_1$ substituent on the morpholine ring is a phenyl, and the substituents on the phenyl are varied.

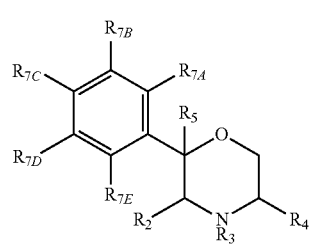

TABLE 2

Representative Compounds of the Invention

| $R_2$ | $R_3$ | $R_4$ | $R_5$ | $R_{7A}$ | $R_{7B}$ | $R_{7C}$ | $R_{7D}$ | $R_{7E}$ |
|---|---|---|---|---|---|---|---|---|
| H | H | CH3 | H | CH3 | H | H | H | H |
| H | H | CH3 | H | H | CH3 | H | H | H |
| H | H | CH3 | H | H | H | CH3 | H | H |
| H | H | CH3 | H | CH3 | CH3 | H | H | H |
| H | H | CH3 | H | CH3 | H | CH3 | H | H |
| H | H | CH3 | H | CH3 | H | H | CH3 | H |
| H | H | CH3 | H | CH3 | H | H | H | CH3 |
| H | H | CH3 | H | H | CH3 | CH3 | H | H |
| H | H | CH3 | H | H | CH3 | H | CH3 | H |
| H | H | CH3 | H | CH3 | CH3 | CH3 | H | H |
| H | H | CH3 | H | H | CH3 | CH3 | CH3 | H |
| H | H | CH3 | H | CH3 | H | CH3 | H | CH3 |
| H | H | CH3 | H | CH3 | H | H | CH3 | CH3 |
| H | H | CH3 | H | CH3 | CH3 | CH3 | CH3 | H |
| H | H | CH3 | H | CH3 | H | CH3 | CH3 | CH3 |
| H | H | CH3 | H | CH3 | CH3 | H | CH3 | CH3 |
| H | H | CH3 | H | CH3 | CH3 | CH3 | CH3 | CH3 |
| H | H | CH3 | H | CH2CH3 | H | H | H | H |
| H | H | CH3 | H | H | CH2CH3 | H | H | H |
| H | H | CH3 | H | H | H | CH2CH3 | H | H |
| H | H | CH3 | H | CH2CH3 | CH2CH3 | H | H | H |
| H | H | CH3 | H | CH2CH3 | H | CH2CH3 | H | H |
| H | H | CH3 | H | CH2CH3 | H | H | CH2H3 | H |
| H | H | CH3 | H | CH2CH3 | H | H | H | CH2CH3 |
| H | H | CH3 | H | H | CH2CH3 | CH2CH3 | H | H |
| H | H | CH3 | H | H | CH2CH3 | H | CH2CH3 | H |
| H | H | CH3 | H | CH2CH3 | CH2CH3 | CH2CH3 | H | H |
| H | H | CH3 | H | H | CH2CH3 | CH2CH3 | CH2CH3 | H |
| H | H | CH3 | H | CH2CH3 | H | CH2CH3 | H | CH2CH3 |
| H | H | CH3 | H | CH2CH3 | H | H | CH2CH3 | CH2CH3 |
| H | H | CH3 | H | CH2CH3 | H | CH2CH3 | CH2CH3 | H |
| H | H | CH3 | H | CH2CH3 | CH2CH3 | CH2CH3 | CH2CH3 | H |
| H | H | CH3 | H | CH2CH3 | H | CH2CH3 | CH2CH3 | CH2CH3 |
| H | H | CH3 | H | CH2CH3 | CH2CH3 | H | CH2CH3 | CH2CH3 |
| H | H | CH3 | H | CH2CH3 | CH2CH3 | CH2CH3 | CH2CH3 | CH2CH3 |
| H | H | CH3 | H | Cl | H | H | H | H |
| H | H | CH3 | H | H | Cl | H | H | H |
| H | H | CH3 | H | H | H | Cl | H | H |
| H | H | CH3 | H | Cl | Cl | H | H | H |
| H | H | CH3 | H | Cl | H | Cl | H | H |
| H | H | CH3 | H | Cl | H | H | Cl | H |
| H | H | CH3 | H | Cl | H | H | H | Cl |
| H | H | CH3 | H | H | Cl | Cl | H | H |
| H | H | CH3 | H | H | Cl | H | Cl | H |
| H | H | CH3 | H | Cl | Cl | Cl | H | H |
| H | H | CH3 | H | H | Cl | Cl | Cl | H |
| H | H | CH3 | H | Cl | H | Cl | H | Cl |
| H | H | CH3 | H | Cl | H | H | Cl | Cl |
| H | H | CH3 | H | Cl | H | Cl | Cl | H |
| H | H | CH3 | H | Cl | Cl | Cl | Cl | H |
| H | H | CH3 | H | Cl | H | Cl | Cl | Cl |
| H | H | CH3 | H | Cl | Cl | H | Cl | Cl |
| H | H | CH3 | H | Cl | Cl | Cl | Cl | Cl |
| H | H | CH3 | H | F | H | H | H | H |
| H | H | CH3 | H | H | F | H | H | H |
| H | H | CH3 | H | H | H | F | H | H |
| H | H | CH3 | H | F | F | H | H | H |
| H | H | CH3 | H | F | H | F | H | H |
| H | H | CH3 | H | F | H | H | F | H |
| H | H | CH3 | H | F | H | H | H | F |
| H | H | CH3 | H | H | F | F | H | H |
| H | H | CH3 | H | H | F | H | F | H |
| H | H | CH3 | H | F | F | F | H | H |
| H | H | CH3 | H | H | F | F | F | H |
| H | H | CH3 | H | F | H | F | H | F |
| H | H | CH3 | H | F | H | H | F | F |
| H | H | CH3 | H | F | H | F | F | H |
| H | H | CH3 | H | F | F | F | F | H |
| H | H | CH3 | H | F | H | F | F | F |
| H | H | CH3 | H | F | F | H | F | F |
| H | H | CH3 | H | F | F | F | F | F |
| H | H | CH3 | H | Br | H | H | H | H |
| H | H | CH3 | H | H | Br | H | H | H |
| H | H | CH3 | H | H | H | Br | H | H |
| H | H | CH3 | H | Br | Br | H | H | H |

TABLE 2-continued

Representative Compounds of the Invention

| R₂ | R₃ | R₄ | R₅ | R₇ₐ | R₇ᵦ | R₇c | R₇ᴅ | R₇ₑ |
|---|---|---|---|---|---|---|---|---|
| H | H | CH₃ | H | Br | H | Br | H | H |
| H | H | CH₃ | H | Br | H | H | Br | H |
| H | H | CH₃ | H | Br | H | H | H | Br |
| H | H | CH₃ | H | H | Br | Br | H | H |
| H | H | CH₃ | H | H | Br | H | Br | H |
| H | H | CH₃ | H | Br | Br | Br | H | H |
| H | H | CH₃ | H | H | Br | Br | Br | H |
| H | H | CH₃ | H | Br | H | Br | H | Br |
| H | H | CH₃ | H | Br | H | H | Br | Br |
| H | H | CH₃ | H | Br | H | Br | Br | H |
| H | H | CH₃ | H | Br | Br | Br | Br | H |
| H | H | CH₃ | H | Br | H | Br | Br | Br |
| H | H | CH₃ | H | Br | Br | H | Br | Br |
| H | H | CH₃ | H | Br | Br | Br | Br | Br |
| H | H | CH₃ | H | OCH₃ | H | H | H | H |
| H | H | CH₃ | H | H | OCH₃ | H | H | H |
| H | H | CH₃ | H | H | H | OCH₃ | H | H |
| H | H | CH₃ | H | OCH₃ | OCH₃ | H | H | H |
| H | H | CH₃ | H | OCH₃ | H | OCH₃ | H | H |
| H | H | CH₃ | H | OCH₃ | H | H | OCH₃ | H |
| H | H | CH₃ | H | OCH₃ | H | H | H | OCH₃ |
| H | H | CH₃ | H | H | OCH₃ | OCH₃ | H | H |
| H | H | CH₃ | H | H | OCH₃ | H | OCH₃ | H |
| H | H | CH₃ | H | OCH₃ | OCH₃ | OCH₃ | H | H |
| H | H | CH₃ | H | H | OCH₃ | OCH₃ | OCH₃ | H |
| H | H | CH₃ | H | OCH₃ | H | OCH₃ | H | OCH₃ |
| H | H | CH₃ | H | OCH₃ | H | H | OCH₃ | OCH₃ |
| H | H | CH₃ | H | OCH₃ | H | OCH₃ | OCH₃ | H |
| H | H | CH₃ | H | OCH₃ | OCH₃ | OCH₃ | OCH₃ | H |
| H | H | CH₃ | H | OCH₃ | H | OCH₃ | OCH₃ | OCH₃ |
| H | H | CH₃ | H | OCH₃ | OCH₃ | H | OCH₃ | OCH₃ |
| H | H | CH₃ | H | OCH₃ | OCH₃ | OCH₃ | OCH₃ | OCH₃ |
| H | H | CH₃ | H | CN | H | H | H | H |
| H | H | CH₃ | H | H | CN | H | H | H |
| H | H | CH₃ | H | H | H | CN | H | H |
| H | H | CH₃ | H | CN | CN | H | H | H |
| H | H | CH₃ | H | CN | H | CN | H | H |
| H | H | CH₃ | H | CN | H | H | CN | H |
| H | H | CH₃ | H | CN | H | H | H | CN |
| H | H | CH₃ | H | H | CN | CN | H | H |
| H | H | CH₃ | H | H | CN | H | CN | H |
| H | H | CH₃ | H | CN | CN | CN | H | H |
| H | H | CH₃ | H | H | CN | CN | CN | H |
| H | H | CH₃ | H | CN | H | CN | H | CN |
| H | H | CH₃ | H | CN | H | H | CN | CN |
| H | H | CH₃ | H | CN | H | CN | CN | H |
| H | H | CH₃ | H | CN | CN | CN | CN | H |
| H | H | CH₃ | H | CN | H | CN | CN | CN |
| H | H | CH₃ | H | CN | CN | H | CN | CN |
| H | H | CH₃ | H | OH | H | H | H | H |
| H | H | CH₃ | H | H | OH | H | H | H |
| H | H | CH₃ | H | H | H | OH | H | H |
| H | H | CH₃ | H | OH | OH | H | H | H |
| H | H | CH₃ | H | OH | H | OH | H | H |
| H | H | CH₃ | H | OH | H | H | OH | H |
| H | H | CH₃ | H | OH | H | H | H | OH |
| H | H | CH₃ | H | H | OH | OH | H | H |
| H | H | CH₃ | H | H | OH | H | OH | H |
| H | H | CH₃ | H | OH | OH | OH | H | H |
| H | H | CH₃ | H | H | OH | OH | OH | H |
| H | H | CH₃ | H | OH | H | OH | H | OH |
| H | H | CH₃ | H | OH | H | H | OH | OH |
| H | H | CH₃ | H | OH | H | OH | OH | H |
| H | H | CH₃ | H | OH | OH | OH | OH | H |
| H | H | CH₃ | H | OH | H | OH | OH | OH |
| H | H | CH₃ | H | OH | OH | H | OH | OH |
| H | H | CH₃ | H | OH | OH | OH | OH | OH |
| H | H | CH₃ | H | Cl | F | H | H | H |
| H | H | CH₃ | H | Cl | H | F | H | H |
| H | H | CH₃ | H | Cl | H | H | F | H |
| H | H | CH₃ | H | Cl | H | H | H | F |
| H | H | CH₃ | H | F | Cl | H | H | H |
| H | H | CH₃ | H | H | Cl | F | H | H |
| H | H | CH₃ | H | H | Cl | H | F | H |
| H | H | CH₃ | H | H | Cl | H | H | F |
| H | H | CH₃ | H | F | H | Cl | H | H |
| H | H | CH₃ | H | H | F | Cl | H | H |
| H | H | CH₃ | H | Cl | F | F | H | H |
| H | H | CH₃ | H | Cl | F | H | F | H |
| H | H | CH₃ | H | Cl | F | H | H | F |
| H | H | CH₃ | H | H | Cl | H | H | H |
| H | H | CH₃ | H | H | Cl | H | H | H |
| H | H | CH₃ | H | H | Cl | H | H | H |
| H | H | CH₃ | H | F | H | Cl | H | H |
| H | H | CH₃ | H | H | F | Cl | H | H |
| H | H | CH₃ | H | Cl | F | F | F | H |
| H | H | CH₃ | H | Cl | F | H | F | F |
| H | H | CH₃ | H | Cl | H | F | F | F |
| H | H | CH₃ | H | F | Cl | F | F | H |
| H | H | CH₃ | H | F | Cl | H | F | F |
| H | H | CH₃ | H | F | F | Cl | F | H |
| H | H | CH₃ | H | Cl | F | F | F | F |
| H | H | CH₃ | H | F | Cl | F | F | F |
| H | H | CH₃ | H | F | F | Cl | F | F |
| H | H | CH₃ | H | F | Cl | Cl | H | H |
| H | H | CH₃ | H | F | Cl | H | Cl | H |
| H | H | CH₃ | H | F | Cl | H | H | Cl |
| H | H | CH₃ | H | H | F | H | H | H |
| H | H | CH₃ | H | H | F | H | H | H |
| H | H | CH₃ | H | Cl | H | F | H | H |
| H | H | CH₃ | H | H | Cl | F | H | H |
| H | H | CH₃ | H | F | Cl | Cl | Cl | H |
| H | H | CH₃ | H | F | Cl | H | Cl | Cl |
| H | H | CH₃ | H | F | H | Cl | Cl | Cl |
| H | H | CH₃ | H | Cl | F | Cl | Cl | H |
| H | H | CH₃ | H | Cl | F | H | Cl | Cl |
| H | H | CH₃ | H | Cl | F | Cl | H | Cl |
| H | H | CH₃ | H | Cl | Cl | F | Cl | H |
| H | H | CH₃ | H | Cl | Cl | F | H | Cl |
| H | H | CH₃ | H | F | Cl | Cl | Cl | Cl |
| H | H | CH₃ | H | Cl | F | Cl | Cl | Cl |
| H | H | CH₃ | H | Cl | Cl | F | Cl | Cl |
| H | H | CH₃ | H | CF₃ | H | H | H | H |
| H | H | CH₃ | H | H | CF₃ | H | H | H |
| H | H | CH₃ | H | H | H | CF₃ | H | H |
| H | H | CH₃ | H | CF₃ | CF₃ | H | H | H |
| H | H | CH₃ | H | CF₃ | H | CF₃ | H | H |
| H | H | CH₃ | H | CF₃ | H | H | CF₃ | H |
| H | H | CH₃ | H | CF₃ | H | H | H | CF₃ |
| H | H | CH₃ | H | H | CF₃ | CF₃ | H | H |
| H | H | CH₃ | H | H | CF₃ | H | CF₃ | H |
| H | H | CH₃ | H | CF₃ | CF₃ | CF₃ | H | H |
| H | H | CH₃ | H | H | CF₃ | CF₃ | CF₃ | H |
| H | H | CH₃ | H | CF₃ | H | CF₃ | H | CF₃ |
| H | H | CH₃ | H | CF₃ | H | H | CF₃ | CF₃ |
| H | H | CH₃ | H | CF₃ | H | CF₃ | CF₃ | H |
| H | H | CH₃ | H | CF₃ | CF₃ | CF₃ | CF₃ | H |
| H | H | CH₃ | H | CF₃ | H | CF₃ | CF₃ | CF₃ |
| H | H | CH₃ | H | CF₃ | CF₃ | H | CF₃ | CF₃ |
| H | H | CH₃ | H | CF₃ | CF₃ | CF₃ | CF₃ | CF₃ |

The compounds of the present invention may display different types of activities. In general, the compounds of the present invention may function as monoamine neurotransmitter releasers, which effectuate the release of one or more of dopamine, norepinephrine, and/or serotonin and/or may act as monoamine neurotransmitter uptake inhibitors. In certain embodiments, the compounds cause release of dopamine. In certain embodiments, compounds that cause dopamine release are desirable because they may be useful for treatment of stimulant (e.g., cocaine and methamphetamine) addiction.

In certain embodiments, the compounds cause release of serotonin. In some embodiments, the compounds cause release of dopamine and serotonin. In some of these embodiments, there is little or no norepinephrine release. In some embodiments, the compounds show little or no activity at the $5HT_{2B}$ receptor. In some embodiments, the compounds of the present invention function as uptake inhibitors of one or more monoamine neurotransmitters. In particular embodiments, the compounds show hybrid activity in that they cause release of one or more monoamines and also cause uptake inhibition of one or more monoamines. For example, in some embodiments, compounds of the present invention act as dopamine and/or norepinephrine releasers and as serotonin uptake inhibitors. In certain embodiments, the compounds are serotonin releasers or serotonin uptake inhibitors, but display little to no activity at the $5HT_{2B}$ receptor.

In some embodiments, phenyl ring substitution increases serotonin release. In certain embodiments, increased serotonin release is desirable in decreasing the addiction liability commonly demonstrated by dopamine releasers and some combination dopamine/serotonin releasers.

Compositions

While it is possible for the compounds and prodrugs of the present invention to be administered in the raw chemical form, it is preferred for the compounds or prodrugs to be delivered as a pharmaceutical formulation. Accordingly, there are provided by the present invention pharmaceutical compositions comprising at least one compound capable of inhibiting the reuptake of one or more monoamines. As such, the formulations of the present invention comprise a compound of any of the formulas noted herein, as described above, or a pharmaceutically acceptable ester, amide, salt, or solvate thereof, together with one or more pharmaceutically acceptable carriers therefore, and optionally, other therapeutic ingredients.

By "pharmaceutically acceptable carrier" is intended a carrier that is conventionally used in the art to facilitate the storage, administration, and/or the healing effect of the agent. The carrier(s) must be pharmaceutically acceptable in the sense of being compatible with the other ingredients of the formulation and not unduly deleterious to the recipient thereof. A carrier may also reduce any undesirable side effects of the agent. Such carriers are known in the art. See, Wang et al. (1980) *J. Parent. Drug Assn.* 34(6):452-462, herein incorporated by reference in its entirety.

Adjuvants or accessory ingredients for use in the formulations of the present invention can include any pharmaceutical ingredient commonly deemed acceptable in the art, such as binders, fillers, lubricants, disintegrants, diluents, surfactants, stabilizers, preservatives, flavoring and coloring agents, and the like. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other exemplary pharmaceutical excipients and/or additives suitable for use in the compositions according to the invention are listed in Remington: The Science & Practice of Pharmacy, 21$^{st}$ ed., Lippincott Williams & Wilkins (2006); in the Physician's Desk Reference, 64$^{th}$ ed., Thomson PDR (2010); and in Handbook of Pharmaceutical Excipients, 6$^{th}$ ed., Eds. Raymond C. Rowe et al., Pharmaceutical Press (2009), which are incorporated herein by reference.

Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluoses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the formulation according to the present invention may be anionic, cationic, amphoteric, or nonionic surface active agents. Stabilizers may be included in the formulations to inhibit or lessen reactions leading to decomposition of the active agent, such as oxidative reactions.

Formulations of the present invention may include short-term, rapid-onset, rapid-offset, controlled release, sustained release, delayed release, and pulsatile release formulations, providing the formulations achieve administration of a compound as described herein. See *Remington's Pharmaceutical Sciences* (18$^{th}$ ed.; Mack Publishing Company, Eaton, Pa., 1990), herein incorporated by reference in its entirety.

Pharmaceutical formulations according to the present invention are suitable for various modes of delivery, including oral, parenteral (including intravenous, intramuscular, subcutaneous, intradermal, and transdermal), topical (including dermal, buccal, and sublingual), and rectal administration. The most useful and/or beneficial mode of administration can vary, especially depending upon the condition of the recipient and the disorder being treated. However, in preferred embodiments, the formulation is for oral delivery, as oral administration may provide the drug while maintaining abuse resistance.

The pharmaceutical formulations may be conveniently made available in a unit dosage form, whereby such formulations may be prepared by any of the methods generally known in the pharmaceutical arts. Generally speaking, such methods of preparation comprise combining (by various methods) an active agent, such as the compounds of Formula I according to the present invention (or a pharmaceutically acceptable ester, amide, salt, or solvate thereof) or the prodrugs of Formula IV, with a suitable carrier or other adjuvant, which may consist of one or more ingredients. The combination of the active ingredient with the one or more adjuvants is then physically treated to present the formulation in a suitable form for delivery (e.g., shaping into a tablet or forming an aqueous suspension).

Pharmaceutical formulations according to the present invention suitable as oral dosage may take various forms, such as tablets, capsules, caplets, and wafers (including rapidly dissolving or effervescing), each containing a predetermined amount of the active agent. The formulations may also be in the form of a powder or granules, a solution or suspension in an aqueous or non-aqueous liquid, and as a liquid emulsion (oil-in-water and water-in-oil). The active agent may also be delivered as a bolus, electuary, or paste. It is generally understood that methods of preparations of the above dosage forms are generally known in the art, and any such method would be suitable for the preparation of the respective dosage forms for use in delivery of the compounds according to the present invention.

A tablet containing a compound or prodrug according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agent.

Solid dosage forms may be formulated so as to provide a delayed release of the active agent, such as by application of a coating. Delayed release coatings are known in the art, and dosage from containing such may be prepared by any known suitable method. Such methods generally include that, after preparation of the solid dosage form (e.g., a tablet or caplet), a delayed release coating composition is applied. Application can be by methods such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agent over a prolonged period of time), and may or may not also be delayed release. Sustained release formulations are known in the art and are generally prepared by dispersing a drug within a matrix of a gradually degradable or hydrolyzable material, such as an insoluble plastic, a hydrophilic polymer, or a fatty compound. Alternatively, a solid dosage form may be coated with such a material.

Formulations for parenteral administration include aqueous and non-aqueous sterile injection solutions, which may further contain additional agents, such as anti-oxidants, buffers, bacteriostats, and solutes, which render the formulations isotonic with the blood of the intended recipient. The formulations may include aqueous and non-aqueous sterile suspensions, which contain suspending agents and thickening agents. Such formulations for patenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

The compounds according to the present invention may also be administered transdermally, wherein the active agent is incorporated into a laminated structure (generally referred to as a "patch") that is adapted to remain in intimate contact with the epidermis of the recipient for a prolonged period of time. Typically, such patches are available as single layer "drug-in-adhesive" patches or as multi-layer patches where the active agent is contained in a layer separate from the adhesive layer. Both types of patches also generally contain a backing layer and a liner that is removed prior to attachment to the skin of the recipient. Transdermal drug delivery patches may also be comprised of a reservoir underlying the backing layer that is separated from the skin of the recipient by a semi-permeable membrane and adhesive layer. Transdeimal drug delivery may occur through passive diffusion or may be facilitated using electrotransport or iontophoresis.

Formulations for rectal delivery of the compounds of the present invention include rectal suppositories, creams, ointments, and liquids. Suppositories may be presented as the active agent in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

The compounds of the formulas above may be formulated in compositions including those suitable for oral, buccal, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing a compound or prodrug of one of the formulas disclosed herein into association with a carrier that constitutes one or more accessory ingredients. In general, the compositions are prepared by bringing a compound or prodrug of the invention into association with a liquid carrier to form a solution or a suspension, or alternatively, bringing a compound or prodrug of the invention into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of the compound or prodrug of any one of the formulas disclosed herein contained in the formulation will vary depending the specific compound or prodrug selected, dosage form, target patient population, and other considerations, and will be readily determined by one skilled in the art. The amount of the compound or prodrug in the formulation will be that amount necessary to deliver a therapeutically effective amount of the compound to a patient in need thereof to achieve at least one of the therapeutic effects associated with the compounds or prodrugs of the invention. In practice, this will vary widely depending upon the particular compound or prodrug, its activity, the severity of the condition to be treated, the patient population, the stability of the formulation, and the like. Compositions will generally contain anywhere from about 1% by weight to about 99% by weight of a compound or prodrug of the invention, typically from about 5% to about 70% by weight, and more typically from about 10% to about 50% by weight, and will also depend upon the relative amounts of excipients/additives contained in the composition.

Combinations

In specific embodiments, active agents used in combination with compounds or prodrugs of the present invention comprise one or more compounds generally recognized as useful for treating the conditions discussed herein. In one embodiment, the use of two or more drugs, which may be of different therapeutic classes, may enhance efficacy and/or reduce adverse effects associated with one or more of the drugs.

For example, in certain embodiments, the present invention provides a method for treating pre-obesity and obesity, comprising a combination of a compound or prodrug of the present invention and one or more known antiobesity drugs.

Common therapeutic classes of obesity drugs include those that decrease food intake by either reducing appetite or increasing satiety, those that decrease nutrient absorption, and those that increase energy expenditure. In some embodiments, the compounds disclosed herein, either in a form according to any one of Formulas I, II, III, VI, VII, VIII, IX, or X or in prodrug form according to Formula IV or Formula V, may be used with one or more known antiobesity drugs. Examples of known antiobesity drugs include: phentermine, which is an appetite suppressant; topiramate, which is an depressant/epilepsy drug that has been shown to interfere with binge eating and may result in decreased weight and decreased blood pressure; Orlistat (Xenical, Alli®), which reduces intestinal fat absorption by inhibiting pancreatic lipase; Sibutramine (Reductil or Meridia), which is an anorectic or appetite suppressant; diethylpropion (diethylcathinone/amfepramone, also sold as Anorex,® Tenuate,® and Tepanil®), which is a stimulant marketed as an appetite suppressant (which functions as a prodrug for ethcathinone); Mazindol (Mazanor, Sanorex), which is a tetracyclic stimulant drug used for short-term treatment of obesity; Rimonabant (Acomplia), which is a recently developed medication that is a cannabinoid (CB1) receptor antagonist that acts centrally on the brain to decrease appetite and may also increase energy expenditure; metformin (glucophage) in people with diabetes mellitus type 2; and Exenatide (Byetta) and Pramlintide (Symlin), which both delay gastric emptying and promote a feeling of satiety. Other over-the-counter weight loss products including herbal remedies, laxatives, diet pills, diuretic drugs, and/or pyruvate may also be combined with the compounds and/or prodrugs disclosed herein. The compounds and prodrugs disclosed herein may also be used in combination with non drug-based therapy, including caloric restriction, exercise, and behavioral therapy.

In other embodiments, the present invention provides a method for treating depression comprising administering a combination of a compound or prodrug of the present invention and one or more known antidepressants. Antidepressants useful according to the invention comprise selective serotonin reuptake inhibitors (SSRIs), tricyclics, serotonin norepinephrine reuptake inhibitors (5-HT-NE dual reuptake inhibitors), and norepinephrine and dopamine reuptake inhibitors (NDRIs).

In one embodiment, compounds or prodrugs of the present invention may be combined with one or more compounds that are serotonin reuptake inhibitors. Serotonin reuptake inhibitors increase the extracellular level of the serotonin by inhibiting its reuptake into the presynaptic cell, which increases the level of serotonin available to bind to and stimulate the postsynaptic receptor. Examples of SSRIs include fluoxetine (PROZAC®) paroxetine (PAXIL®), sertraline (ZOLOFT®), citalopram (CELEXA®), escitalopram (LEXAPRO®), nefazodone (SERZONE®) and fluvoxamine (LUVOX®).

In another embodiment, compounds or prodrugs of the present invention may be combined with one or more compounds that at least partially inhibit the function of monoamine oxidase. Monoamine oxidase inhibitors (MAOIs) comprise a class of compounds understood to act by inhibiting the activity of monoamine oxidase, an enzyme generally found in the brain and liver of the human body, which functions to break down monoamine compounds, typically through deamination. There are two isoforms of monoamine oxidase inhibitors, MAO-A and MAO-B. The MAO-A isoform preferentially deaminates monoamines typically occurring as neurotransmitters (e.g., serotonin, melatonin, epinephrine, norepinephrine, and dopamine). Thus, MAOIs have been historically prescribed as antidepressants and for treatment of other social disorders, such as agoraphobia and social anxiety. The MAO-B isoform preferentially deaminates phenylethylamine and trace amines Dopamine is equally deaminated by both isofouns. The activity of MAOIs may be reversible or non-reversible and MAOIs may be selective for a specific isoform. For example, the MAOI moclobemide (also known as Manerix or Aurorix) is known to be approximately three times more selective for MAO-A than MAO-B. Any compound generally recognized as being an MAOI may be useful according to the present invention. Non-limiting examples of MAOIs useful in combination with compounds or prodrugs of the present invention for preparing compositions according to the invention include the following: isocarboxazid (MARPLAN®); moclobemide (Aurorix, Manerix, or Moclodura); phenelzine (NARDIL®); tranylcypromine (PARNATE®); selegiline (ELDEPRYL®, EMSAM®, or 1-deprenyl); lazabemide; nialamide; iproniazid (marsilid, iprozid, ipronid, rivivol, or propilniazida); iproclozide; toloxatone; harmala; brofaromine (Consonar); benmoxin (Neuralex); and certain tryptamines, such as 5-MeO-DMT (5-Methoxy-N, N-dimethyltryptamine) or 5-MeO-AMT (5-methoxy-α-methyltryptamine).

According to still another embodiment of the invention, compounds or prodrugs of any one of the formulas disclosed herein may be combined with one or more compounds that are norepinephrine reuptake inhibitors (NRIs). NRIs are also known as noradrenaline reuptake inhibitors (NARIS) and generally function to elevate the level of norepinephrine in the central nervous system (CNS) by inhibiting reuptake of norepinephrine from the synaptic cleft into the presynaptic neuronal terminal. Norepinephrine is a catecholamine and phenylethylamine that functions as a neurotransmitter and is known to affect many conditions. Any compound typically recognized as inhibiting the reuptake of norepinephrine in the CNS can be used according to the present invention. Non-limiting examples of NRIs useful according to the invention comprise atomoxetine (STRATTERA®), reboxetine (EDRONAX®, VESTRA®, or NOREBOX®), viloxazine (EMOVIT®, VIVALAN®, VIVARINT®, or VIVILAN®), maprotiline (DEPRILEPT®, LUDIOMIL®, or PSYMION®), bupropion (WELLBUTRIN® or ZYBAN®), and radafaxine.

Further non-limiting examples of specific antidepressants useful according to the invention include tricyclics such as amitriptyline, nortriptyline, and desipramine; serotonin-norepinephrine reuptake inhibitors such as venlafaxine (EFFEXOR®), duloxetine (CYMBALTA®), and milnacipran; tetracyclics such as maprotiline and mirtazapine; and other classes of compounds, including triazolopyridines such as trazodone.

The above compounds and classes of compounds are only examples of the types of active agents that can be used in combination with a compound or prodrug of the present invention for the treatment of mood disorders, sleep disorders, or attention deficit disorders and are not intended to be limiting of the invention. Rather, various further active agents can be combined with one or more compounds of the present invention according to the invention. For example, any drug generally recognized as being an antidepressant, antinarcoleptic, or ADHD treatment can be used in combination with one or more compounds of the present invention. Moreover, it is possible according to the invention to combine two or more additional active agents with one or more compounds or prodrugs of the present invention for treatment of the noted conditions.

Non-limiting examples of further active agents that can be combined with compounds of the present invention include: mood stabilizers (such as lithium, olanzipine, verapamil, quetiapine, lamotrigine, carbamazepine, valproate, oxcarbazepine, risperidone, aripiprazole, and ziprasidone); antipsychotics (such as haloperidol and other butyrophenones, chlorpromazine, fluphenazine, perphenazine, prochlorperazine, and other phenothiazines, and clozapine); serotonin receptor antagonist (5-HT2 and 5-HT3 antagonists) (such as ondansetron, tropisetron, katenserin, methysergide, cyproheptadine, and pizotifen); serotonin receptor agonists (5-HT1A receptor agonists) (such as buspirone); stimulants [such as caffeine, ADDERALL®, methylphenidate (METADATE®, RITALIN®, or CONCERTA®), pemoline (CYLERT®), or modafinil (PROVIGIL®)]; and gamma-hydroxybutyrate (GHB) (XYREM®). Although the above compounds are described in terms of classes of compounds and specific compounds, it is understood that there is substantial overlap between certain classes of compounds (such as between mood stabilizers, antipsychotics, antidepressants, and serotonin receptor antagonists). Thus, specific compounds exemplifying a specific class of compounds may also properly be identified with one or more further classes of compounds. Accordingly, the above classifications should not be viewed as limiting the scope of the types of compounds useful in combination with compounds and prodrugs of the present invention for treating the conditions described herein.

Since the compounds and prodrugs of the present invention may also be useful in the treatment of stimulant (e.g., cocaine and/or methamphetamine) addiction, they may be combined with other drugs for the treatment of addiction. For example, drugs that are commonly used for the treatment of methamphetamine addiction include, but are not limited to, bupropion, modafinil, Ibogaine, Mirtzapine, dextroamphetamine, monoamine reuptake inhibitors (such as indatraline, fluoxetine, bupropion and imipramine), and amino acids. Although cocaine replacement therapies to treat addiction are being researched, there is currently no FDA-approved treatment for cocaine addiction.

Combinations of compounds or prodrugs of the present invention with other therapeutic agents are also included in the present invention, wherein the condition to be treated is any condition that may be responsive to the inhibition of dopamine, serotonin and/or norepinephrine reuptake.

The compound or prodrug of any of the formulas disclosed herein and the one or more other therapeutic agents may be contained within a single composition or alternatively may be administered concurrently or sequentially (consecutively) in any order. For sequential administration, each of the compound or prodrug of the formulas disclosed herein and the one or more other therapeutic agents can be formulated in its own pharmaceutical composition, each of which is to be administered sequentially, in any order. Alternatively, the compound or prodrug of the formulas disclosed herein and the one or more other therapeutic agents can be formulated together. The compositions may be formulated for oral, systemic, topical, intravenous, intraparenteral, intravaginal, intraocular, transbuccal, transmucosal, or transdermal administration.

Methods of Use

In a further embodiment, the present invention provides a method for treating or delaying the progression of disorders that are alleviated by the modulation of neurotransmitter levels in a patient, the method comprising administering a therapeutically effective amount of at least one compound or prodrug of the formulas disclosed herein to the patient.

In particular, the present invention relates to the field of treating pre-obesity and obesity in animals, particularly humans and other mammals, and associated effects of these conditions. It may also relate to the treatment of other conditions that may benefit from modulation of neurotransmitter levels. For example, it may relate to treatment of depression and associated disorders, as well as cocaine and/or methamphetamine addictions. It may particularly relate to the treatment of conditions that may benefit from the release and/or reuptake inhibition of one or more of dopamine, norepinephrine, and serotonin. In some embodiments, the compounds and prodrugs of the present invention are selective for one or more monoamine transporter. In some embodiments, the compounds bind more strongly to the dopamine and/or serotonin transporters than to the norepinephrine transporters.

In some embodiments, the present invention may relate to the use of compounds or prodrugs of the present invention to treat diseases that are responsive to the modulation of the level of one or more monoamine neurotransmitter. For example, in some embodiments, the invention provides for the use of compounds or prodrugs of the present invention to treat diseases responsive to one or more of dopamine, serotonin, and/or norepinephrine release. In some embodiments, the invention provides for the use of compounds or prodrugs of the present invention to treat diseases responsive to dopamine release. In some embodiments, the invention provides for the use of compounds or prodrugs of the present invention to treat diseases responsive to joint dopamine and serotonin release. In some embodiments, the invention provides for the use of compounds or prodrugs of the present invention to treat diseases responsive to one or more of dopamine, serotonin, and/or norepinephrine uptake inhibition. In certain embodiments, the invention provides for the use of compounds or prodrugs of the present invention to treat diseases responsive to a combination of monamine neurotransmitter release and uptake inhibition. For example, in some embodiments, the invention provides for the use of compounds or prodrugs of the present invention to treat diseases responsive to dopamine and norepinephrine release and/or serotonin uptake inhibition.

Obesity has its common meaning, e.g., the medical condition that exists when an individual has accumulated excess body fat, which may lead to a variety of related health problems, and which is characterized by a body mass index (BMI) of 30 $kg/m^2$ or more. Pre-obesity, also known as overweight, refers to the condition wherein an individual's BMI is between 25 $kg/m^2$ and 30 $kg/m^2$.

Addiction has its common meaning, e.g., the condition that exists when an individual persists in the use of a substance despite impairment or distress related to the use of the substance. In preferred embodiments, the compounds and prodrugs of the present invention show a slow onset and long duration of activity. These features make the compounds and prodrugs of the present invention particularly suitable for the treatment of addiction to abused substances, which commonly exhibit a fast onset and/or short duration of activity. Administration of compounds or prodrugs of the present invention to subjects with addiction to one or more substances may be particularly suited for the treatment of cocaine, methamphetamine, and nicotine addiction.

The compounds and prodrugs of the present invention may also be applicable to treating depression and depressive conditions in animals, particularly humans and other mammals, and associated effects of these conditions. Depression has its common meaning, e.g., a common mental disorder that presents with depressed mood, loss of interest or pleasure, feelings of guilt or low self-worth, disturbed sleep or appetite, low energy, and poor concentration or a mental state characterized by a pessimistic sense of inadequacy and a despondent lack of activity. Physical changes, such as insomnia, anorexia, weight loss, and decreased energy and libido can also occur as a result of depression. Depression includes dysthymic disorder or dysthymia, defined as a chronic low-grade depression and major depression as well as other stages or levels of depression. It also includes post-partum depression.

The compounds or prodrugs of the present invention may also be used for other conditions that may be responsive to release or inhibition of reuptake of one or more type of neurotransmitter. In some embodiments, the compounds or prodrugs may be used to treat patients for conditions that are responsive to the release or uptake inhibition of dopamine, norepinephrine, and/or serotonin. For example, in some embodiments, compounds or prodrugs of the present invention may be used to treat patients with bipolar disorder, attention deficit disorder (ADD), attention-deficit/hyperactivity disorder (ADHD), hypoactive sexual desire disorder, antidepressant-induced sexual dysfunction, orgasmic dysfunction, seasonal affective disorder/winter depression, obesity and food addiction, mania, bulimia and other eating disorders, panic disorders, obsessive compulsive disorder, schizophrenia, schizo-affective disorder, Parkinson's disease, narcolepsy, anxiety disorders, insomnia, chronic pain, migraine headaches, and restless legs syndrome.

The method of treatment generally includes administering a therapeutically effective amount of a compound or prodrug of a formula disclosed herein, optionally in a pharmaceutical composition including one or more pharmaceutically acceptable carriers. The therapeutically effective amount is preferably sufficient to cause the release of one or more neurotransmitter and/or inhibit the uptake of one or more neurotransmitter. The therapeutically effective amount is further preferably sufficient to cause some relief to the patient in the symptoms of the disorder for which the patient is being treated.

For example, in one embodiment, a method of treating pre-obesity or obesity is provided. In such methods, a therapeutically effective amount of a compound or prodrug of the present invention to treat a patient with pre-obesity or obesity may be that amount capable of effecting the release and/or reuptake of one or more monoamine neurotransmitter. Such compound or prodrug may cause the patient to experience decreased appetite and/or may create a sensation of fullness. The method of treating pre-obesity or obesity may be used to attain or maintain a patient's weight loss.

In another embodiment, a method of treating cocaine addiction is provided. In such methods, a therapeutically effective amount of a compound or prodrug of the present invention to treat a patient with cocaine addiction may be that amount capable of exerting some dopaminergic effect. Cocaine functions by inhibiting the reuptake of dopamine by blocking the dopamine transporter that transports excess dopamine back into the presynaptic cell. It has a fast onset of activity and short duration. Chronic cocaine use produces a withdrawal syndrome that is associated with depletion of dopamine and deficits in dopaminergic signaling By providing a compound or prodrug of the present invention with slow onset and long duration of activity, the compound or prodrug may be able to reverse dopaminergic deficits in chronic cocaine users.

In another embodiment, a method of treating depression is provided. A therapeutically effective amount of a compound or prodrug of the present invention to treat a patient with depression may be that amount capable of providing some relief from symptoms such as changes in mood, feelings of intense sadness and despair, mental slowing, loss of concentration, pessimistic worry, agitation, and self-deprecation and/or from physical changes such as insomnia, anorexia and weight loss, and decreased energy and libido. The levels of one or more of dopamine, norepinephrine, and serotonin may be low in subjects with depression and thus, increase in the release of or inhibition of the uptake of any of these monoamines by the appropriate transporter may be effective to adjust the monoamine levels and treat the symptoms of depression.

The therapeutically effective dosage amount of any specific formulation will vary somewhat from drug to drug, patient to patient, and will depend upon factors such as the condition of the patient and the route of delivery. When administered conjointly with other pharmaceutically active agents, even less of the compound or prodrug of the invention may be therapeutically effective. Furthermore, the therapeutically effective amount may vary depending on the specific condition to be treated.

The compound or prodrug of the invention can be administered once or several times a day or according to any other intermittent administration schedule. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation.

The compounds and prodrugs of the invention may be used with other types of therapy, including those which are non-drug based. For example, obesity is commonly treated using one or more therapeutics in combination with behavioral treatment (e.g., diet and exercise changes), which may lead to a better outcome than using a drug alone. Depression is commonly treated with some combination of therapeutics and some sort of psychotherapy. Thus, in some embodiments, the methods of the present invention comprise administering to a subject a compound or prodrug of the invention that that is capable of modulating neurotransmitter levels in conjunction with one or more other types of non-drug-based therapy.

EXAMPLES

Certain compounds in the Examples Section are referred to with an alphanumerical designation. The compound structure for these compounds can be found, for example, in the specific synthesis examples, Schemes 1-3, or in the data tables provided herein.

Example 1

Representative Preparation of Compounds of the Present Invention Preparation of PAL-583

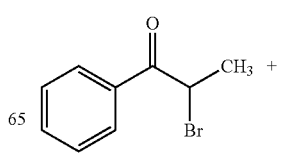

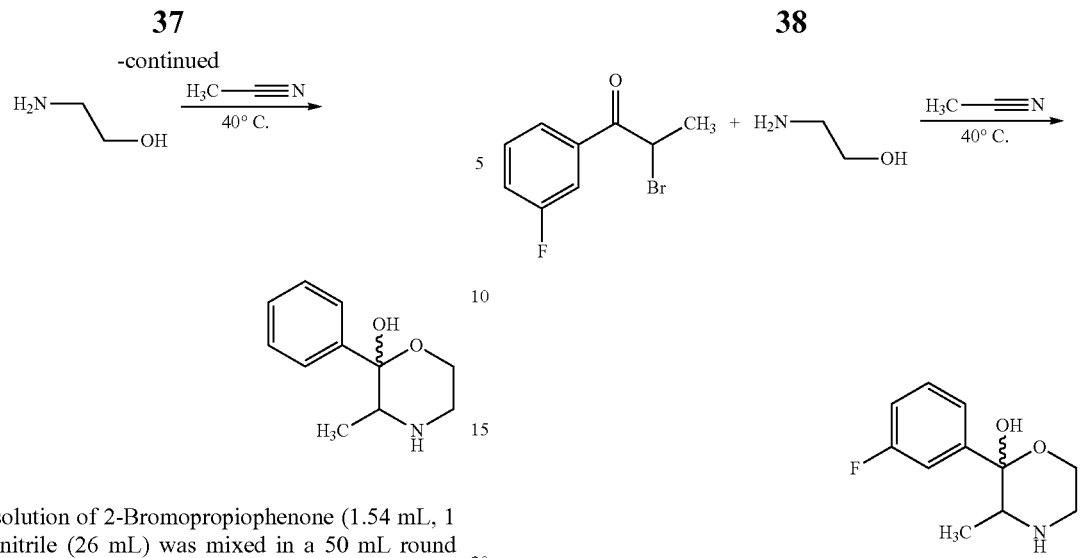

A 0.4 M solution of 2-Bromopropiophenone (1.54 mL, 1 eq) in acetonitrile (26 mL) was mixed in a 50 mL round bottom flask under $N_2$ (g). Ethanolamine (1.25 mL, 2 eq) was added changing the color of solution from olive green to amber and forming a precipitate. The reaction was refluxed at 40° C. for 3.5 hrs and then cooled to room temperature to stir overnight. The next morning the orange-yellow mixture with precipitate was refluxed at 40° C. for 2 hrs. After cooling to room temperature the reaction was diluted with ethylacetate, washed with saturated sodium bicarbonate (2×50 mL), water (2×50 mL), brine (2×50 mL), and then dried over anhydrous sodium sulfate. After filtration the volatiles were removed under reduced pressure affording 0.807 g (40%) of crude product. Purified on 12 g column (ISCO) using a system of chloroform (A)/9:1 methanol:ammonium hydroxide (B) with a 20-30% gradient (B). Fractions 8-10 were collected and concentrated under reduced pressure affording 0.351 g (18%) of purified product. The free base was salted with 0.2108 g of fumaric acid and recrystalized using methanol/ether yielding 0.2135 g of final product.

Preparation of PAL-587

A 0.4 M solution of 2-bromo-1-(3-fluorophenyl)propan-1-one (3.05 g, 1 eq) in acetonitrile (33 mL) was mixed in a 100 mL round bottom flask under $N_2$ (g). Ethanolamine (1.6 mL, 2 eq) was added and stirred/refluxed for 6 hrs at 40° C. After cooling to room temperature overnight the volatiles were removed under reduced pressure, the residue was then taken up in ethyl acetate, washed with saturated sodium bicarbonate (3×50 mL), brine (2×50 mL), and dried over anhydrous sodium sulfate. After filtration the volatiles were removed under reduced pressure affording 1.464 g (53%) of crude product. Purified on 12 g column (ISCO) using a system of methylene chloride (A)/methanol (B) with a 20-30% gradient (B). Fractions 13-32 were collected and concentrated under reduced pressure affording 0.638 g (23%) of purified product. The free base was salted with 0.3506 g of fumaric acid and recrystalized using methanol/ethyl acetate yielding 0.5672 g of final product.

Preparation of PAL-589

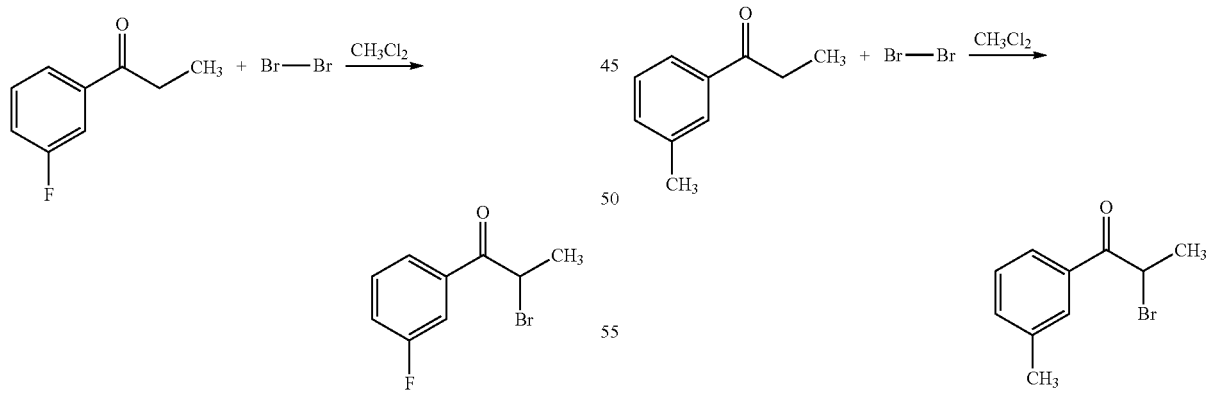

1-(3-fluorophenyl)propan-1-one (4.53 g, 1 eq) and bromine (1.53 mL, 1 eq) were combined and stirred in 50 mL of methylene chloride overnight at room temperature. The next day the mixture was washed with water (4×50 mL), brine (2×50 mL), and dried over anhydrous sodium sulfate. After filtration the volatiles were removed under reduced pressure affording 6.435 g (94%) of crude 2-bromo-1-(3-fluorophenyl)propan-1-one.

1-(3-methylphenyl)propan-1-one (8.746 g, 1 eq) and bromine (3.04 mL, 1 eq) were combined and stirred in 100 mL of methylene chloride overnight at room temperature. The next day the mixture was washed with water (4×50 mL), brine (2×50 mL), and dried over anhydrous sodium sulfate. After filtration the volatiles were removed under reduced pressure affording 12.923 g (96%) of crude 2-bromo-1-(3-methylphenyl)propan-1-one.

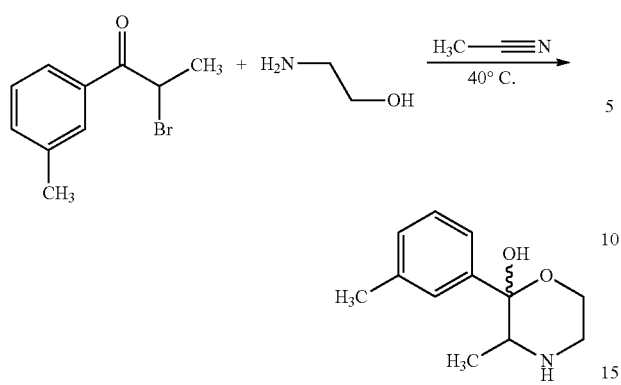

A 0.4 M solution of 2-bromo-1-(3-methylphenyl)propan-1-one (6.57 g, 1 eq) in acetonitrile (72 mL) was mixed in a 250 mL round bottom flask under N₂ (g). Ethanolamine (3.5 mL, 2 eq) was added and stirred/refluxed for 6 hrs at 40° C. After cooling to room temperature overnight the volatiles were removed under reduced pressure, the residue was then taken up in ethyl acetate, washed with saturated sodium bicarbonate (3×50 mL), brine (2×50 mL), and dried over anhydrous sodium sulfate. After filtration the volatiles were removed under reduced pressure affording 3.777 g (63%) of crude product. Purified on 12 g column (ISCO) using a system of methylene chloride (A)/methanol (B) with a 20-30% gradient (B). Product fractions were collected and concentrated under reduced pressure affording 1.183 g (20%) of purified product. The free base was salted with 0.6624 g of fumaric acid and recrystalized using methanol/ethyl acetate, yielding 0.3459 g of final product.

Preparation of PAL-590

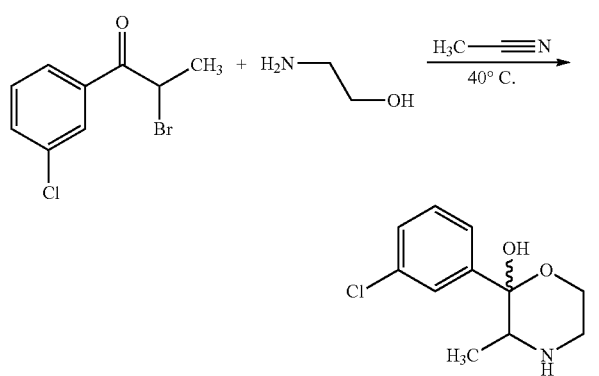

A 0.4 M solution of 2-bromo-1-(3-chlorophenyl)propan-1-one (4.22 g, 1 eq) in acetonitrile (43 mL) was mixed in a 100 mL round bottom flask under N₂ (g). Ethanolamine (2.05 mL, 2 eq) was added and stirred/refluxed for 6 hrs at 40° C. After cooling to room temperature overnight the volatiles were removed under reduced pressure, the residue was then taken up in ethyl acetate, washed with saturated sodium bicarbonate (3×50 mL), brine (2×50 mL), and dried over anhydrous sodium sulfate. After filtration the volatiles were removed under reduced pressure affording 3.319 g (70%) of crude product. Purified on 12 g column (ISCO) using a system of methylene chloride (A)/methanol (B) with a 20-30% gradient (B). Product fractions were collected and concentrated under reduced pressure affording 0.970 g (20%) of purified product. The free base was salted with 0.4054 g of fumaric acid and recrystalized using methanol/ethyl acetate, yielding 0.7213 g of final product.

Preparation of PAL-592

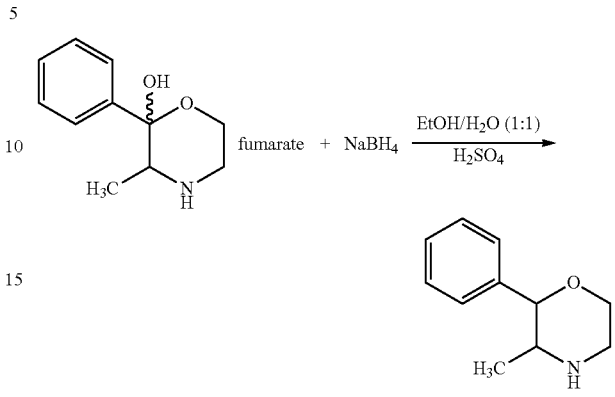

A solution of 3-methyl-2-phenylmorpholin-2-ol fumarate salt (0.4646 g, 1 eq) in 1:1 ethanol:water (3.6 mL) was chilled to 0° C. under N₂ (g). With constant stirring, a solution of sodium borohydride (0.2278 g, 4 eq) in water (2.5 mL) was added drop wise. The reaction was allowed to warm to room temperature and stir overnight. The next morning the reaction was chilled to 0° C. and 2.2 mL of concentrated hydrochloric acid was added drop wise. The ethanol was then removed under reduced pressure and the crude mixture was diluted with water, chilled to 0° C., made basic by adding 40% aqueous sodium hydroxide (tested with litmus), extracted with methylene chloride (3×25 mL), dried over anhydrous sodium sulfate, filtered, and volatiles removed under reduced pressure to afford 0.200 g of solid residue. The intermediate residue dissolved in methylene chloride was then added drop wise to 4.8 mL of concentrated sulfuric acid at 0° C. and stirred overnight. The next morning the reaction was poured into ice water, the layers were separated, and the aqueous layer was chilled to 0° C. The aqueous layer was then made basic with 40% aqueous sodium hydroxide (tested with litmus), extracted with methylene chloride (3×25 mL), dried over anhydrous sodium sulfate, filtered, and volatiles removed under reduced pressure to afford 0.172 g of oil. The oil was then dissolved in methylene chloride and 0.0681 g of fumaric acid in methanol was added to form the fumarate salt of the product. Anal. Calcd for 2[$C_{11}H_{15}CNO$] [$C_4H_4O_4$]: C, 66.36; H, 7.28; N, 5.95. Found: C, 66.12; H, 7.29; N, 5.85. 1H NMR (300 MHz, MeOH) δ ppm 1.01 (d, J=6.78 Hz, 3H) 3.20-3.41 (m, 3H) 3.84-3.99 (m, 1H) 4.13 (d, J=14.32 Hz, 1H) 4.32 (d, J=10.17 Hz, 1H) 6.70 (s, 1H) 7.39 (s, 5H).

Preparation of PAL-593

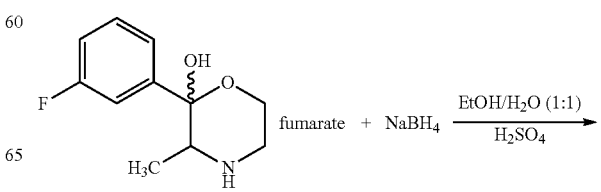

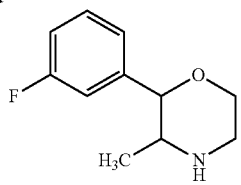

A solution of 2-(3-fluorophenyl)-3-methylmorpholin-2-ol fumarate salt (0.4326 g, 1 eq) in 1:1 ethanol:water (3.3 mL) was chilled to 0° C. under N₂ (g). With constant stirring, a solution of sodium borohydride (0.2000 g, 4 eq) in water (2.2 mL) was added drop wise. The reaction was allowed to warm to room temperature and stir overnight. The next morning the reaction was chilled to 0° C. and 1.9 mL of concentrated hydrochloric acid was added drop wise. The ethanol was then removed under reduced pressure and the crude mixture was diluted with water, chilled to 0° C., made basic by adding 40% aqueous sodium hydroxide (tested with litmus), extracted with methylene chloride (3×25 mL), dried over anhydrous sodium sulfate, filtered, and volatiles removed under reduced pressure to afford 0.176 g of clear oil. The inteimediate oil dissolved in methylene chloride was then added drop wise to 1.9 mL of concentrated sulfuric acid at 0° C. and stirred overnight. The next morning the reaction was poured into ice water, the layers were separated, and the aqueous layer was chilled to 0° C. The aqueous layer was then made basic with 40% aqueous sodium hydroxide (tested with litmus), extracted with methylene chloride (3×25 mL), dried over anhydrous sodium sulfate, filtered, and volatiles removed under reduced pressure to afford 0.168 g of oil. The oil was then dissolved in methylene chloride and 0.0626 g of fumaric acid in methanol was added to form the fumarate salt of the product. Anal. Calcd for 2[C₁₁H₁₄CFNO] [C₄H₄O₄]: C, 61.65; H, 6.37; N, 5.53. Found: C, 61.67; H, 6.36; N, 5.53. ¹H NMR (300 MHz, METHANOL-d₄) δ ppm 0.96 (d, J=6.78 Hz, 3H) 3.04-3.17 (m, 1H) 3.17-3.24 (m, 1H) 3.26 (m, 1H) 3.83 (t, J=11.11 Hz, 1H) 4.09 (d, J=11.68 Hz, 1H) 4.23 (d, J=9.42 Hz, 1H) 6.68 (s, 1H) 7.03-7.24 (m, 3H) 7.39 (dd, J=7.91, 7.16 Hz, 1H).

Preparation of PAL-594

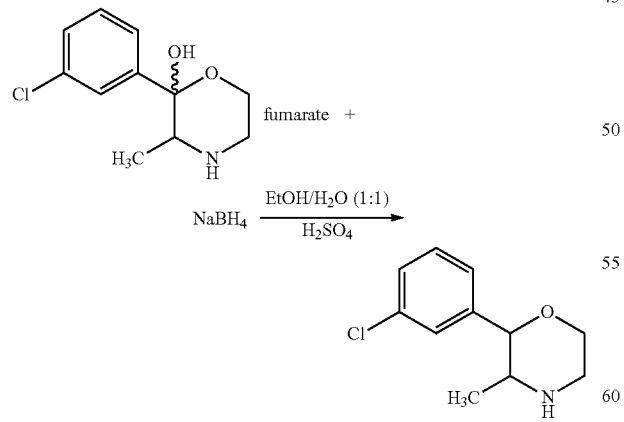

A solution of 2-(3-chlorophenyl)-3-methylmorpholin-2-ol fumarate salt (0.3884 g, 1 eq) in 1:1 ethanol:water (2.8 mL, plus methanol drop wise till dissolved) was chilled to 0° C. under N₂ (g). With constant stirring, a solution of sodium borohydride (0.1710 g, 4 eq) in water (1.8 mL) was added drop wise. The reaction was allowed to warm to room temperature and stir overnight. The next morning the reaction was chilled to 0° C. and 1.7 mL of concentrated hydrochloric acid was added drop wise. The ethanol was then removed under reduced pressure and the crude mixture was diluted with water, chilled to 0° C., made basic by adding 40% aqueous sodium hydroxide (tested with litmus), extracted with methylene chloride (3×25 mL), dried over anhydrous sodium sulfate, filtered, and volatiles removed under reduced pressure to afford 0.247 g of white solid. The solid intermediate dissolved in methylene chloride was then added drop wise to 5.1 mL of concentrated sulfuric acid at 0° C. and stirred overnight. The next morning the reaction was poured into ice water, the layers were separated, and the aqueous layer was chilled to 0° C. The aqueous layer was then made basic with 40% aqueous sodium hydroxide (tested with litmus), extracted with methylene chloride (3×25 mL), dried over anhydrous sodium sulfate, filtered, and volatiles removed under reduced pressure to afford 0.245 g of oil. The oil was then dissolved in methylene chloride and 0.0868 g of fumaric acid in methanol was added to form the fumarate salt of the product. Anal. Calcd for 2[C₁₁H₁₄ClNO] [C₄H₄O₄]: C, 57.89; H, 5.98; N, 5.19. Found: C, 57.75; H, 5.88; N, 5.10.

¹H NMR (300 MHz, MeOH) δ ppm 1.06 (d, J=6.78 Hz, 3H) 3.17-3.28 (m, 1H) 3.27-3.35 (m, 1H) 3.34-3.39 (m, 1H) 3.93 (t, J=11.87 Hz, 1H) 4.19 (d, J=12.43 Hz, 1H) 4.32 (d, J=9.80 Hz, 1H) 6.79 (s, 1H) 7.37-7.44 (m, 1H) 7.47 (d, J=5.27 Hz, 1H) 7.53 (s, 1H).

Example 2

Preparation of Additional Compounds
Representative Preparation

Step 1: Preparation of N-Benzyl-N-(2'-hydroxyethyl)-1-methyl-2-oxo-2-tolylethylamine

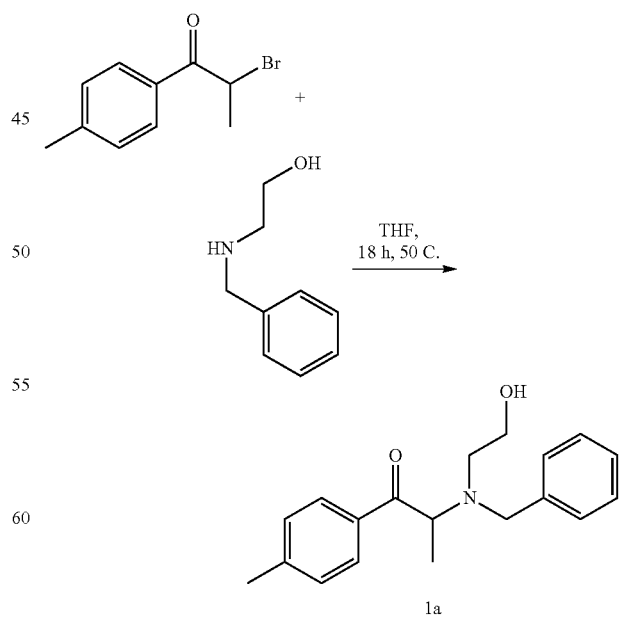

A solution of 2-bromo-2'-acetonaphthone (3 g, 12 mmol) and 2-benzylaminoethanol (3.64 g, 24.1 mmol) in THF (50 mL) was stirred 18 h at 50 C. The mixture was concentrated and taken up into ethyl acetate and washed with saturated aqueous NaHCO$_3$, water and brine. The organics were dried (MgSO$_4$), concentrated and purified by automated flash chromatography (silica gel, 4/1 hexane/ethyl acetate) to yield 4.93 g (84%) of 1a as a white solid. $^1$H NMR (CDCl$_3$ 300 MHz) δ 7.52-7.11 (m, 9H), 4.17-4.13 (m, 2H), 3.66-3.59 (m, 3H), 2.84-2.65 (m, 2H), 2.43-2.33 (m, 4H), 0.96-0.79 (m, 3H); APCI-MS, calculated for C$_{19}$H$_{23}$NO$_2$ (M+H)$^+$ 298.4; observed 298.4.

Step 2: Preparation of N-Benzyl-N-(2'-hydroxyethyl)-2-hydroxy-1-methyl-2-tolylethylamine

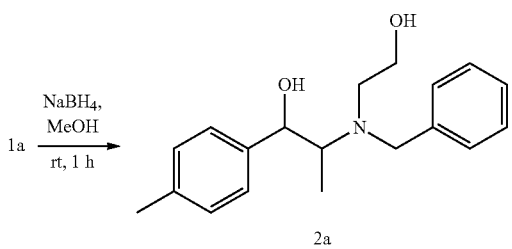 [SMILES: Cc1ccc(C(O)C(C)N(CCO)Cc2ccccc2)cc1]

A solution of 1a (4.9 g, 16.5 mmol) in MeOH (150 mL) was treated with NaBH$_4$ (0.69 g, 18.1 mmol) and the reaction stirred for 1 h at room temperature. The mixture was concentrated and the residue was taken up into ethyl acetate and washed with saturated aqueous NaHCO$_3$, water and brine. The organic phase was dried (MgSO$_4$) and concentrated to generate a quantitative amount of colorless oil (2a), which required no further purification. $^1$H NMR (CDCl$_3$ 300 MHz) δ 7.38-7.09 (m, 9H), 4.33 (d, 1H, J=9 Hz), 3.94 (d, 1H, J=15 Hz), 3.70-3.62 (m, 2H), 3.49 (d, 1H, J=12 Hz), 2.87-2.83 (m, 2H), 2.67-2.58 (m, 1H), 2.32 (s, 3H), 0.83-0.80 (m, 3H); APCI-MS, calculated for C$_{19}$H$_{25}$NO$_2$ (M+H)$^+$ 300.4; observed 300.5.

Step 3: Preparation of N-Benzyl-3-methyl-2-tolylmorpholine

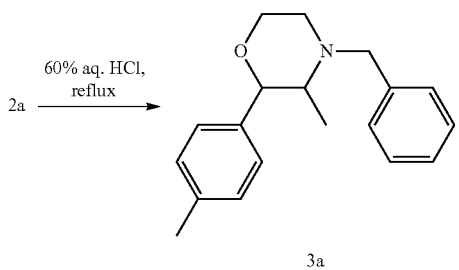 [SMILES: Cc1ccc(C2OCCN(Cc3ccccc3)C2C)cc1]

A suspension of 2a (4.9 g, 16.5 mmol) in 60% (v/v) of aqueous HCl solution (150 mL) was introduced to a glass reactor and sealed with a Teflon cap and was heated to 105 C for 18 h. The mixture was made alkaline with solid KOH and extracted with ethyl acetate. The organic phase was washed with brine, dried (MgSO$_4$) and concentrated to yield 5.13 g of brown oil. This crude material was purified by automated flash chromatography (silica gel, 1/1 hexanes/ethyl acetate) to obtain 1.86 g (40%) of pale orange solid (3a). $^1$H NMR (CDCl$_3$ 300 MHz) δ 7.34-7.23 (m, 8H), 7.15 (d, 1H, J=9 Hz), 4.21-4.10 (m, 2H), 3.85-3.74 (m, 2H), 3.18 (d, 1H, J=15 Hz), 2.68-2.64 (m, 1H), 2.51-2.38 (m, 2H), 2.34 (s, 3H), 0.97 (d, 3H, J=6 Hz); ESI-MS, calculated for C$_{19}$H$_{25}$NO (M+H)$^+$282.4; observed 282.4.

Step 4: Preparation of 3-Methyl-2-(4'-Tolyl)morpholine fumarate (PAL 747)

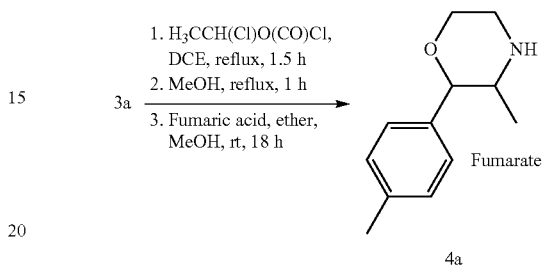

A solution of 3a (1.86 g, 6.61 mmol) and 1-chloroethyl chloroformate (0.95 mL, 8.72 mmol) in DCE (30 mL) was refluxed for 1.5 h and then concentrated. The residue was dissolved in MeOH (30 mL) and refluxed for 1 h. The mixture was concentrated again and this residue was taken up into ethyl acetate and washed with saturated aqueous NaHCO$_3$, water and brine, dried (MgSO$_4$) and concentrated. The crude product was purified by automated flash chromatography (silica gel, 10% MeOH/DCM) to yield 572 mg (45%) of pale yellow solid. An initial attempt was made to isolate the hydrochloride salt, but if it wouldn't crystallize, the mixture was neutralized and the fumarate salt was formed. After several recrystallization attempts, 66 mg (9%) of pure 4a was obtained. $^1$H NMR (D$_2$O 300 MHz) δ 7.20 (d, 2H, J=9 Hz), 7.15 (d, 2H, J=9 Hz), 3.97 (d, 1H, J=9 Hz), 3.89-3.85 (m, 2H), 2.98-2.81 (m, 3H), 2.29 (s, 3H), 0.73 (d, 3H, J=6 Hz); ESI-MS, calculated for C$_{12}$H$_{17}$NO (M+H)$^+$ 192.3; observed 192.1; Anal. Calculated for C$_{14}$H$_{19}$NO$_3$ (with 0.2 mol of water): C, 66.49; H, 7.73; N, 5.54. Found: C, 66.14; H, 7.46; N, 5.31.

The following compounds were prepared based on the above procedure (Steps 1-4) with the indicated modifications. Characterization data for representative compounds of the present invention is presented below.

3-Methyl-2-(4'-Tolyl)morpholine $^1$H NMR (CDCl$_3$ 300 MHz) δ 7.23-7.16 (m, 4H), 4.41 (d, 1H, J=12 Hz), 4.14-4.09 (m, 2H), 3.30-3.19 (m, 3H), 2.35 (s, 3H), 1.19 (d, 3H, J=9 Hz).

2-(2'-Naphthyl)morpholine hydrochloride (4b, PAL 703)

The product of the de-benzylation step was recrystallized from methanol/ether to yield a white solid in 86% yield (1.34 g); $^1$H NMR (d$_6$-DMSO, 300 MHz) δ 9.38 (br s, 2H), 7.97-7.93 (m, 4H), 7.58-7.51 (m, 3H), 4.93 (d, 1H, J=9 Hz), 4.19-4.15 (m, 1H), 3.98-3.97 (m, 1H), 3.54-3.50 (m, 1H), 3.41-3.28 (m, 1H), 3.20-3.06 (m, 2H); ESI-MS, calculated for C$_{14}$H$_{15}$NO (M+H)$^+$214.3; observed 214.1; Anal. Calculated (with 0.1 mol water) for C$_{14}$H$_{16}$ClNO; C, 66.84; H, 6.49; N, 5.57. Found: C, 66.75; H, 6.50; N, 5.47.

3-Methyl-2-(2'-Naphthyl)morpholine hydrochloride (4c, PAL 704)

The product of the de-benzylation step was recrystallized from methanol/ether to yield a white solid in 7% yield (29 mg); $^1$H NMR (CD$_3$OD, 300 MHz) δ 7.95-7.89 (m, 4H), 7.56-7.53 (m, 3H), 4.59 (d, 1H, J=9.9 Hz), 4.25-4.24 (m, 1H), 4.11-3.96 (m, 1H), 3.58-3.45 (m, 3H), 1.10 (d, 3H, J=6.9 Hz); ESI-MS, calculated for C$_{15}$H$_{17}$NO (M+H)$^+$ 228.3; observed 228.1; Anal. Calculated (with 0.2 mol water) for C$_{15}$H$_{18}$ClNO; C, 67.39; H, 6.94; N, 5.24. Found: C, 67.40; H, 6.85; N, 5.26.

3-Methyl-[(4'-Fluoro)-2-Phenyl]morpholine (0.5 fumarate) (4d, PAL 748)

The product was isolated as a white solid in 39% yield (99 mg); $^1$H NMR (CD$_3$OD, 300 MHz) δ 7.43-7.37 (m, 2H), 7.11 (t, 2H, J=9 Hz), 4.24 (d, 1H, J=9 Hz), 4.07 (d, 1H, J=3 Hz), 3.85-3.83 (m, 1H), 3.27-3.14 (m, 3H), 0.95 (d, 3H, J=6 Hz); ESI-MS, calculated for C$_{11}$H$_{14}$FNO (M+H)$^+$196.2; observed 196.3; Anal. Calculated for C$_{13}$H$_{16}$FNO$_3$; C, 61.65; H, 6.38; N, 5.53; F, 7.50. Found: C, 61.92; H, 6.38; N, 5.51; F, 7.28.

3-Methyl-[(4'-Fluoro)-2-Phenyl]morpholine $^1$H NMR (CDCl$_3$ 300 MHz) δ 7.34-7.30 (m, 2H), 7.11-7.05 (m, 2H), 4.49 (d, 1H, J=9 Hz), 4.18-4.11 (m, 2H), 3.38-3.18 (m, 3H), 1.23 (d, 3H, J=6 Hz).

3-Methyl-[(4'-Chloro)-2-Phenyl]morpholine (0.5 fumarate) (4e, PAL 749)

The product was isolated as a white solid in 27% yield (74 mg); $^1$H NMR (CD$_3$OD, 300 MHz) δ 7.39-7.36 (m, 4H), 6.68 (s, 1H), 4.27 (d, 1H, J=12 Hz), 4.11 (d, 1H, J=3 Hz), 3.91-3.82 (m, 1H), 3.29-3.18 (m, 3H), 0.99 (d, 3H, J=9 Hz); ESI-MS, calculated for C$_{11}$H$_{14}$ClNO (M+H)$^+$212.7; observed 212.0; Anal. Calculated (with 0.4 mol water) for C$_{13}$H$_{16}$ClNO$_3$; C, 56.38; H, 6.12; N, 5.06. Found: C, 56.32; H, 5.78; N, 4.77.

3-Methyl-[(4'-Chloro)-2-Phenyl]morpholine $^1$H NMR (CDCl$_3$ 300 MHz) δ 7.37-7.33 (m, 2H), 7.29-7.27 (m, 2H), 4.36 (d, 1H, J=9 Hz), 4.12-4.03 (m, 2H), 3.26-3.22 (m, 2H), 3.12-3.07 (m, 1H), 1.16 (dd, 3H, J=6 Hz, 15 Hz).

3-Methyl-[(4'-Methoxy)-2-Phenyl]morpholine hydrochloride (4f, PAL 751)

The product was isolated as a white solid in 30% yield (97 mg); $^1$H NMR (CD$_3$OD, 300 MHz) δ 7.31 (d, 2H, J=6 Hz), 6.95 (d, 2H, J=6 Hz), 4.30 (d, 1H, J=9 Hz), 4.19-4.15 (m, 1H), 3.92-3.83 (m, 1H), 3.80 (s, 3H), 3.40-3.35 (m, 3H), 1.04 (d, 3H, J=9 Hz); ESI-MS, calculated for C$_{12}$H$_{17}$NO$_2$ (M+H)$^+$208.3; observed 207.8; Anal. Calculated for C$_{12}$H$_{18}$ClNO$_2$; C, 59.14; H, 7.44; N, 5.75. Found: C, 59.03; H, 7.40; N, 5.68.

3-Methyl-[(4'-Cyano)-2-Phenyl]morpholine (0.5 fumarate) (4 g, PAL 772)

The product was isolated as a white solid in 12% yield (56 mg); $^1$H NMR (CD$_3$OD, 300 MHz) δ 7.76 (d, 2H, J=9 Hz), 7.58 (d, 2H, J=6 Hz), 6.68 (s, 1H), 4.33 (d, 1H, J=9 Hz), 4.09 (d, 1H, J=3 Hz), 3.84-3.78 (m, 1H), 3.28-3.21 (m, 3H), 0.96 (d, 3H, J=6 Hz); ESI-MS, calculated for C$_{12}$H$_{14}$N$_2$O (M+H)$^+$203.3; observed 203.1; Anal. Calculated for C$_{14}$H$_{16}$N$_2$O$_3$; C, 64.60; H, 6.20; N, 10.76. Found: C, 64.65; H, 6.23; N, 10.85.

3-Methyl-[(4'-Cyano)-2-Phenyl]morpholine $^1$H NMR (CDCl$_3$ 300 MHz) δ 7.67 (d, 2H, J=9 Hz), 7.48 (d, 2H, J=9 Hz), 4.25 (d, 1H, J=9 Hz), 4.09-4.04 (m, 1H), 3.95-3.83 (m, 1H), 3.24-3.15 (m, 2H), 2.97-2.92 (m, 1H), 0.99 (d, 3H, J=6 Hz); $^{13}$C NMR (CDCl$_3$, 75 MHz) δ 139.0, 132.5, 128.6, 85.9, 68.4, 56.7, 46.8, 18.5.

3-Methyl-2-(3'-Tolyl)morpholine (0.5 fumarate) (4h, PAL 773)

The product was isolated as a white solid in 18% yield (31 mg); $^1$H NMR (CD$_3$OD, 300 MHz) δ 7.28-7.14 (m, 4H), 6.66 (s, 1H), 4.21 (d, 1H, J=9 Hz), 4.08 (d, 1H, J=3 Hz), 3.92-3.82 (m, 1H), 3.28-3.19 (m, 3H), 2.35 (s, 3H), 0.96 (d, 3H, J=6 Hz); ESI-MS, calculated for C$_{12}$H$_{17}$NO (M+H)$^+$ 192.3; observed 192.1; Anal. Calculated for C$_{14}$H$_{19}$NO$_3$; C, 67.45; H, 7.68; N, 5.62. Found: C, 67.17; H, 7.64; N, 5.57.

3-Methyl-2-(3'-Tolyl)morpholine $^1$H NMR (CDCl$_3$ 300 MHz) δ 7.25-7.21 (m, 2H), 7.16-7.10 (m, 2H), 4.14 (d, 1H, J=9 Hz), 4.07-4.02 (m, 1H), 3.92-3.89 (m, 1H), 3.21-3.00 (m, 3H), 2.35 (s, 3H), 0.99 (dd, 3H, J=9 Hz, 12 Hz); $^{13}$C NMR (CDCl$_3$, 75 MHz) δ 140.2, 139.0, 129.2, 128.5, 128.4, 125.1, 86.9, 68.6, 56.4, 46.9, 21.8, 18.8.

3-Methyl-[(3'-Hydroxy)-2-Phenyl]morpholine hydrochloride (4i, PAL 780)

The product was isolated as a white solid in 10% yield (45 mg); $^1$H NMR (CD$_3$OD, 300 MHz) δ 7.20 (t, 1H, J=3 Hz, 6 Hz), 6.85-6.79 (m, 3H), 4.29 (d, 1H, J=12 Hz), 4.19 (d, 1H, J=12 Hz), 3.98-3.85 (m, 1H), 3.41-3.33 (m, 3H), 1.07 (d, 3H, J=9 Hz); ESI-MS, calculated for C$_{11}$H$_{15}$NO$_2$ (M+H)$^+$194.2; observed 194.3; Anal. Calculated for C$_{11}$H$_{16}$ClNO$_2$; C, 57.52; H, 7.02; N, 6.10. Found: C, 57.67; H, 7.06; N, 6.01.

3-Methyl-[(3'-Cyano)-2-Phenyl]morpholine hydrochloride (4j, PAL 786)

The product was isolated as a white solid in 59% yield (397 mg); $^1$H NMR (CD$_3$OD, 300 MHz) δ 7.84 (d, 1H, J=3 Hz), 7.79-7.73 (m, 2H), 7.61 (t, 1H, J=6 Hz, 9 Hz), 4.50 (d, 1H, J=9 Hz), 4.21-4.19 (m, 1H), 4.03-3.93 (m, 1H), 3.46-3.41 (m, 3H), 1.08 (d, 3H, J=6 Hz); ESI-MS, calculated for C$_{12}$H$_{14}$N$_2$O (M+H)$^+$203.2; observed 203.5; Anal. Calculated (with 0.3 mol water) for C$_{12}$H$_{15}$ClN$_2$O; C, 59.04; H, 6.44; N, 11.48. Found: C, 59.19; H, 6.16; N, 11.29.

3-Methyl-[(3',4'-Dichloro)-2-Phenyl]morpholine hydrochloride (4k, PAL 788)

The product was isolated as a white solid in 52% yield (120 mg); $^1$H NMR (CD$_3$OD, 300 MHz) δ 7.64 (s, 1H), 7.58 (d, 1H, J=6 Hz), 7.37-7.30 (m, 1H), 4.42 (d, 1H, J=9 Hz), 4.23-4.17 (m, 1H), 4.01-3.92 (m, 1H), 3.43-3.37 (m, 3H), 1.09 (d, 3H, J=9 Hz); $^{13}$C NMR (free amine) (CDCl$_3$, 75 MHz) δ 140.5, 130.6, 129.8, 127.3, 85.2, 68.4, 56.6, 46.7, 18.4; ESI-MS, calculated for $C_{11}H_{13}Cl_2NO$ (M+H)$^+$247.2; observed 246.2; Anal. Calculated for $C_{11}H_{14}Cl_3NO$; C, 46.75; H, 4.99; N, 4.96; Cl, 37.63. Found: C, 46.92; H, 4.89; N, 5.02; Cl, 37.78.

3-Methyl-[(3'-Chloro-4'-Fluoro)-2-Phenyl]morpholine hydrochloride (4l, PAL 821)

The product was isolated as a white solid in 25% yield (169 mg); $^1$H NMR (CD$_3$OD, 300 MHz) δ 7.60 (dd, 1H, J=3 Hz, 6 Hz), 7.40-7.36 (m, 1H), 7.29 (t, 1H, J=9 Hz), 4.40 (d, 1H, J=9 Hz), 4.24-4.18 (m, 1H), 4.01-3.91 (m, 1H), 3.43-3.37 (m, 3H), 1.07 (d, 3H, J=6 Hz); $^{13}$C NMR (free amine) (CDCl$_3$, 75 MHz) δ 143.0, 140.0, 130.0, 127.0, 123.0, 81.4, 56.0, 49.8, 46.0, 34.8, 15.4; ESI-MS, calculated for $C_{11}H_{13}ClFNO$ (M+H)$^+$230.7; observed 230.3; Anal. Calculated for $C_{11}H_{14}Cl_2FNO$; C, 49.64; H, 5.30; N, 5.26; Cl, 26.64; F, 7.14. Found: C, 49.41; H, 5.30; N, 5.22; Cl, 26.84; F, 7.07.

3-Methyl-[(3'-Chloro-4'-Methyl)-2-Phenyl]morpholine hydrochloride (4m, PAL 822)

The product was isolated as a white solid in 25% yield (248 mg); $^1$H NMR (CD$_3$OD, 300 MHz) δ 7.44 (d, 1H, J=3 Hz), 7.33 (d, 1H, J=6 Hz), 7.24 (d, 1H, J=6 Hz), 4.36 (d, 1H, J=12 Hz), 4.24-4.17 (m, 1H), 4.02-3.90 (m, 1H), 3.42-3.36 (m, 3H), 2.37 (s, 3H), 1.07 (d, 3H, J=6 Hz); $^{13}$C NMR (free amine) (CDCl$_3$, 75 MHz) δ 131.0, 128.4, 127.9, 126.2, 85.9, 68.6, 56.5, 46.8, 20.1, 18.7; APCI-MS, calculated for $C_{12}H_{16}ClNO$ (M+H)$^+$226.7; observed 226.2; Anal. Calculated for $C_{12}H_{17}Cl_2NO$; C, 54.98; H, 6.54; N, 5.34; Cl, 27.04. Found: C, 55.16; H, 6.52; N, 5.41; Cl, 27.18.

3-Methyl-[(3'-Methoxy)-2-Phenyl]morpholine (0.5 fumarate) (4n, PAL 823)

The product was isolated as a white solid in 53% yield (218 mg); $^1$H NMR (CD$_3$OD, 300 MHz) δ 7.29 (t, 1H, J=6 Hz, 9 Hz), 6.95-6.90 (m, 3H), 6.68 (s, 1H), 4.23 (d, 1H, J=9 Hz), 4.13-4.05 (m, 1H), 3.92-3.82 (m, 1H), 3.80 (s, 3H), 3.26-3.19 (m, 3H), 0.97 (d, 3H, J=6 Hz); ESI-MS, calculated for $C_{12}H_{17}NO_2$ (M+H)$^+$208.3; observed 208.0; Anal. Calculated for $C_{14}H_{19}NO_4$; C, 63.38; H, 7.22; N, 5.28. Found: C, 63.35; H, 7.28; N, 5.25.

3-Methyl-[(3'-Methoxy)-2-Phenyl]morpholine $^1$H NMR (CDCl$_3$ 300 MHz) δ 7.27-7.22 (m, 2H), 6.93-6.82 (m, 2H), 4.01-3.91 (m, 2H), 3.81 (s, 3H), 3.70 (t, 1H, J=12 Hz), 3.15 (t, 1H, J=12 Hz), 2.96-2.83 (m, 2H), 0.83 (d, 3H, J=6 Hz); $^{13}$C NMR (CDCl$_3$, 75 MHz) δ 160.0, 141.8, 129.6, 120.4, 114.0, 113.3, 86.7, 68.6, 56.5, 55.6, 46.9, 18.7.

Example 3

Preparation of Additional Compounds

Additional compounds were prepared according to the following procedures. The procedure used to prepare various compounds is noted and the reagents and intermediates are represented in Schemes 1, 2, and 3, below.

General Procedure A.

To a stirring solution under N$_2$ of the commercially available amine (1.0 equiv.) in MeOH (dried over 4 Å molecular sieves, 0.20 M) was added an aryl epoxide (0.83 equiv.). The reaction mixture was heated to reflux for 4 h and then cooled to room temperature. The solution was allowed to stir at room temperature for 3 days and then concentrated under reduced pressure to yield an oily residue which was purified by flash chromatography on silica gel (10% to 20% MeOH/CH$_2$Cl$_2$ gradient) to remove the unreacted starting amine.

General Procedure B.

The secondary amine (1.0 equiv.) was dissolved in a 50%, 60%, or 90% aqueous HCl solution (0.37 M) and heated to 90° C. overnight under N$_2$. The reaction mixture was allowed to cool to room temperature and poured onto ice water. After chilling to 0° C., the solution was carefully basified to pH 12 with a 3 M aqueous NaOH solution. After warming to room temperature, ether was added and the biphasic mixture was partitioned in a separatory funnel. The aqueous portion was extracted twice with Et$_2$O and the combined organic extracts were washed with water and brine and dried over Na$_2$SO$_4$. Filtration and concentration under reduced pressure, followed by flash chromatography on silica gel (5% to 20% MeOH/CH$_2$Cl$_2$ gradient) afforded the cyclized product.

General Procedure C.

The secondary amine (1.0 equiv.) was dissolved in concentrated H$_2$SO$_4$ (0.4 M) and allowed to stand at room temperature overnight. The reaction mixture was then poured onto ice water. After chilling to 0° C., the solution was carefully basified to pH 12 with a 10 N aqueous NaOH solution. After warming to room temperature, ether was added and the biphasic mixture was partitioned in a separatory funnel. The aqueous portion was extracted twice with Et$_2$O and the combined organic extracts were washed with water and brine and dried over Na$_2$SO$_4$. Filtration and concentration under reduced pressure, followed by flash chromatography on silica gel (5% to 20% MeOH/CH$_2$Cl$_2$ gradient) afforded the cyclized product.

Scheme 1

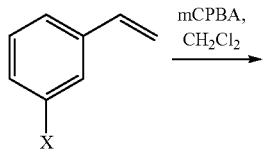

1a: X = H
1b: X = OMe
1c: X = Me
1d: X = Cl
1e: X = F
1f: X = CF$_3$

-continued

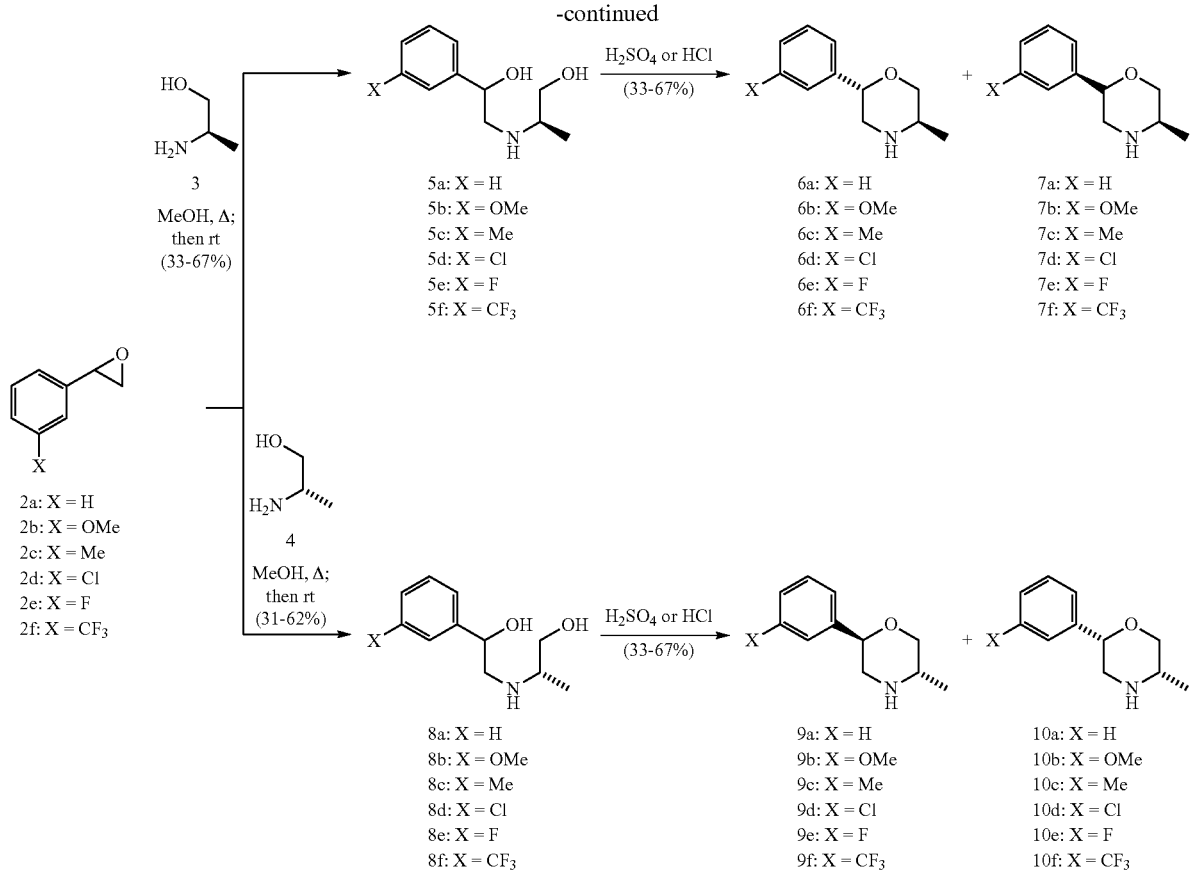

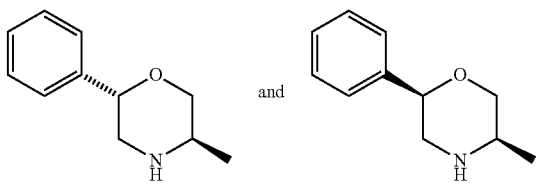

(2S,5R)-5-Methyl-2-phenyl-morpholine (6a) and
(2R,5R)-5-Methyl-2-phenyl-morpholine (7a)

General procedure A was followed using amine 3 (0.50 mL, 6.42 mmol) and epoxide 2a (0.61 mL, 5.33 mmol) in dry MeOH (30 mL) under $N_2$ to afford 344 mg (33% yield) of amine 5a as a clear oil. General procedure B was then followed using amine 5a (344 mg, 1.76 mmol) in 60% aqueous HCl (4.8 mL) under $N_2$ to afford a mixture of separable isomers in a 1.9:1 (anti:syn) ratio. Anti isomer 6a: 138 mg (44% yield) isolated as a clear sticky oil. $[\alpha]^{20}_D+$ 67.3 (c 0.0011, MeOH); $^1$H NMR (CDCl$_3$, 300 MHz) δ 7.36-7.27 (m, 5H), 4.42 (dd, J=9.0, 3.0 Hz, 1H), 3.96 (dd, J=12.0, 3.0 Hz, 1H), 3.32 (t, J=12.0, 9.0 Hz, 1H), 3.08 (dd, J=12.0, 3.0 Hz, 1H), 3.03-2.94 (m, 1H), 2.84 (t, J=24.0, 12.0 Hz, 1H), 2.01 (br. s, 1H), 1.02 (d, J=6.0 Hz, 3H); $^{13}$C NMR (CDCl$_3$, 75 MHz) ppm 140.6, 128.7, 128.1, 126.5, 79.1, 74.6, 53.7, 50.2, 17.9; MS (ESI) calcd for (M+1)$^+$178.2, found 178.4. The hydrochloride salt had mp 214-215° C.; Anal. (C$_{11}$H$_{16}$ClNO) C, H, N. Syn isomer 7a: 72 mg (23% yield) isolated as a clear sticky oil contaminated with unreacted starting material. The hydrochloride salt had mp 136-137° C.; $[\alpha]^{20}_D$−34.1 (c 0.00205, MeOH); $^1$H NMR (CD$_3$OD, 300 MHz) δ 7.24-7.11 (m, 5H), 4.61-4.56 (m, 1H), 3.92 (dd, J=12.0, 3.0 Hz, 1H), 3.78-3.74 (m, 1H), 3.48-3.42 (m, 1H), 3.07-3.06 (m, 2H), 1.36 (d, J=6.0 Hz, 3H); $^{13}$C NMR (CD$_3$OD, 75 MHz) ppm 139.2, 130.2, 127.6, 77.3, 69.8, 48.8, 44.4, 13.9; MS (ESI) calcd for (M+1)$^+$178.2, found 178.3 (free base); Anal. (C$_{11}$H$_{16}$ClNO) C, H, N.

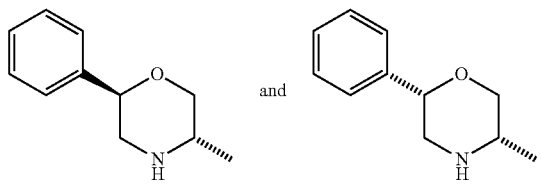

(2R,5S)-5-Methyl-2-phenyl-morpholine (9a) and
(2S,5S)-5-Methyl-2-phenyl-morpholine (10a)

General procedure A was followed using amine 4 (0.50 mL, 6.43 mmol) and epoxide 2a (0.61 mL, 5.34 mmol) in dry MeOH (32 mL) under $N_2$ to afford 538 mg (52% yield) of amine 8a as a pale yellow oil. General procedure B was then followed using amine 8a (350 mg, 1.79 mmol) in 60% aqueous HCl (4.8 mL) under $N_2$ to afford a mixture of separable isomers in a 2.2:1 (anti:syn) ratio. Anti isomer 9a: 128 mg (40% yield) isolated as a clear sticky oil. $[\alpha]^{20}_D$−31.0 (c 0.0029, MeOH); $^1$H NMR (CDCl$_3$, 300 MHz) δ

7.35-7.27 (m, 5H), 4.43 (dd, J=12.0, 3.0 Hz, 1H), 3.97 (dd, J=12.0, 3.0 Hz, 1H), 3.32 (t, J=21.0, 12.0 Hz, 1H), 3.09 (dd, J=15.0, 3.0 Hz, 1H), 3.05-2.95 (m, 1H), 2.86 (t, J=24.0, 12.0 Hz, 1H), 1.84 (br. s, 1H), 1.03 (d, J=6.0 Hz, 3H); $^{13}$C NMR (CDCl$_3$, 75 MHz) ppm 140.7, 128.7, 128.1, 126.5, 79.2, 74.7, 53.7, 50.2, 17.9; MS (ESI) calcd for (M+1)$^+$178.2, found 178.5. The hydrochloride salt had mp 214-215° C.; Anal. (C$_{11}$H$_{16}$ClNO) C, H, N. Syn isomer 10a: 57 mg (18% yield) isolated as a clear sticky oil contaminated with unreacted starting material. The fumarate had mp 164-165° C.; [α]$^{20}$$_D$+12.5 (c 0.0016, MeOH); $^1$H NMR (CD$_3$OD, 300 MHz) δ 7.44-7.34 (m, 5H), 6.69 (s, 2H), 4.74 (t, J=15.0, 9.0 Hz, 1H), 4.12-3.94 (m, 2H), 3.65-3.57 (m, 1H), 3.32-3.26 (hidden m, 2H), 1.55 (d, J=9.0 Hz, 3H); $^{13}$C NMR (CD$_3$OD, 75 MHz) ppm 171.4, 139.1, 136.2, 129.8, 127.2, 77.3, 69.7, 48.4, 44.3, 13.8; MS (ESI) calcd for (M+1)$^+$178.2, found 178.1 (free base); Anal. (C$_{15}$H$_{19}$NO$_5$.02H$_2$O) C, H, N.

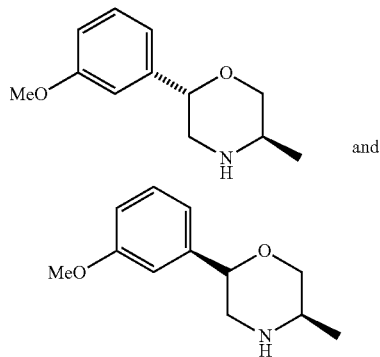

(2S,5R)-2-(3-Methoxy-phenyl)-5-methyl-morpholine (6b) and (2R,5R)-2-(3-Methoxy-phenyl)-5-methyl-morpholine (7b)

General procedure A was followed using amine 3 (0.66 mL, 8.49 mmol) and epoxide 2b (1.16 g, 7.72 mmol) in dry MeOH (26 mL) under N$_2$ to afford 811 mg (47% yield) of amine 5b as a pale yellow oil. General procedure B was then followed using amine 5b (811 mg, 3.60 mmol) in 90% aqueous HCl (9.7 mL) under N$_2$ to afford a mixture of separable isomers in a 2:1 (anti:syn) ratio. Anti isomer 6b: 162 mg (22% yield) isolated as a pale yellow oil. [α]$^{20}$$_D$+41.1 (c 0.0009, MeOH); $^1$H NMR (CDCl$_3$, 300 MHz) δ 7.25 (t, J=15.0, 6.0 Hz, 1H), 6.93-6.91 (m, 2H), 6.83 (br. d, J=9.0 Hz, 1H), 4.41 (dd, J=9.0, 3.0 Hz, 1H), 3.96 (dd, J=9.0, 3.0 Hz, 1H), 3.82 (s, 3H), 3.29 (t, J=12.0, 9.0 Hz, 1H), 3.08 (dd, J=12.0, 3.0 Hz, 1H), 3.04-2.95 (m, 1H), 2.82 (br, t, J=12.0, 6.0 Hz, 1H), 1.99 (br. s, 1H), 1.03 (d, J=9.0 Hz, 3H); $^{13}$C NMR (CDCl$_3$, 75 MHz) ppm 159.8, 141.8, 129.3, 118.4, 113.3, 111.6, 78.6, 74.2, 55.2, 53.2, 49.8, 17.4; MS (ESI) calcd for (M+1)$^+$208.3, found 208.2. The hydrochloride salt had mp 168-169° C.; Anal. (C$_{12}$H$_{18}$ClNO$_2$) C, H, N. Syn isomer 7b: 84 mg (11% yield) isolated as a pale yellow oil contaminated with unreacted starting material. The fumarate had mp 172-174° C.; [α]$^{20}$$_D$-14.2 (c 0.0033, MeOH); $^1$H NMR (CD$_3$OD, 300 MHz) δ 7.30 (t, J=15.0, 9.0 Hz, 1H), 6.99-6.96 (m, 2H), 6.90 (d, J=9.0 Hz, 1H), 6.70 (s, 2H), 4.75 (dd, J=9.0, 3.0 Hz, 1H), 4.09 (dd, J=12.0, 3.0 Hz, 1H), 3.95 (d, J=12.0 Hz, 1H), 3.80 (s, 3H), 3.66-3.58 (m, 1H), 3.31-3.24 (hidden m, 2H), 1.54 (d, J=9.0 Hz, 3H); $^{13}$C NMR (CD$_3$OD, 75 MHz) ppm 171.4, 161.5, 140.5, 136.2, 130.9, 119.2, 115.1, 112.9, 76.9, 69.5, 55.8, 48.2, 44.0, 13.6; MS (ESI) calcd for (M+1)$^+$208.3, found 207.9 (free base); Anal. (C$_{16}$H$_{21}$NO$_6$.0.2H$_2$O) C, H, N.

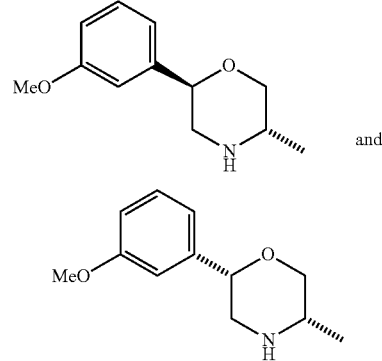

(2R,5S)-2-(3-Methoxy-phenyl)-5-methyl-morpholine (9b) and (2S,5S)-2-(3-Methoxy-phenyl)-5-methyl-morpholine (10b)

General procedure A was followed using amine 4 (0.66 mL, 8.49 mmol) and epoxide 2b (1.16 g, 7.72 mmol) in dry MeOH (26 mL) under N$_2$ to afford 1.07 g (62% yield) of amine 8b as a pale yellow oil. General procedure B was then followed using amine 8b (1.07 g, 4.75 mmol) in 90% aqueous HCl (13 mL) under N$_2$ to afford a mixture of separable isomers in a 2:1 (anti:syn) ratio. Anti isomer 9b: 235 mg (24% yield) isolated as a pale yellow oil. [α]$^{20}$$_D$-95.8 (c 0.0019, MeOH); $^1$H NMR (CDCl$_3$, 300 MHz) δ 7.24 (t, J=18.0, 9.0 Hz, 1H), 6.90 (br. s, 2H), 6.82 (br. d, J=9.0 Hz, 1H), 4.39 (d, J=9.0 Hz, 1H), 3.96 (dd, J=12.0, 3.0 Hz, 1H), 3.79 (s, 3H), 3.30 (t, J=24.0, 12.0 Hz, 1H), 3.05 (d, J=15.0 Hz, 1H), 3.01-2.94 (m, 1H), 2.83 (t, J=24.0, 12.0 Hz, 1H), 2.15 (br. s, 1H), 1.01 (d, J=6.0 Hz, 3H); $^{13}$C NMR (CDCl$_3$, 75 MHz) ppm 159.7, 141.9, 129.3, 118.4, 113.3, 111.6, 78.6, 74.2, 55.2, 53.2, 49.8, 17.4; MS (ESI) calcd for (M+1)$^+$ 208.3, found 208.2. The hydrochloride salt had mp 169-171° C.; Anal. (C$_{12}$H$_{18}$ClNO$_2$.0.2H$_2$O) C, H, N. Syn isomer 10b: 118 mg (12% yield) isolated as a pale yellow oil contaminated with unreacted starting material. The fumarate had mp 177-178° C.; [α]$^{20}$$_D$+15.9 (c 0.0027, MeOH); $^1$H NMR (CD$_3$OD, 300 MHz) δ 7.30 (t, J=15.0, 9.0 Hz, 1H), 6.99-6.97 (m, 2H), 6.90 (d, J=12.0 Hz, 1H), 6.70 (s, 2H), 4.74 (dd, J=9.0, 3.0 Hz, 1H), 4.09 (dd, J=12.0, 3.0 Hz, 1H), 3.95 (d, J=12.0 Hz, 1H), 3.80 (s, 3H), 3.65-3.58 (m, 1H), 3.31-3.24 (hidden m, 2H), 1.55 (d, J=9.0 Hz, 3H); $^{13}$C NMR (CD$_3$OD, 75 MHz) ppm 171.5, 161.5, 140.5, 136.2, 130.9, 119.2, 115.1, 112.9, 76.9, 69.5, 55.8, 48.2, 44.1, 13.6; MS (ESI) calcd for (M+1)$^+$208.3, found 207.8 (free base); Anal. (C$_{16}$H$_{21}$NO$_6$.0.25H$_2$O) C, H, N.

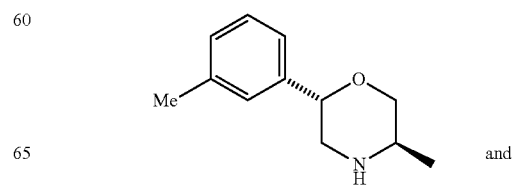

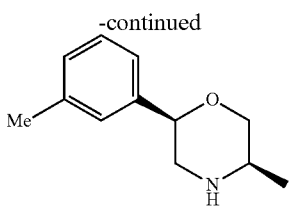

(2S,5R)-5-Methyl-2-m-tolyl-morpholine (6c) and (2R,5R)-5-Methyl-2-m-tolyl-morpholine (7c)

General procedure A was followed using amine 3 (0.56 mL, 7.17 mmol) and epoxide 2c (875 mg, 6.52 mmol) in dry MeOH (22 mL) under $N_2$ to afford 625 mg (46% yield) of amine 5c as a thick yellow oil. General procedure B was then followed using amine 5c (575 mg, 2.75 mmol) in 90% aqueous HCl (7.4 mL) under $N_2$ to afford a mixture of separable isomers in a 1.4:1 (anti:syn) ratio. Anti isomer 6c: 166 mg (32% yield) isolated as a clear oil. $[\alpha]^{20}_D$+33.3 (c 0.00135, MeOH); $^1$H NMR (CDCl$_3$, 300 MHz) δ 7.22-7.07 (m, 4H), 4.39 (dd, J=9.0, 3.0 Hz, 1H), 3.96 (dd, J=9.0, 3.0 Hz, 1H), 3.31 (t, J=21.0, 9.0 Hz, 1H), 3.06 (dd, J=12.0, 3.0 Hz, 1H), 3.02-2.94 (m, 1H), 2.85 (t, J=24.0, 12.0 Hz, 1H), 2.34 (s, 3H), 1.96 (br. s, 1H), 1.02 (d, J=6.0 Hz, 3H); $^{13}$C NMR (CDCl$_3$, 75 MHz) ppm 140.2, 138.0, 128.4, 128.2, 126.7, 123.2, 78.8, 74.3, 53.3, 49.9, 21.4, 17.5; MS (ESI) calcd for (M+1)$^+$192.3, found 192.5. The hydrochloride salt had mp 194-195° C.; Anal. (C$_{12}$H$_{18}$ClNO) C, H, N. Syn isomer 7c: 117 mg (22% yield) isolated as a clear oil contaminated with unreacted starting material. The fumarate had mp 175-176° C.; $[\alpha]^{20}_D$–19.2 (c 0.0012, MeOH); $^1$H NMR (CD$_3$OD, 300 MHz) δ 7.30-7.15 (m, 4H), 6.70 (s, 2H), 4.72 (br. t, J=15.0, 6.0 Hz, 1H), 4.08 (dd, J=12.0, 3.0 Hz, 1H), 3.96 (br. d, J=15.0 Hz, 1H), 3.65-3.58 (m, 1H), 3.27-3.24 (m, 2H), 2.35 (s, 3H), 1.55 (d, J=6.0 Hz, 3H); $^{13}$C NMR (CD$_3$OD, 75 MHz) ppm 171.5, 139.7, 138.9, 136.2, 130.4, 129.7, 127.7, 124.2, 77.1, 69.5, 48.2, 44.1, 21.4, 13.6; MS (ESI) calcd for (M+1)$^+$192.3, found 192.3 (free base); Anal. (C$_{16}$H$_{21}$NO$_5$.0.25H$_2$O) C, H, N.

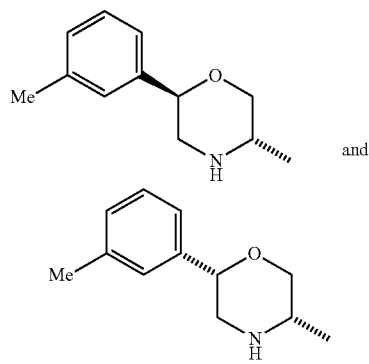

(2R,5S)-5-Methyl-2-m-tolyl-morpholine (9c) and (2S,5S)-5-Methyl-2-m-tolyl-morpholine (10c)

General procedure A was followed using amine 4 (0.56 mL, 7.17 mmol) and epoxide 2c (875 mg, 6.52 mmol) in dry MeOH (22 mL) under $N_2$ to afford 416 mg (31% yield) of amine 8c as a yellow oil. General procedure B was then followed using amine 8c (416 mg, 1.99 mmol) in 90% aqueous HCl (5.4 mL) under $N_2$ to afford a mixture of separable isomers in a 1.9:1 (anti:syn) ratio. Anti isomer 9c: 143 mg (38% yield) isolated as a clear oil. $[\alpha]^{20}_D$–11.7 (c 0.0095, MeOH); $^1$H NMR (CDCl$_3$, 300 MHz) δ 7.22-7.10 (m, 4H), 4.38 (dd, J=12.0, 3.0 Hz, 1H), 3.96 (dd, J=12.0, 3.0 Hz, 1H), 3.31 (t, J=21.0, 12.0 Hz, 1H), 3.07 (dd, J=12.0, 3.0 Hz, 1H), 3.03-2.96 (m, 1H), 2.86 (br. t, J=21.0, 9.0 Hz, 1H), 2.34 (s, 3H), 1.88 (br. s, 1H), 1.02 (d, J=6.0 Hz, 3H); $^{13}$C NMR (CDCl$_3$, 75 MHz) ppm 140.2, 138.0, 128.4, 128.2, 126.7, 123.2, 78.8, 74.3, 53.3, 49.9, 21.4, 17.5; MS (ESI) calcd for (M+1)$^+$192.3, found 192.2. The hydrochloride salt had mp 194-195° C.; Anal. (C$_{12}$H$_{18}$ClNO) C, H, N. Syn isomer 10c: 76 mg (20% yield) isolated as a clear oil contaminated with unreacted starting material. The fumarate had mp 168-170° C.; $[\alpha]^{20}_D$+14.5 (c 0.0020, MeOH); $^1$H NMR (CD$_3$OD, 300 MHz) δ 7.30-7.15 (m, 4H), 6.70 (s, 2H), 4.72 (dd, J=9.0, 6.0 Hz, 1H), 4.10 (dd, J=12.0, 3.0 Hz, 1H), 3.94 (d, J=12.0 Hz, 1H), 3.66-3.58 (m, 1H), 3.27-3.24 (m, 2H), 2.35 (s, 3H), 1.55 (d, J=6.0 Hz, 3H); $^{13}$C NMR (CD$_3$OD, 75 MHz) ppm 171.5, 139.7, 139.0, 136.2, 130.4, 129.7, 127.7, 124.2, 77.1, 69.5, 48.2, 44.0, 21.4, 13.6; MS (ESI) calcd for (M+1)$^+$192.3, found 192.1 (free base); Anal. (C$_{16}$H$_{21}$NO$_5$) C, H, N.

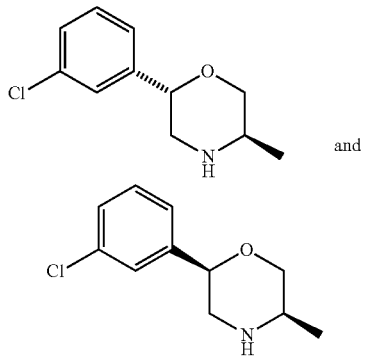

(2S,5R)-2-(3-Chloro-phenyl)-5-methyl-morpholine (6d) and (2R,5R)-2-(3-Chloro-phenyl)-5-methyl-morpholine (7d)

General procedure A was followed using amine 3 (0.50 mL, 6.42 mmol) and epoxide 2d (824 mg, 5.33 mmol) in dry MeOH (21 mL) under $N_2$ to afford 649 mg (53% yield) of amine 5d as a thick clear oil. General procedure C was then followed using amine 5d (649 mg, 2.83 mmol) in concentrated $H_2SO_4$ (7 mL) to afford a mixture of separable isomers in a 10.3:1 (anti:syn) ratio. Anti isomer 6d: 261 mg (44% yield) as a clear sticky oil. $[\alpha]^{20}_D$+42.1 (c 0.0024, MeOH); $^1$H NMR (CDCl$_3$, 300 MHz) δ 7.37 (s, 1H), 7.29-7.20 (m, 3H), 4.39 (dd, J=9.0, 3.0 Hz, 1H), 3.96 (dd, J=12.0, 3.0 Hz, 1H), 3.30 (t, J=21.0, 9.0 Hz, 1H), 3.06 (dd, J=12.0, 3.0 Hz, 1H), 3.01-2.92 (m, 1H), 2.79 (t, J=21.0, 9.0 Hz, 1H), 2.01 (br. s, 1H), 1.01 (d, J=6.0 Hz, 3H); $^{13}$C NMR (CDCl$_3$, 75 MHz) ppm 142.7, 134.6, 130.0, 128.1, 126.6, 124.6, 78.3, 74.5, 53.6, 50.1, 17.8; MS (ESI) calcd for (M+1)$^+$212.7, found 212.1. The hydrochloride salt had mp 170-171° C.; Anal. (C$_{11}$H$_{15}$Cl$_2$NO) C, H, N. Syn isomer 7d: 36 mg (6% yield) as a clear sticky oil. $[\alpha]^{20}_D$–6.7 (c 0.0015, MeOH); $^1$H NMR (CDCl$_3$, 300 MHz) δ 7.42 (s, 1H), 7.32-7.23 (m, 3H), 4.52 (dd, J=6.0, 3.0 Hz, 1H), 3.86 (dd, J=12.0, 3.0 Hz, 1H), 3.70 (dd, J=9.0, 3.0 Hz, 1H), 3.18-3.10 (m, 2H), 2.97 (dd, J=12.0, 3.0 Hz, 1H), 2.35 (br. s, 1H), 1.31 (d, J=6.0 Hz, 3H);

$^{13}$C NMR (CDCl$_3$, 75 MHz) ppm 142.6, 134.8, 130.1, 128.1, 126.8, 124.7, 77.5, 71.4, 47.7, 46.8, 17.0; MS (ESI) calcd for (M+1)$^+$212.7, found 212.1. The fumarate had mp 169-171° C.; Anal. (C$_{15}$H$_{18}$ClNO$_5$) C, H, N.

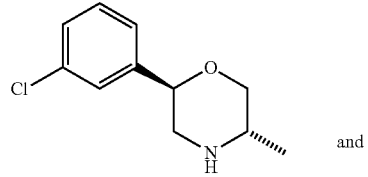

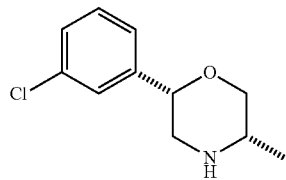

(2R,5S)-2-(3-Chloro-phenyl)-5-methyl-morpholine (9d) and (2S,5S)-2-(3-Chloro-phenyl)-5-methyl-morpholine (10d)

General procedure A was followed using amine 4 (0.50 mL, 6.43 mmol) and epoxide 2d (826 mg, 5.34 mmol) in dry MeOH (21 mL) under N$_2$ to afford 598 mg (49% yield) of amine 8d as a pale yellow oil. General procedure C was then followed using amine 8d (598 mg, 2.60 mmol) in concentrated H$_2$SO$_4$ (6.5 mL) to afford a mixture of separable isomers in a 17.8:1 (anti:syn) ratio. Anti isomer 9d: 285 mg (52% yield) as a clear sticky oil. [α]$^{20}_D$–40.4 (c 0.0024, MeOH); $^1$H NMR (CDCl$_3$, 300 MHz) δ 7.37 (s, 1H), 7.28-7.19 (m, 3H), 4.40 (dd, J=12.0, 6.0 Hz, 1H), 3.96 (dd, J=9.0, 3.0 Hz, 1H), 3.30 (t, J=21.0, 12.0 Hz, 1H), 3.06 (dd, J=12.0, 3.0 Hz, 1H), 3.01-2.93 (m, 1H), 2.79 (t, J=24.0, 12.0 Hz, 1H), 2.06 (br. s, 1H), 1.02 (d, J=6.0 Hz, 3H); $^{13}$C NMR (CDCl$_3$, 75 MHz) ppm 142.6, 134.6, 130.0, 128.2, 126.6, 124.6, 78.2, 74.5, 53.5, 50.2, 17.8; MS (ESI) calcd for (M+1)$^+$212.7, found 212.1. The hydrochloride salt had mp 170-171° C.; Anal. (C$_{11}$H$_{15}$Cl$_2$NO) C, H, N. Syn isomer 10d: 42 mg (7.6% yield) as a clear sticky oil. [α]$^{20}_D$+30.9 (c 0.0022, MeOH); $^1$H NMR (CDCl$_3$, 300 MHz) δ 7.37 (s, 1H), 7.32-7.23 (m, 3H), 4.53 (dd, J=9.0, 3.0 Hz, 1H), 3.87 (dd, J=9.0, 3.0 Hz, 1H), 3.70 (dd, J=12.0, 3.0 Hz, 1H), 3.19-3.10 (m, 2H), 2.97 (dd, J=12.0, 3.0 Hz, 1H), 2.38 (br. s, 1H), 1.31 (d, J=6.0 Hz, 3H); $^{13}$C NMR (CDCl$_3$, 75 MHz) ppm 142.7, 134.8, 130.1, 128.1, 126.8, 124.8, 77.0, 71.4, 47.7, 46.9, 17.0; MS (ESI) calcd for (M+1)$^+$212.7, found 212.1. The fumarate had mp 159-160° C.; Anal. (C$_{15}$H$_{18}$ClNO$_5$.0.7H$_2$O) C, H, N.

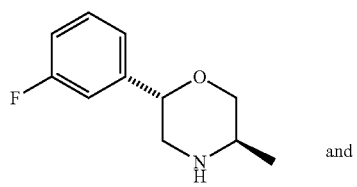

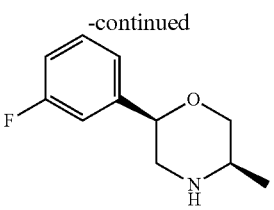

(2S,5R)-2-(3-Fluoro-phenyl)-5-methyl-morpholine (6e) and (2R,5R)-2-(3-Fluoro-phenyl)-5-methyl-morpholine (7e)

General procedure A was followed using amine 3 (0.96 mL, 12.3 mmol) and epoxide 2e (1.55 g, 11.2 mmol) in dry MeOH (37 mL) under N$_2$ to afford 1.59 g (67% yield) of amine 5e as a pale yellow oil. General procedure C was then followed using amine 5e (1.49 g, 6.99 mmol) in concentrated H$_2$SO$_4$ (17 mL) to afford a mixture of separable isomers in a 4.2:1 (anti:syn) ratio. Anti isomer 6e: 553 mg (41% yield) as a pale yellow oil. [α]$^{20}_D$+30 (c 0.0006, MeOH); $^1$H NMR (CDCl$_3$, 300 MHz) δ 7.32-7.25 (m, 1H), 7.11-7.07 (m, 2H), 6.95 (br. t, J=21.0, 12.0 Hz, 1H), 4.41 (dd, J=12.0, 3.0 Hz, 1H), 3.95 (dd, J=9.0, 3.0 Hz, 1H), 3.29 (t, J=24.0, 12.0 Hz, 1H), 3.06 (dd, J=12.0, 3.0 Hz, 1H), 3.02-2.91 (m, 1H), 2.79 (br. t, J=21.0, 9.0 Hz, 1H), 1.74 (br. s, 1H), 1.00 (d, J=6.0 Hz, 3H); $^{13}$C NMR (CDCl$_3$, 75 MHz) ppm 164.5, 161.2, 143.0 (d, J=6.75 Hz), 129.7 (d, J=7.5 Hz), 121.5 (d, J=2.25 Hz), 114.3 (d, J=21.0 Hz), 113.0 (d, J=21.8 Hz), 78.0, 74.2, 53.3, 49.8, 17.4; MS (ESI) calcd for (M+1)$^+$196.2, found 196.2. The hydrochloride salt had mp 141-143° C.; Anal. (C$_{11}$H$_{15}$ClFNO) C, H, N. Syn isomer 7e: 132 mg (9.7% yield) as a pale yellow oil. [α]$^{20}_D$–39.4 (c 0.0034, MeOH); $^1$H NMR (CDCl$_3$, 300 MHz) δ 7.35-7.28 (m, 1H), 7.16-7.12 (m, 2H), 6.98 (br. t, J=21.0, 9.0 Hz, 1H), 4.54 (dd, J=9.0, 3.0 Hz, 1H), 3.86 (dd, J=12.0, 3.0 Hz, 1H), 3.70 (dd, J=12.0, 3.0 Hz, 1H), 3.20-3.07 (m, 2H), 2.97 (dd, J=12.0, 3.0 Hz, 1H), 1.97 (br. s, 1H), 1.30 (d, J=6.0 Hz, 3H); $^{13}$C NMR (CDCl$_3$, 75 MHz) ppm 164.6, 161.3, 142.8, 129.8 (d, J=8.25 Hz), 121.7 (d, J=3.0 Hz), 114.3 (d, J=21.0 Hz), 113.2 (d, J=22.5 Hz), 77.1, 71.0, 47.3, 46.4, 16.6; MS (ESI) calcd for (M+1)$^+$196.2, found 196.2. The fumarate had mp 165-167° C.; Anal. (C$_{15}$H$_{18}$FNO$_5$) C, H, N.

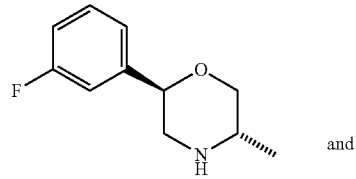

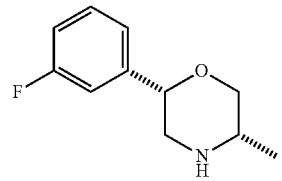

(2R,5S)-2-(3-Fluoro-phenyl)-5-methyl-morpholine (9e) and (2S,5S)-2-(3-Fluoro-phenyl)-5-methyl-morpholine (10e)

General procedure A was followed using amine 4 (0.96 mL, 12.3 mmol) and epoxide 2e (1.55 g, 11.2 mmol) in dry MeOH (37 mL) under N₂ to afford 1.33 mg (56% yield) of amine 8e as a pale yellow oil. General procedure C was then followed using amine 8e (1.33 g, 6.24 mmol) in concentrated H₂SO₄ (15.6 mL) to afford a mixture of separable isomers in a 5.7:1 (anti:syn) ratio. Anti isomer 9e: 658 mg (54% yield) as a pale yellow oil. [α]²⁰_D –48.6 (c 0.0022, MeOH); ¹H NMR (CDCl₃, 300 MHz) δ 7.32-7.27 (m, 1H), 7.11-7.07 (m, 2H), 6.96 (br. t, J=12.0, 9.0 Hz, 1H), 4.40 (dd, J=12.0, 3.0 Hz, 1H), 3.96 (dd, J=12.0, 3.0 Hz, 1H), 3.30 (t, J=21.0, 9.0 Hz, 1H), 3.07 (dd, J=12.0, 3.0 Hz, 1H), 3.02-2.92 (m, 1H), 2.78 (br. t, J=21.0, 9.0 Hz, 1H), 1.89 (br. s, 1H), 1.01 (d, J=6.0 Hz, 3H); ¹³C NMR (CDCl₃, 75 MHz) ppm 164.5, 161.2, 142.9 (d, J=6.75 Hz), 129.7 (d, J=8.25 Hz), 121.5 (d, J=3.0 Hz), 114.4 (d, J=21.0 Hz), 112.9 (d, J=21.8 Hz), 77.9, 74.2, 53.3, 49.8, 17.4; MS (ESI) calcd for (M+1)⁺196.2, found 196.2. The hydrochloride salt had mp 143-144° C.; Anal. (C₁₁H₁₅ClFNO) C, H, N. Syn isomer 10e: 115 mg (9.4% yield) as a pale yellow oil. [α]²⁰_D +34.2 (c 0.0024, MeOH); ¹H NMR (CDCl₃, 300 MHz) δ 7.35-7.28 (m, 1H), 7.16-7.12 (m, 2H), 6.98 (br. t, J=21.0, 9.0 Hz, 1H), 4.55 (dd, J=9.0, 3.0 Hz, 1H), 3.86 (dd, J=12.0, 3.0 Hz, 1H), 3.70 (dd, J=9.0, 3.0 Hz, 1H), 3.20-3.06 (m, 2H), 2.97 (dd, J=15.0, 6.0 Hz, 1H), 1.89 (br. s, 1H), 1.30 (d, J=9.0 Hz, 3H); ¹³C NMR (CDCl₃, 75 MHz) ppm 164.6, 161.4, 142.8 (d, J=6.75 Hz), 129.8 (d, J=8.25 Hz), 121.7 (d, J=2.25 Hz), 114.3 (d, J=21.0 Hz), 113.3 (d, J=21.8 Hz), 77.1, 71.0, 47.3, 46.5, 16.6; MS (ESI) calcd for (M+1)⁺196.2, found 196.2. The fumarate had mp 163-164° C.; Anal. (C₁₅H₁₈FNO₅) C, H, N.

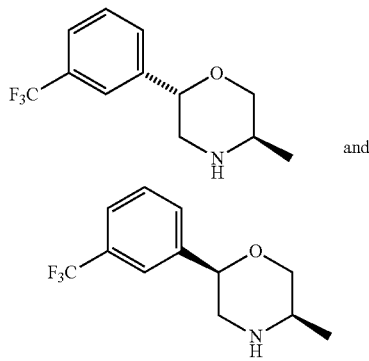

(2S,5R)-5-Methyl-2-(3-trifluoromethyl-phenyl)-morpholine (6f) and (2R,5R)-5-Methyl-2-(3-trifluoromethyl-phenyl)-morpholine (7f)

General procedure A was followed using amine 3 (0.38 mL, 4.91 mmol) and epoxide 2f (839 mg, 4.46 mmol) in dry MeOH (15 mL) under N₂ to afford 695 mg (59% yield) of amine 5f as a pale yellow oil. General procedure C was then followed using amine 5f (645 mg, 2.45 mmol) in concentrated H₂SO₄ (6.1 mL) to afford a mixture of separable isomers in a 4:1 (anti:syn) ratio. Anti isomer 6f: 293 mg (49% yield) as an off-white solid. [α]²⁰_D +37 (c 0.0070, MeOH); ¹H NMR (CDCl₃, 300 MHz) δ 7.64 (br. s, 1H), 7.50-7.41 (m, 3H), 4.46 (dd, J=12.0, 3.0 Hz, 1H), 3.97 (dd, J=9.0, 3.0 Hz, 1H), 3.31 (t, J=21.0, 12.0 Hz, 1H), 3.10 (dd, J=12.0, 3.0 Hz, 1H), 3.02-2.93 (m, 1H), 2.80 (br. t, J=21.0, 9.0 Hz, 1H), 1.76 (br. s, 1H), 1.02 (d, J=6.0 Hz, 3H); ¹³C NMR (CDCl₃, 75 MHz) ppm 141.4, 129.3, 128.7, 124.4, 122.8, 77.9, 74.2, 53.4, 49.8, 17.4; MS (ESI) calcd for (M+1)⁺246.2, found 246.4. The hydrochloride salt had mp 184-186° C.; Anal. (C₁₂H₁₅ClF₃NO) C, H, N. Syn isomer 7f: 68 mg (11% yield) as a pale yellow oil. [α]²⁰_D –32.4 (c 0.00145, MeOH); ¹H NMR (CDCl₃, 300 MHz) δ 7.68 (s, 1H), 7.59-7.47 (m, 3H), 4.59 (dd, J=9.0, 3.0 Hz, 1H), 3.88 (dd, J=9.0, 3.0 Hz, 1H), 3.72 (dd, J=12.0, 3.0 Hz, 1H), 3.20-3.06 (m, 2H), 2.98 (dd, J=12.0, 3.0 Hz, 1H), 2.25 (br. s, 1H), 1.31 (d, J=9.0 Hz, 3H); ¹³C NMR (CDCl₃, 75 MHz) ppm 141.3, 129.6, 128.8, 124.3 (d, J=3.75 Hz), 123.1 (d, J=3.75 Hz), 77.3, 71.1, 47.3, 46.6, 16.7; MS (ESI) calcd for (M+1)⁺246.2, found 246.3. The fumarate had mp 179-180° C.; Anal. (C₁₆H₁₈F₃NO₅·0.25H₂O) C, H, N.

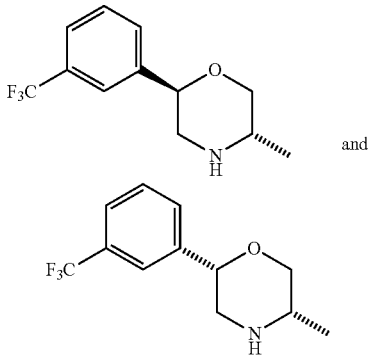

(2R,5S)-5-Methyl-2-(3-trifluoromethyl-phenyl)-morpholine (9f) and (2S,5S)-5-Methyl-2-(3-trifluoromethyl-phenyl)-morpholine (10f)

General procedure A was followed using amine 4 (0.40 mL, 5.09 mmol) and epoxide 2f (871 mg, 4.63 mmol) in dry MeOH (15.4 mL) under N₂ to afford 658 mg (54% yield) of amine 8f as a pale yellow oil. General procedure C was then followed using amine 8f (658 mg, 2.50 mmol) in concentrated H₂SO₄ (6.3 mL) to afford a mixture of separable isomers in a 4.2:1 (anti:syn) ratio. Anti isomer 9f: 300 mg (49% yield) as a pale yellow solid. [α]²⁰_D –35.2 (c 0.0096, MeOH); ¹H NMR (CDCl₃, 500 MHz) δ 7.64 (s, 1H), 7.53 (t, J=15.5, 7.5 Hz, 2H), 7.44 (t, J=15.5, 8.0 Hz, 1H), 4.47 (dd, J=10.0, 2.0 Hz, 1H), 3.98 (dd, J=11.0, 3.0 Hz, 1H), 3.32 (t, J=26.0, 10.5 Hz, 1H), 3.10 (dd, J=12.5, 2.5 Hz, 1H), 3.02-2.96 (m, 1H), 2.81 (br. t, J=23.0, 10.5 Hz, 1H), 1.76 (br. s, 1H), 1.02 (d, J=7.0 Hz, 3H); ¹³C NMR (CDCl₃, 125 MHz) ppm 141.5, 129.6, 128.9, 124.6 (q, J=11.4, 7.6, 3.75 Hz), 122.9 (q, J=11.4, 7.6, 3.75 Hz), 78.1, 74.4, 53.5, 49.9, 17.6; MS (ESI) calcd for (M+1)⁺246.2, found 246.1. The hydrochloride salt had mp 183-184° C.; Anal. (C₁₂H₁₅ClF₃NO) C, H, N. Syn isomer 10f: 70.6 mg (12% yield) as a pale yellow oil. [α]²⁰_D +31.4 (c 0.00175, MeOH); ¹H NMR (CDCl₃, 500 MHz) δ 7.68 (s, 1H), 7.58-7.54 (m, 2H), 7.47 (t, J=15.0, 7.5 Hz, 1H), 4.58 (dd, J=9.0, 3.0 Hz, 1H), 3.87 (dd, J=11.5, 3.0 Hz, 1H), 3.71 (dd, J=11.5, 3.0 Hz, 1H), 3.19-3.14 (m, 1H), 3.13-3.09 (m, 1H), 2.98 (dd, J=13.0, 3.0 Hz, 1H), 2.21 (br. s, 1H), 1.31 (d, J=6.5 Hz, 3H); ¹³C NMR (CDCl₃, 125 MHz) ppm 141.5, 129.8, 129.0, 124.6 (q, J=11.4, 7.6, 3.75 Hz), 123.2 (q, J=11.4, 7.6, 4.5 Hz), 77.5, 71.4, 47.4, 46.8, 16.9; MS (ESI) calcd for (M+1)⁺246.2, found 246.2. The fumarate had mp 175-177° C.; Anal. (C₁₆H₁₈F₃NO₅·0.2H₂O) C, H, N.

Scheme 2

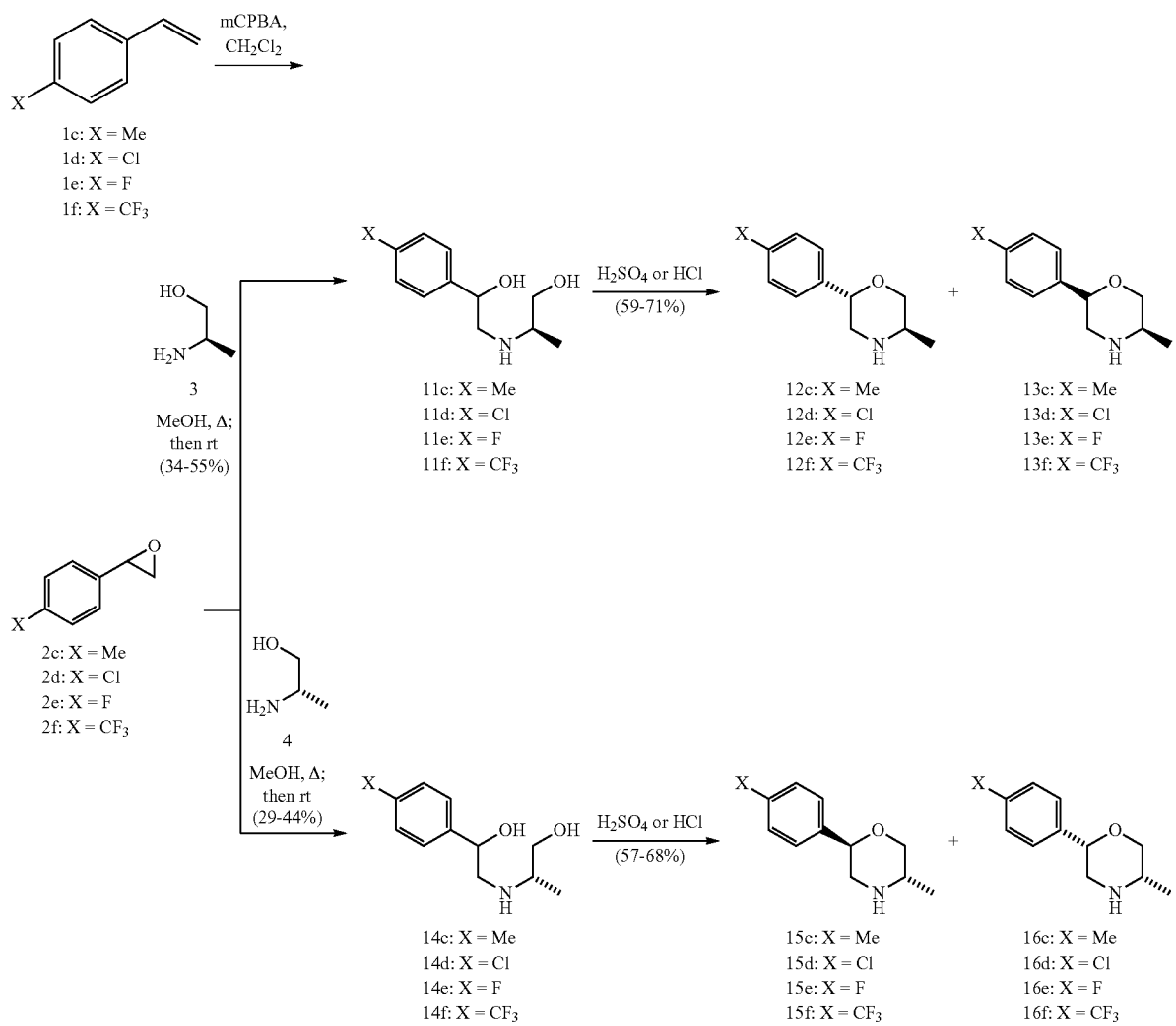

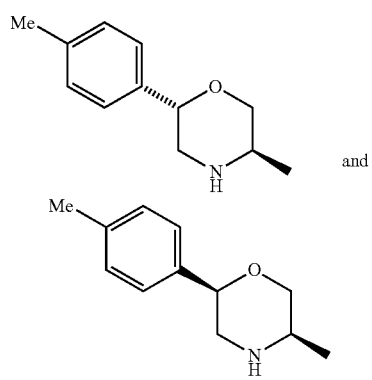

(2S,5R)-5-Methyl-2-p-tolyl-morpholine (12c) and
(2R,5R)-5-Methyl-2-p-tolyl-morpholine (13c)

General procedure A was followed using amine 3 (976 mg, 13.0 mmol) and epoxide 2c (1.59 g, 11.8 mmol) in dry MeOH (39 mL) under $N_2$ to afford 935 mg (38% yield) of amine 11c as a pale yellow oil. General procedure B was then followed using amine 11c (935 mg, 4.47 mmol) in 90% aqueous HCl (12 mL) under $N_2$ to afford a mixture of separable isomers in a 5.2:1 (anti:syn) ratio. Anti isomer 12c: 423 mg (49% yield) isolated as a pale yellow oil. $[\alpha]^{20}{}_D$+37.2 (c 0.0082, MeOH); $^1$H NMR (CDCl$_3$, 300 MHz) δ 7.22 (d, J=9.0 Hz, 2H), 7.13 (d, J=6.0 Hz, 2H), 4.36 (dd, J=9.0, 3.0 Hz, 1H), 3.94 (dd, J=12.0, 3.0 Hz, 1H), 3.28 (t, J=21.0, 12.0 Hz, 1H), 3.04-2.92 (m, 2H), 2.81 (t, J=24.0, 12.0 Hz, 1H), 2.31 (br. S, 4H), 0.99 (d, J=6.0 Hz, 3H); $^{13}$C NMR (CDCl$_3$, 75 MHz) ppm 137.2, 137.1, 128.8, 125.9, 78.4, 74.0, 53.1, 49.6, 20.9, 17.2; MS (ESI) calcd for (M+1)$^+$192.3, found 192.3. The hydrochloride salt had mp 150-151° C.; Anal. (C$_{12}$H$_{18}$ClNO) C, H, N. Syn isomer 13c: 81.7 mg (9.6% yield) isolated as a pale yellow oil contaminated with unreacted starting material. The fumarate had mp 160-162° C.; $[\alpha]^{20}{}_D$–34.4 (c 0.0009, MeOH); $^1$H NMR (CD$_3$OD, 300 MHz) δ 7.31-7.29 (m, 2H), 7.22-7.19 (m, 2H), 6.68 (s, 2H), 4.90-4.68 (m, 1H), 4.07 (dd, J=15.0, 3.0 Hz, 1H), 3.94 (d, J=15.0 Hz, 1H), 161-3.59 (m, 1H), 3.26-3.23 (m, 2H), 2.33 (s, 3H), 1.54 (d, J=9.0 Hz, 3H); $^{13}$C NMR (CD$_3$OD, 75 MHz) ppm 171.5, 139.8, 136.0, 131.0, 130.4, 129.3, 127.2, 77.0, 69.5, 48.2, 44.1, 21.2, 13.6; MS (ESI)

calcd for (M+1)⁺192.3, found 192.1 (free base); Anal. (C₁₆H₂₁NO₅.0.3H₂O) C, H, N.

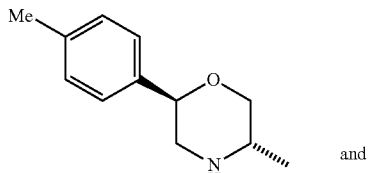

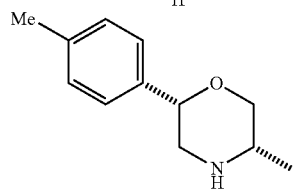

(2R,5S)-5-Methyl-2-p-tolyl-morpholine (15c) and
(2S,5S)-5-Methyl-2-p-tolyl-morpholine (16c)

General procedure A was followed using amine 4 (726 mg, 9.67 mmol) and epoxide 2c (1.18 g, 8.79 mmol) in dry MeOH (29 mL) under N₂ to afford 527 mg (29% yield) of amine 14c as a clear oil. General procedure B was then followed using amine 14c (527 mg, 2.52 mmol) in 90% aqueous HCl (6.8 mL) under N₂ to afford a mixture of separable isomers in a 4.8:1 (anti:syn) ratio. Anti isomer 15c: 225 mg (47% yield) isolated as an off-white solid. [α]²⁰_D −20.8 (c 0.0025, MeOH); ¹H NMR (CDCl₃, 300 MHz) δ 7.24 (d, J=6.0 Hz, 2H), 7.14 (d, J=9.0 Hz, 2H), 4.39 (dd, J=12.0, 3.0 Hz, 1H), 3.95 (dd, J=12.0, 3.0 Hz, 1H), 3.31 (t, J=24.0, 12.0 Hz, 1H), 3.05 (dd, J=12.0, 3.0 Hz, 1H), 3.03-2.95 (m, 1H), 2.84 (br. T, J=21.0, 9.0 Hz, 1H), 2.33 (s, 3H), 1.85 (br. S, 1H), 1.02 (d, J=6.0 Hz, 3H); ¹³C NMR (CDCl₃, 75 MHz) ppm 137.3, 129.0, 126.0, 78.7, 74.3, 53.4, 49.9, 21.1, 17.5; MS (ESI) calcd for (M+1)⁺192.3, found 192.2. The hydrochloride salt had mp 150-151° C.; Anal. (C₁₂H₁₈ClNO) C, H, N. Syn isomer 16c: 46.9 mg (9.7% yield) isolated as a clear oil contaminated with unreacted starting material. The fumarate had mp 175-177° C.; [α]²⁰_D +11.4 (c 0.0007, MeOH); ¹H NMR (CD₃OD, 300 MHz) δ 7.31-7.28 (m, 2H), 7.22-7.19 (m, 2H), 6.68 (s, 2H), 4.73-4.68 (m, 1H), 4.06 (dd, J=12.0 Hz, 1H), 3.93 (d, J=12.0 Hz, 1H), 3.63-3.56 (m, 1H), 3.26-3.21 (m, 2H), 2.33 (s, 3H), 1.54 (d, J=9.0 Hz, 3H); ¹³C NMR (CD₃OD, 75 MHz) ppm 171.6, 139.8, 136.3, 130.4, 127.2, 77.1, 69.6, 48.2, 44.1, 21.2, 13.6; MS (ESI) calcd for (M+1)⁺192.3, found 192.2 (free base); Anal. (C₁₆H₂₁NO₅.0.5H₂O) C, H, N.

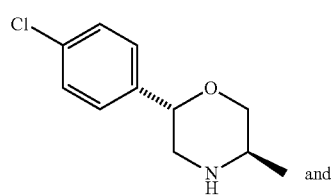

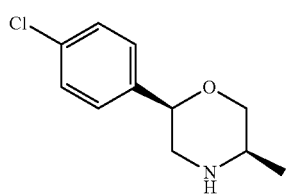

(2S,5R)-2-(4-Chloro-phenyl)-5-methyl-morpholine
(12d) and (2R,5R)-2-(4-Chloro-phenyl)-5-methyl-morpholine (13d)

General procedure A was followed using amine 3 (0.88 mL, 11.3 mmol) and epoxide 2d (1.59 g, 10.3 mmol) in dry MeOH (34 mL) under N₂ to afford 805 mg (34% yield) of amine 11d as a pale yellow oil. General procedure C was then followed using amine 11d (805 mg, 3.50 mmol) in concentrated H₂SO₄ (8.8 mL) to afford a mixture of separable isomers in a 6.8:1 (anti:syn) ratio. Anti isomer 12d: 458 mg (62% yield) as a white solid. [α]²⁰_D +42 (c 0.0051, MeOH); ¹H NMR (CDCl₃, 500 MHz) δ 7.31-7.27 (m, 4H), 4.38 (dd, J=11.0, 2.5 Hz, 1H), 3.95 (dd, J=11.0, 3.0 Hz, 1H), 3.30 (t, J=21.5, 10.0 Hz, 1H), 3.04 (dd, J=12.0, 2.0 Hz, 1H), 3.00-2.94 (m, 1H), 2.78 (br. T, J=23.0, 10.5 Hz, 1H), 1.71 (br. S, 1H), 1.01 (d, J=6.5 Hz, 3H); ¹³C NMR (CDCl₃, 125 MHz) ppm 139.1, 133.5, 128.7, 127.7, 78.2, 74.5, 53.6, 50.0, 17.8; MS (ESI) calcd for (M+1)⁺212.7, found 212.1. The hydrochloride salt had mp 214-216° C.; Anal. (C₁₁H₁₅Cl₂NO) C, H, N. Syn isomer 13d: 67.2 mg (9.1% yield) as a pale yellow oil. [α]²⁰_D −47.7 (c 0.00065, MeOH); ¹H NMR (CDCl₃, 500 MHz) δ 7.36-7.28 (m, 4H), 4.54-4.49 (hidden m, 1H), 3.86 (dd, J=11.5, 3.0 Hz, 1H), 3.69 (dd, J=12.0, 3.0 Hz, 1H), 3.17-3.14 (m, 1H), 3.12-2.96 (m, 1H), 2.94 (dd, J=13.0, 3.0 Hz, 1H), 2.34 (br. S, 1H), 1.30 (d, J=7.0 Hz, 3H); ¹³C NMR (CDCb, 125 MHz) ppm 139.0, 133.6, 128.8, 127.9, 77.5, 71.3, 47.5, 46.8, 16.9; MS (ESI) calcd for (M+1)⁺212.7, found 212.1. The fumarate had mp 178-179° C.; Anal. (C₁₅H₁₈ClNO₅.0.6H₂O) C, H, N.

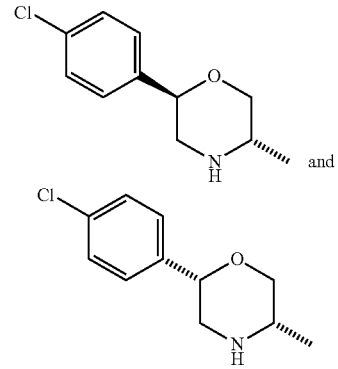

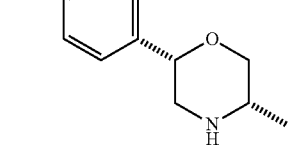

(2R,5S)-2-(4-Chloro-phenyl)-5-methyl-morpholine
(15d) and (2S,5S)-2-(4-Chloro-phenyl)-5-methyl-morpholine (16d)

General procedure A was followed using amine 4 (0.88 mL, 11.3 mmol) and epoxide 2d (1.59 g, 10.3 mmol) in dry MeOH (34 mL) under N₂ to afford 904 mg (38% yield) of amine 14d as a pale yellow semi-solid. General procedure C was then followed using amine 14d (904 mg, 3.94 mmol) in concentrated H₂SO₄ (9.9 mL) to afford a mixture of separable isomers in a 8.8:1 (anti:syn) ratio. Anti isomer 15d: 472 mg (57% yield) as a white solid. [α]²⁰_D −44.1 (c 0.0039, MeOH); ¹H NMR (CDCl₃, 500 MHz) δ 7.33-7.28 (m, 4H), 4.40 (dd, J=10.0, 2.0 Hz, 1H), 3.96 (dd, J=11.0, 3.5 Hz, 1H), 3.31 (t, J=21.5, 10.5 Hz, 1H), 3.06 (dd, J=12.0, 2.5 Hz, 1H), 3.02-2.96 (m, 1H), 2.79 (br. T, J=22.5, 10.0 Hz, 1H), 1.71 (br. S, 1H), 1.02 (d, J=6.5 Hz, 3H); ¹³C NMR (CDCl₃, 125 MHz) ppm 139.1, 133.6, 128.7, 127.7, 78.3, 74.5, 53.7, 50.1, 17.8; MS (APCI) calcd for (M+1)⁺212.7, found 212.2. The hydrochloride salt had mp 213-215° C.; Anal. ($C_{11}H_{15}Cl_2NO$) C, H, N. Syn isomer 16d: 53.7 mg (6.4% yield) as a pale yellow oil. $[\alpha]^{20}_D$+33.8 (c 0.0008, MeOH); ¹H NMR (CDCl₃, 500 MHz) δ 7.37-7.28 (m, 4H), 4.53 (dd, J=8.5, 3.0 Hz, 1H), 3.86 (dd, J=11.5, 3.5 Hz, 1H), 3.70 (dd, J=11.0, 2.5 Hz, 1H), 3.18-3.09 (m, 2H), 2.95 (dd, J=13.0, 3.0 Hz, 1H), 2.08 (br. S, 1H), 1.31 (d, J=7.0 Hz, 3H); ¹³C NMR (CDCl₃, 125 MHz) ppm 139.0, 133.6, 128.8, 127.9, 77.5, 71.3, 47.6, 46.9, 17.0; MS (ESI) calcd for (M+1)⁺212.7, found 212.1. The fumarate had mp 180-181° C.; Anal. ($C_{15}H_{18}ClNO_5$·0.6H₂O) C, H, N.

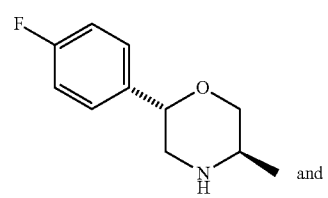

(2S,5R)-2-(4-Fluoro-phenyl)-5-methyl-morpholine (12e) and (2R,5R)-2-(4-Fluoro-phenyl)-5-methyl-morpholine (13e)

General procedure A was followed using amine 3 (0.55 mL, 7.05 mmol) and epoxide 2e (885 mg, 6.41 mmol) in dry MeOH (21 mL) under N₂ to afford 463 mg (34% yield) of amine 11e as a pale yellow oil. General procedure C was then followed using amine 11e (463 mg, 2.17 mmol) in concentrated H₂SO₄ (5.4 mL) to afford a mixture of separable isomers in a 7.5:1 (anti:syn) ratio. Anti isomer 12e: 234 mg (55% yield) as a white solid. $[\alpha]^{20}_D$+45 (c 0.0018, MeOH); NMR (CDCl₃, 500 MHz) δ 7.34-7.30 (m, 2H), 7.04-7.00 (m, 2H), 4.39 (dd, J=11.0, 2.5 Hz, 1H), 3.95 (dd, J=11.5, 3.0 Hz, 1H), 3.31 (t, J=21.5, 10.5 Hz, 1H), 3.05 (dd, J=12.5, 2.5 Hz, 1H), 3.01-2.97 (m, 1H), 2.82 (br. T, J=23.0, 10.5 Hz, 1H), 1.84 (br. S, 1H), 1.01 (d, J=6.5 Hz, 3H); ¹³C NMR (CDCl₃, 125 MHz) ppm 163.5, 161.6, 136.4 (d, J=3.1 Hz), 128.0 (d, J=8.25 Hz), 115.4 (d, J=21.2 Hz), 78.4, 74.5, 53.7, 50.1, 17.8; MS (ESI) calcd for (M+1)⁺196.2, found 196.3. The hydrochloride salt had mp 180-182° C.; Anal. ($C_{11}H_{15}ClFO$) C, H, N. Syn isomer 13e: 31.4 mg (7.4% yield) as a clear oil. $[\alpha]^{20}_D$−38.3 (c 0.0006, MeOH); ¹H NMR (CDCl₃, 500 MHz) δ 7.39-7.35 (m, 2H), 7.06-7.02 (m, 2H), 4.53 (dd, J=9.0, 3.0 Hz, 1H), 3.89 (dd, J=11.5, 3.0 Hz, 1H), 3.70 (dd, J=12.0, 3.0 Hz, 1H), 3.18-3.10 (m, 2H), 2.97-2.93 (m, 1H), 1.33 (d, J=7.0 Hz, 3H); ¹³C NMR (CDCl₃, 125 MHz) ppm 162.9, 161.0, 135.7, 127.6 (d, J=7.5 Hz), 114.9 (d, J=21.2 Hz), 76.7, 70.7, 46.9, 46.2, 16.3; MS (ESI) calcd for (M+1)⁺196.2, found 196.4.

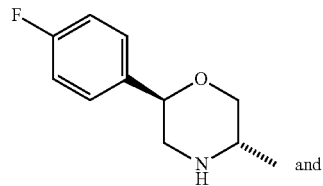

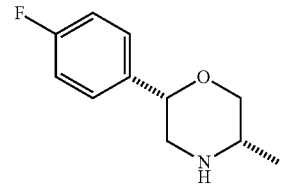

(2R,5S)-2-(4-Fluoro-phenyl)-5-methyl-morpholine (15e) and (2S,5S)-2-(4-Fluoro-phenyl)-5-methyl-morpholine (16e)

General procedure A was followed using amine 4 (530 mg, 7.05 mmol) and epoxide 2e (885 mg, 6.41 mmol) in dry MeOH (21 mL) under N₂ to afford 554 mg (40% yield) of amine 14e as a clear oil. General procedure C was then followed using amine 14e (554 mg, 2.60 mmol) in concentrated H₂SO₄ (6.5 mL) to afford a mixture of separable isomers in a 7.4:1 (anti:syn) ratio. Anti isomer 15e: 307 mg (60% yield) as a white solid. $[\alpha]^{20}_D$−35.9 (c 0.0032, MeOH); ¹H NMR (CDCl₃, 500 MHz) δ 7.34-7.32 (m, 2H), 7.05-7.01 (m, 2H), 4.40 (dd, J=10.0, 2.0 Hz, 1H), 3.95 (dd, J=11.0, 3.5 Hz, 1H), 3.32 (t, J=21.5, 10.5 Hz, 1H), 3.06 (dd, J=12.0, 2.5 Hz, 1H), 3.02-2.98 (m, 1H), 2.82 (br. T, J=23.0, 11.0 Hz, 1H), 1.78 (br. S, 1H), 1.03 (d, J=6.5 Hz, 3H); ¹³C NMR (CDCl₃, 125 MHz) ppm 163.4, 161.5, 136.2 (d, J=3 Hz), 127.8 (d, J=8.2 Hz), 115.3 (d, J=21.2 Hz), 78.2, 74.4, 53.6, 50.0, 17.7; MS (ESI) calcd for (M+1)⁺196.2, found 196.2. The hydrochloride salt had mp 180-182° C.; Anal. ($C_{11}H_{15}ClFNO$) C, H, N. Syn isomer 16e: 41.6 mg (8.2% yield) as a clear oil. $[\alpha]^{20}_D$+35 (c 0.0006, MeOH); ¹H NMR (CDCl₃, 500 MHz) δ 7.39-7.35 (m, 2H), 7.07-7.02 (m, 2H), 4.53 (dd, J=9.0, 3.0 Hz, 1H), 3.88 (dd, J=11.5, 3.0 Hz, 1H), 3.71 (dd, J=11.5, 2.5 Hz, 1H), 3.18-3.10 (m, 2H), 2.95 (dd, J=13.0, 3.0 Hz, 1H), 2.79 (br. S, 1H), 1.33 (d, J=7.0 Hz, 3H); ¹³C NMR (CDCl₃, 125 MHz) ppm 163.5, 161.5, 136.1 (d, J=3.1 Hz), 128.1 (d, J=8.4 Hz), 115.5 (d, J=21.2 Hz), 77.6, 71.3, 47.5, 46.8, 16.8; MS (ESI) calcd for (M+1)⁺196.2, found 196.2. The fumarate had mp 148-149° C.; Anal. ($C_{15}H_{18}FNO_5$·0.5H₂O) C, H, N.

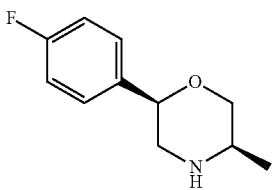

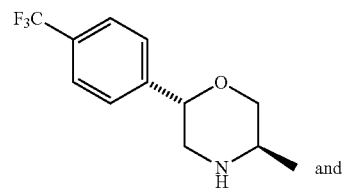

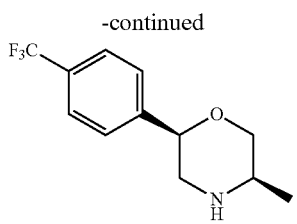

(2S,5R)-5-Methyl-2-(4-trifluoromethyl-phenyl)-morpholine (12f) and (2R,5R)-5-Methyl-2-(4-trifluoromethyl-phenyl)-morpholine (13f)

General procedure A was followed using amine 3 (0.34 mL, 4.96 mmol) and epoxide 2f (848 mg, 4.51 mmol) in dry MeOH (15 mL) under $N_2$ to afford 651 mg (55% yield) of amine 11f as a pale yellow oil. General procedure C was then followed using amine 11f (651 mg, 2.47 mmol) in concentrated $H_2SO_4$ (6.2 mL) to afford a mixture of separable isomers in a 4.8:1 (anti:syn) ratio. Anti isomer 12f: 312 mg (51% yield) as a white solid. $[\alpha]^{20}_D$+48.7 (c 0.0015, MeOH); $^1$H NMR (CDCl$_3$, 500 MHz) δ 7.59 (d, J=8.0 Hz, 2H), 7.46 (d, J=7.5 Hz, 2H), 4.48 (d, J=10.5 Hz, 1H), 3.98 (dd, J=11.5, 3.5 Hz, 1H), 3.23 (t, J=21.5, 10.5 Hz, 1H), 3.10 (dd, J=12.0, 2.0 Hz, 1H), 3.03-2.97 (m, 1H), 2.80 (br. T, J=22.5, 10.5 Hz, 1H), 1.67 (br. S, 1H), 1.03 (d, J=6.5 Hz, 3H); $^{13}$C NMR (CDCl$_3$, 125 MHz) ppm 144.5, 127.6, 126.5, 125.5, 123.2, 78.2, 74.4, 53.6, 50.0, 17.7; MS (ESI) calcd for (M+1)$^+$246.2, found 246.4. The hydrochloride salt had mp 229-231° C.; Anal. (C$_{12}$H$_{15}$ClF$_3$NO) C, H, N. Syn isomer 13f: 65.3 mg (11% yield) as a clear oil. $[\alpha]^{20}_D$–10.7 (c 0.00075, MeOH); $^1$H NMR (CDCl$_3$, 500 MHz) δ 7.60 (d, J=8.0 Hz, 2H), 7.51 (d, J=8.0 Hz, 2H), 4.59 (d, J=8.0 Hz, 1H), 3.86 (dd, J=12.0, 3.0 Hz, 1H), 3.69 (dd, J=11.5, 3.0 Hz, 1H), 3.19-3.08 (m, 2H), 2.98 (dd, J=12.5, 3.0 Hz, 1H), 2.30 (br. S, 1H), 1.29 (d, J=6.0 Hz, 3H); $^{13}$C NMR (CDCl$_3$, 125 MHz) ppm 144.5, 127.6, 126.7, 125.5, 123.3, 77.5, 71.3, 47.6, 46.8, 16.9; MS (ESI) calcd for (M+1)$^+$246.2, found 246.5. The fumarate had mp 185-186° C.; Anal. (C$_{16}$H$_{18}$F$_3$NO$_5$.0.25H$_2$O) C, H, N.

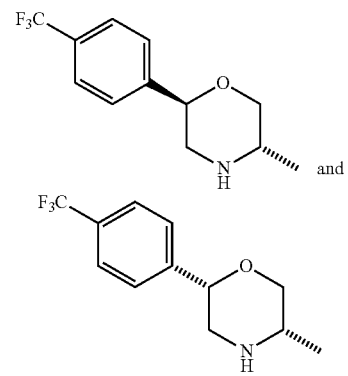

(2R,5S)-5-Methyl-2-(4-trifluoromethyl-phenyl)-morpholine (15f) and (2S,5S)-5-Methyl-2-(4-trifluoromethyl-phenyl)-morpholine (16f)

General procedure A was followed using amine 4 (199 mg, 2.65 mmol) and epoxide 2f (453 mg, 2.41 mmol) in dry MeOH (8 mL) under $N_2$ to afford 278 mg (44% yield) of amine 14f as a thick clear oil. General procedure C was then followed using amine 14f (278 mg, 1.06 mmol) in concentrated $H_2SO_4$ (2.7 mL) to afford a mixture of separable isomers in a 3.8:1 (anti:syn) ratio. Anti isomer 15f: 121 mg (47% yield) as a white solid. $[\alpha]^{20}_D$–45 (c 0.0008, MeOH); $^1$H NMR (CDCl$_3$, 500 MHz) δ 7.58 (d, J=8.5 Hz, 2H), 7.45 (d, J=8.5 Hz, 2H), 4.46 (dd, J=10.0, 2.0 Hz, 1H), 3.96 (dd, J=11.0, 3.0 Hz, 1H), 3.31 (t, J=21.5, 10.5 Hz, 1H), 3.08 (dd, J=12.5, 2.5 Hz, 1H), 3.00-2.96 (m, 1H), 2.72 (br. T, J=23.0, 11.0 Hz, 1H), 1.75 (br. S, 1H), 1.01 (d, J=6.5 Hz, 3H); $^{13}$C NMR (CDCl$_3$, 125 MHz) ppm 144.2, 127.3, 126.2, 125.2 (q, J=11.4, 7.6, 3.75 Hz), 123.0, 77.9, 74.1, 53.3, 49.7, 17.4; MS (ESI) calcd for (M+1)$^+$246.2, found 246.4. The hydrochloride salt had mp 230-231° C.; Anal. (C$_{12}$H$_{15}$ClF$_3$NO) C, H, N. Syn isomer 16f: 31.7 mg (12% yield) as a clear oil. The fumarate had $[\alpha]^{20}_D$+19.1 (c 0.0011, MeOH); $^1$H NMR (CD$_3$OD, 300 MHz) δ 7.73-7.70 (m, 2H), 7.65-7.62 (m, 2H), 6.68 (s, 2H), 4.87-4.83 (hidden m, 1H), 4.08 (dd, J=15.0, 12.0 Hz, 1H), 3.97 (d, J=12.0 Hz, 1H), 3.65-3.58 (m, 1H), 3.36-3.21 (hidden m, 2H), 1.54 (d, J=6.0 Hz, 3H); $^{13}$C NMR (CD$_3$OD, 75 MHz) ppm 171.2, 143.5, 136.1, 127.8, 126.7, 126.6, 76.5, 69.8, 48.3, 44.0, 13.8; MS (ESI) calcd for (M+1)$^+$246.2, found 246.2 (free base); mp 179-180° C.; Anal. (C$_{16}$H$_{18}$F$_3$NO$_5$.0.6H$_2$O) C, H, N.

Scheme 3

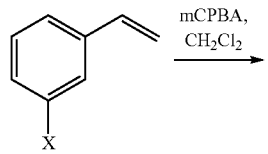

1a: X = H
1b: X = OMe
1c: X = Me
1d: X = Cl
1e: X = F
1f: X = CF$_3$

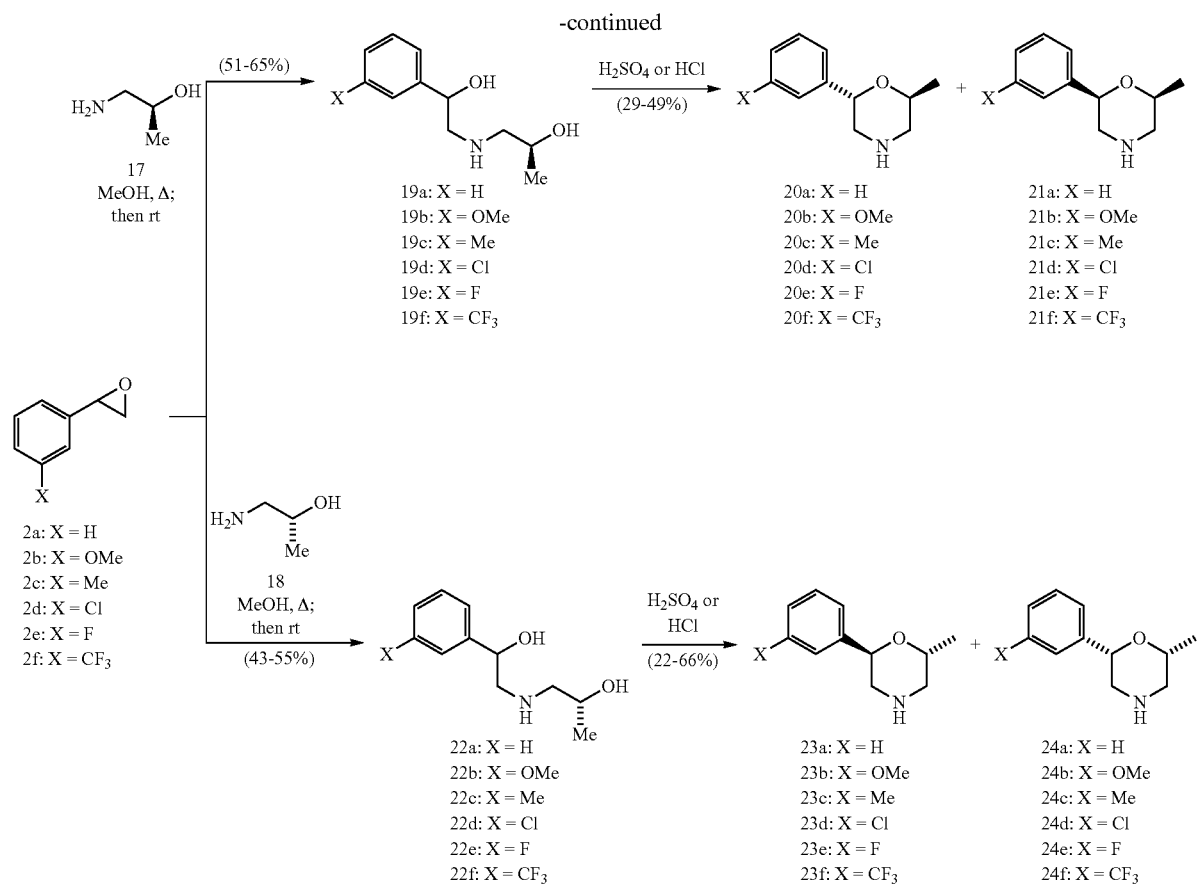

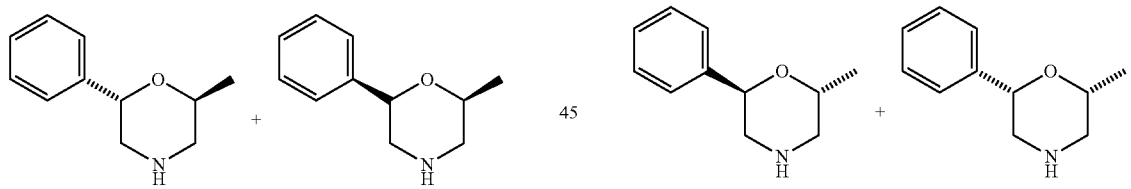

(2S,6S)-2-Methyl-6-phenyl-morpholine (20a) and (2R,6S)-2-Methyl-6-phenyl-morpholine (21a)

General procedure A was followed using amine 17 (0.50 mL, 6.35 mmol) and epoxide 2a (0.60 mL, 5.27 mmol) in dry MeOH (32 mL) under $N_2$ to afford 529 mg (51% yield) of amine 19a as a pale yellow oil. General procedure B was then followed using amine 19a (529 mg, 2.71 mmol) in 50% aqueous HCl (7 mL) under $N_2$ to afford 138 mg (29% yield) of inseparable morpholines 20a and 21a as a clear sticky oil in a 3:1 (syn:anti) ratio. $[\alpha]^{20}_D$ −57.7 (c 0.0035, MeOH); MS (APCI) calcd for (M+1)$^+$ 178.2, found 178.4. The fumarate had mp 131-134° C.; Anal ($C_{15}H_{19}NO_5 \cdot 0.2H_2O$) C, H, N.

(2R,6R)-2-Methyl-6-phenyl-morpholine (23a) and (2S,6R)-2-Methyl-6-phenyl-morpholine (24a)

General procedure A was followed using amine 18 (0.50 mL, 6.35 mmol) and epoxide 2a (0.60 mL, 5.27 mmol) in dry MeOH (32 mL) under $N_2$ to afford 446 mg (43% yield) of amine 22a as a pale yellow oil. General procedure B was then followed using amine 22a (446 mg, 2.28 mmol) in 50% aqueous HCl (6.2 mL) under $N_2$ to afford 89.1 mg (22% yield) of inseparable morpholines 23a and 24a as a clear sticky oil in a 3:1 (syn:anti) ratio. $[\alpha]^{20}_D$ +23.6 (c 0.00165, MeOH); MS (APCI) calcd for (M+1)$^+$ 178.2, found 178.2. The fumarate had mp 131-133° C.; Anal. ($C_{15}H_{19}NO_5 \cdot 0.2H_2O$) C, H, N.

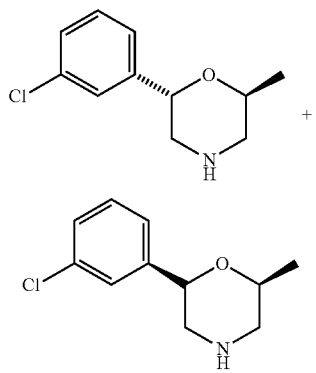

(2S,6S)-2-(3-Chloro-phenyl)-6-methyl-morpholine (20d) and (2R,6S)-2-(3-Chloro-phenyl)-6-methyl-morpholine (21d)

General procedure A was followed using amine 17 (0.50 mL, 6.35 mmol) and epoxide 2d (814 mg, 5.27 mmol) in dry MeOH (21 mL) under $N_2$ to afford 787 mg (65% yield) of amine 19d as a thick clear oil. General procedure C was then followed using amine 19d (787 mg, 3.43 mmol) in concentrated $H_2SO_4$ (8.6 mL) to afford 354 mg (49% yield) of inseparable morpholines 20d and 21d as a clear sticky oil in a 3:1 (syn:anti) ratio. $[\alpha]^{20}_D$ –37.7 (c 0.0022, MeOH); MS (ESI) calcd for (M+1)$^+$212.7, found 212.1. The fumarate had mp 136-137° C. Anal ($C_{15}H_{18}ClNO_5$) C, H, N.

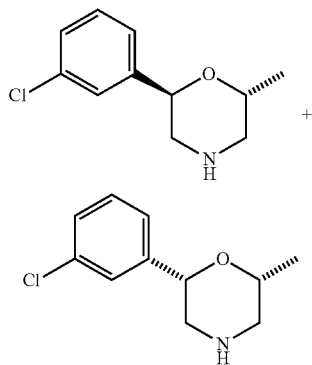

(2R,6R)-2-(3-Chloro-phenyl)-6-methyl-morpholine (23d) and (2S,6R)-2-(3-Chloro-phenyl)-6-methyl-morpholine (24d)

General procedure A was followed using amine 18 (0.50 mL, 6.35 mmol) and epoxide 2d (815 mg, 5.27 mmol) in dry MeOH (21 mL) under $N_2$ to afford 663 mg (55% yield) of amine 22d as a thick pale yellow oil. General procedure C was then followed using amine 22d (663 mg, 2.89 mmol) in concentrated $H_2SO_4$ (7.2 mL) to afford 406 mg (66% yield) of inseparable morpholines 23d and 24d as a clear sticky oil in a 3:1 (syn:anti) ratio. $[\alpha]^{20}_D$+22.2 (c 0.0037, MeOH); MS (ESI) calcd for (M+1)$^+$212.7, found 212.1. The fumarate had mp 136-137° C.; Anal. ($C_{15}H_{18}ClNO_5$) C, H, N.

Example 4

DA, NE, 5-HT Release Assays

A series of compounds were assayed for release of dopamine, serotonin, and norepinephrine as well as for activity at the 5-HT$_{2B}$ receptor. This data is shown below in Table 3.

DA, NE and 5-HT Release Assays

[$^3$H]MPP$^+$ was used as the radioligand for both the DA and NE release assays, because this method led to an improved signal-to-noise ratio. Rat caudate (for DA release) or whole brain minus cerebellum and caudate (for NE and 5-HT release), was homogenized in ice-cold 10% sucrose containing 1 μM reserpine. Nomifensine (100 nM) and GBR12935 (100 nM) were added to the sucrose solution for [$^3$H]5-HT release experiments to block any potential [$^3$H]5-HT reuptake into NE and DA nerve terminals. For the DA release assay, 100 nM desipramine and 100 nM citalopram were added to block [$^3$H]MPP$^+$ uptake into NE and 5-HT nerves. For the NE release assay, 50 nM GBR12935 and 100 nM citalopram were added to block [$^3$H]MPP$^+$ uptake into DA and 5-HT nerves. After 12 strokes with a Potter-Elvehjem homogenizer, homogenates were centrifuged at 1000×g for 10 min at 0-4° C. and the supernatants were retained on ice (synaptosomal preparation).

Synaptosomal preparations were incubated to steady state with 5 nM [$^3$H]MPP (60 min) or 5 nM [$^3$H]5-HT (60 min) in Krebs-phosphate buffer (without BSA) (pH 7.4), which contained 154.4 mM NaCl, 2.9 mM KCl, 1.1 mM CaCl$_2$, 0.83 mM MgCl$_2$, 5 mM glucose, 1 mg/mL ascorbic acid, 50 μM pargyline plus 1 μM reserpine in a polypropylene beaker with stirring at 25° C. with the appropriate blockers. After incubation to steady state, 850 μl of synaptosomes preloaded with [$^3$H]ligand were added to 12×75 mm polystyrene test tubes that contained 150 μl test drug in uptake buffer plus 1 mg/ml BSA. After 5 min ($^3$H]5-HT) or 30 min (NE and DA assays) the release reaction was terminated by dilution with 4 ml wash buffer (10 mM Tris-HCl pH 7.4 containing 0.9% NaCl at 25° C.) followed by rapid vacuum filtration over Whatman GF/B filters using a Brandel Harvester. The filters were rinsed twice with 4 ml wash buffer using the Brandel Harvester, and the retained tritium was counted by a Taurus liquid scintillation counter at 40% efficiency after an overnight extraction in 3 ml Cytoscint (ICN).

Substrate Reversal Experiments

For substrate reversal experiments, test drugs were tested at approximately ED$_{80}$ doses in the absence and presence of blockers (250 nM GBR1209 for DAT, 166 nM desipramine for NET, 100 nM fluoxetine for SERT). Substrate activity was detected by a significant reversal of the releasing effect of the test drug.

Data Analysis and Statistics

As previously described (Rothman R B, Baumann M H, Dersch C M, Romero D V, Rice K C, Carroll F I and Partilla J S Synapse 39: 32-41 (2001), incorporated herein by reference), EC$_{50}$ values were determined using the nonlinear least squares curve fitting program MLAB-PC (Civilized Software, Bethesda, Md.). In substrate reversal experiments, statistical significance was determined using the Student's t-test.

TABLE 3

Monoamine Release and 5HT$_{2B}$ Activity of a Series of Phenmetrazine Analogs

| Compound | Release (EC50 nm or % @ 10 μM) | | | 5-HT$_{2B}$ Activity | |
|---|---|---|---|---|---|
| | | | | Agonist | Antagonist |
| | DA | 5-HT | NE | (% @ 10 μM) | (% at 1 μM) |
| PAL55 | 131 | 7765 | 50 | 0 | — |
| PAL56 | 87 | 3246 | 37 | 0 | 42 |
| PAL57 | 415 | inactive | 63 | 0 | |
| PAL60 | 1457 | Inactive | 349 | 0 | |
| PAL583 | 29% | 0% | 69% | 0% | 6% |
| PAL587 | 34% | 6% | 67% | 0 | 0 |

TABLE 3-continued

Monoamine Release and 5HT$_{2B}$ Activity of a Series of Phenmetrazine Analogs

| Compound | Release (EC50 nm or % @ 10 µM) | | | 5-HT$_{2B}$ Activity | |
|---|---|---|---|---|---|
| | DA | 5-HT | NE | Agonist (% @ 10 µM) | Antagonist (% at 1 µM) |
| PAL589 | 28% | 56% | 47% | 0 | 12 |
| PAL590 | 39% | 41% | 62% | 0 | 16 |
| PAL593 | 100% | 95% | 93% | 0 | 1 |
| PAL594 | 100% | 95% | 82% | 2 | 28 |
| PAL632 | 98% | 31% | 96% | 2 | 12 |
| PAL635 | 95% | 88% | 100% | 0% | — |

* denotes relative configuration

An additional series of compounds of the present invention, having the stereochemistry indicated in the figure above Table 4 below, was synthesized and tested for dopamine, serotonin, and norepinephrine release, as well as for serotonin uptake inhibition. The initial set of compounds was based on PAL-56, which is (+)-phenmetrazine, and which was found to be an effective DA/5HT releaser. The (−)-isomer is also active as a releaser, but is not as potent. The two cis compounds were weaker uptake inhibitors. Adding substituents to the phenyl ring resulted in improvements in 5HT release, such as the 3-chloro compounds (PAL-594), shown in Table 4. The data in Table 4 is shown either as % EC50 of release or the EC50 value has been calculated in nM. Two of the compounds, PAL-704 and PAL-788, show unique and interesting hybrid activity in that they are DA/NE releasers, but are 5HT uptake inhibitors.

TABLE 4

Comparison of the DA, 5-HT, and NE Releasing Activity of a Series of Phenmetrazine Analogs

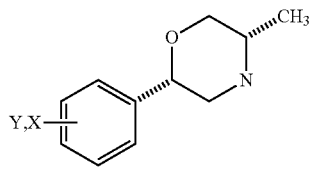

| PAL# | R | X,Y | DA Rel | 5HT Rel | 5HT Up | NE Rel |
|---|---|---|---|---|---|---|
| 56 | Me | H | 87 nM | 3246 nM | | 38 nM |
| 593 | Me | 3F | 43 nM | 2558 nM | | 30 nM |
| 594 | Me | 3Cl | 27 nM | 301 nM | | 75 nM |
| 632 | H | H | 86 nM | 20260 nM | | 79 nM |
| 635 | H | 4F | 529 nM | 2403 nM | | 285 nM |
| 678 | H | Naphthyl | 79% | 92% | | 88% |
| 704 | Me | Naphthyl | 111 nM | | 105 nM | 203 nM |
| 747 | Me | 4Me | 91% | 79% | | 95% |
| 748 | Me | 4F | 98% | 94% | | 93% |
| 749 | Me | 4Cl | 88% | 76% | | 93% |
| 751 | Me | 4OMe | 50% | 64% | | 84% |
| 772 | Me | 4CN | 0% | 53% | | 100% |
| 773 | Me | 3Me | 98% | 82% | | 80% |
| 780 | Me | 3OH | 97% | 70% | | 100% |
| 786 | Me | 3CN | 99% | 99% | | 100% |
| 788 | Me | 3,4-diCl | 60% | | 95% | 98% |
| 821 | Me | 4F,3Cl | 94% | 71% | | 80% |
| 823 | Me | 3OMe | 96% | 78% | | 86% |
| 1001 | H | 2CF3 | 64% | | 25% | 50% |

An additional set of compounds, wherein all compounds have a $CH_3$ group at the $R_4$ position, was generated, and tested for dopamine release, dopamine reuptake, serotonin release, and norepinephrine release. In all cases, the (2S, 5S)-analog was more active as a releaser, as shown in Table 5. The other isomers were either inactive or uptake inhibitors, the potency depending on the substituent (not shown).

TABLE 5

Comparison of the DA, 5-HT, and NE Releasing Activity of a Series of (2S,5S)-5-methyl-2-phenylmorpolines

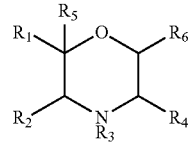

| PAL# | X,Y | DA Rel | DA Up | 5HT Rel | NE Rel |
|---|---|---|---|---|---|
| 730 | H | 212 | | 107 | 79 |
| 738 | 3Cl | 58 | | 23 | 65 |
| 880 | 3OMe | 56% | | 100% | 76% |
| 886 | 3Me | 86% | | 98% | 88% |
| 890 | 3F | 96% | | 89% | 96% |
| 895 | 3CF3 | 45% | | 100% | 77% |
| 899 | 4Cl | | 90% | 76% | 65% |
| 903 | 4F | 65% | | 100% | 100% |
| 910 | 4CF3 | 15% | | 80% | 15% |
| 914 | 4Me | | 88% | 88% | 81% |

That which is claimed:

1. A compound according to the formula:

[structure: morpholine ring with R1, R5 on one carbon; R2 on adjacent; R3 on N; R4, R6 on other carbons]

wherein:

$R_1$ is optionally substituted aryl, wherein the substituents are selected from the group consisting of OH, optionally substituted C1-4 alkyl, optionally substituted C1-4 alkoxy, optionally substituted C2-4 alkenyl, optionally substituted C2-4 alkynyl, Cl, F, I, acylamido, CN, $CF_3$, $N_3$, $CONH_2$, $CO_2R_{12}$, $CH_2OH$, $CH_2OR_{12}$, $NHCOR_{12}$, $NHCO_2R_{12}$, $CONR_{12}R_{13}$, C1-3 alkylthio, $R_{12}SO$, $R_{12}SO_2$, $CF_3S$, and $CF_3SO_2$, wherein $R_{12}$ and $R_{13}$ are each independently selected from H or optionally substituted C1-10 alkyl;

$R_2$ is H or optionally substituted C1-3 alkyl;

$R_3$ is H;

$R_4$ is optionally substituted C1-3 alkyl; and $R_5$ is H or OH;

$R_6$ is H or optionally substituted C1-3 alkyl;

with the proviso that when $R_2$ is $CH_3$ and $R_1$ is phenyl, then the phenyl ring of $R_1$ is substituted with one or more substituents and $R_1$ is trans to $R_2$;

wherein the compound comprises an enantiomeric excess of at least 95% of the (2S-5S) enantiomer, or a pharmaceutically acceptable ester, amide, salt, or solvate thereof.

2. The compound of claim 1, wherein $R_1$ is phenyl, substituted phenyl, naphthyl, or substituted naphthyl.

3. The compound of claim 1, wherein $R_3$ is H and $R_1$ is substituted aryl.

4. The compound according to claim 1, having the formula:

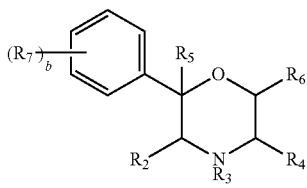

wherein:
each $R_7$ represents a substituent independently selected from the group consisting of OH, optionally substituted C1-4 alkyl, optionally substituted C1-4 alkoxy, optionally substituted C2-4 alkenyl, optionally substituted C2-4 alkynyl, Cl, F, I, acylamido, CN, $CF_3$, $N_3$, $CONH_2$, $CO_2R_{12}$, $CH_2OH$, $CH_2OR_{12}$, $NHCOR_{12}$, $NHCO_2R_{12}$, $CONR_{12}R_{13}$, C1-3 alkylthio, $R_{12}SO$, $R_{12}SO_2$, $CF_3S$, and $CF_3SO_2$, wherein $R_{12}$ and $R_{13}$ are each independently selected from H or optionally substituted C1-10 alkyl; and
b is an integer from 0-5;
with the proviso that when $R_2$ is $CH_3$, then b is an integer from 1-5 and the phenyl is trans to $R_2$,
wherein the compound comprises an enantiomeric excess of at least 95% of the (2S-5S) enantiomer,
or a pharmaceutically acceptable ester, amide, salt, or solvate thereof.

5. The compound according to claim 4, wherein b is an integer from 1-5, and each $R_7$ is independently selected from the group consisting of optionally substituted C1-4 alkyl, optionally substituted C1-4 alkoxy, OH, CN, and $CF_3$.

6. The compound according to claim 5, wherein b is 1 and the $R_7$ substituent is located meta or para to the morpholine substituent on the phenyl ring.

7. The compound according to claim 1, having the formula:

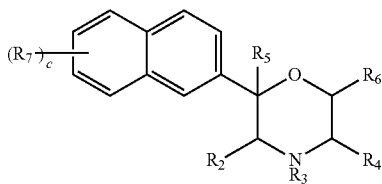

wherein:
each $R_7$ represents a substituent independently selected from the group consisting of OH, optionally substituted C1-4 alkyl, optionally substituted C1-3 alkoxy, optionally substituted C2-4 alkenyl, optionally substituted C2-4 alkynyl, halogen, amino, acylamido, CN, $CF_3$, $NO_2$, $N_3$, $CONH_2$, $CO_2R_{12}$, $CH_2OH$, $CH_2OR_{12}$, $NR_{12}R_{13}$, $NHCOR_{12}$, $NHCO_2R_{12}$, $CONR_{12}R_{13}$, C1-3 alkylthio, $R_{12}SO$, $R_{12}SO_2$, $CF_3S$, and $CF_3SO_2$; and
c is an integer from 0-7,
or a pharmaceutically acceptable ester, amide, salt, or solvate thereof.

8. The compound according to claim 1, wherein $R_2$ is H or $CH_3$.

9. The compound according to claim 1, wherein $R_4$ is $CH_3$.

10. The compound of claim 1, wherein the compound is selected from the group consisting of:
2-(3-chloro-phenyl)-5-methyl-morpholine;
2-(3-fluoro-phenyl)-5-methyl-morpholine;
2-(3-methoxy-phenyl)-5-methyl-morpholine;
2-(4-chloro-phenyl)-5-methyl-morpholine; and
2-(4-fluoro-phenyl)-5-methyl-morpholine;
or a pharmaceutically acceptable ester, amide, salt, or solvate thereof.

11. The compound according to claim 1, wherein the compound is one or more of a dopamine releaser, norepinephrine releaser, serotonin releaser, dopamine uptake inhibitor, norepinephrine uptake inhibitor, and serotonin uptake inhibitor.

12. The compound according to claim 1, wherein the compound is a dopamine releaser or a dual serotonin and dopamine releaser.

13. The compound according to claim 1, wherein the compound is inactive at the $5HT_{2B}$ receptor.

14. A pharmaceutical composition comprising a compound according to claim 1 and one or more pharmaceutically acceptable carriers.

15. A method for treating or delaying the progression of disorders that are alleviated by modulating monoamine release in a patient comprising administering a therapeutically effective amount of at least one compound according to claim 1.

16. The method of claim 15, wherein the disorder is selected from the group consisting of addiction, depression, obesity, bipolar disorder, attention deficit disorder (ADD), attention deficit/hyperactivity disorder (ADHD), hypoactive sexual desire disorder, antidepressant-induced sexual dysfunction, orgasmic dysfunction, seasonal affective disorder/winter depression, mania, bulimia and other eating disorders, panic disorders, obsessive compulsive disorder, schizophrenia, schizo-affective disorder, Parkinson's disease, narcolepsy, anxiety disorders, insomnia, chronic pain, migraine headaches, and restless legs syndrome.

17. The compound according to claim 4, wherein $R_2$ is H or $CH_3$.

18. The compound according to claim 7, wherein $R_2$ is H or $CH_3$.

19. The compound according to claim 4, wherein $R_4$ is $CH_3$.

20. The compound according to claim 7, wherein $R_4$ is $CH_3$.

21. The compound according to claim 5, wherein b is 1 and the $R_7$ substituent is located meta to the morpholine substituent on the phenyl ring.

* * * * *